United States Patent
Bramlett et al.

(10) Patent No.: US 10,941,414 B2
(45) Date of Patent: Mar. 9, 2021

(54) COMPOSITIONS AND METHODS FOR CONTROLLING PLANT PESTS

(71) Applicants: SYNGENTA PARTICIPATIONS AG, Basel (CH); SYNGENTA CROP PROTECTION LLC, Durham, NC (US)

(72) Inventors: Matthew Richard Bramlett, Gent-Zwijnaarde (BE); Katherine Seguin, Research Triangle Park, NC (US); Vance Cary Kramer, Research Triangle Park, NC (US); Mark Scott Rose, Research Triangle Park, NC (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/742,217

(22) PCT Filed: Jun. 30, 2016

(86) PCT No.: PCT/US2016/040382
§ 371 (c)(1),
(2) Date: Jan. 5, 2018

(87) PCT Pub. No.: WO2017/007679
PCT Pub. Date: Jan. 12, 2017

(65) Prior Publication Data
US 2018/0194813 A1     Jul. 12, 2018

Related U.S. Application Data

(60) Provisional application No. 62/189,573, filed on Jul. 7, 2015.

(51) Int. Cl.
*C12N 15/82*     (2006.01)
*C07K 14/325*    (2006.01)

(52) U.S. Cl.
CPC ........ *C12N 15/8286* (2013.01); *C07K 14/325* (2013.01); *Y02A 40/146* (2018.01)

(58) Field of Classification Search
None
See application file for complete search history.

(56) References Cited

U.S. PATENT DOCUMENTS

| | | | | |
|---|---|---|---|---|
| 6,489,542 | B1 * | 12/2002 | Corbin | C07K 14/325 800/302 |
| 2003/0167517 | A1 | 9/2003 | Arnaut et al. | |
| 2012/0266335 | A1 * | 10/2012 | Larrinua | A23D 9/00 800/302 |

FOREIGN PATENT DOCUMENTS

| | | |
|---|---|---|
| WO | 1998/40490 A2 | 9/1998 |
| WO | 01/19859 A2 | 3/2001 |
| WO | 0113731 A1 | 3/2001 |
| WO | WO2002057664 A2 | 7/2002 |
| WO | 2009/052242 A2 | 4/2009 |
| WO | 2010141953 A2 | 12/2010 |
| WO | 2011075586 A2 | 6/2011 |
| WO | 2013134734 A2 | 9/2013 |
| WO | 2015/021354 A2 | 2/2015 |
| WO | 2016094165 A1 | 6/2016 |

OTHER PUBLICATIONS

Widner & Whiteley (1989) B Bacteriol 171(2):965-74.*
GenBank (2019) P0A377.*
Mandal et al. (2007) Protein Eng Des Sel 20:599-606.*
Aronson & Shai (2001) FEMS Microbiol Lett 195:1-8.*
De Maagd et al. (2001) Trends Genet 17:193-99.*
Guo et al. (2004) Proc Natl Acad Sci USA 101:9205-10.*
De Maagd et al. (1999) Appl Environ Microbiol 65:4369-74.*
Tounsi et al. (2003) J Appl Microbiol 95:23-28.*
Angsuthanasombat et al. (2001) J Biochem Mol Biol 34:402-07.*
Ballottari et al. (2017) Biochim Biophys Acta 1817:143-57.*
Argôlo-Filho & Loguercio (2014) Insects 5:62-91.*
Supplementary European Search Report for EP Application No. 16821834.5 dated Nov. 22, 2018.
Hongxia Liang et al; Characterization of cry2-type genes of Bacillus thuringiensis strains from soil-isolated of Sichuan basin, China; Brazilian Journal of Microbiology; vol. 42 (1); pp. 140-146, 2011.
Karim Shahid et al; Determination of receptor binding properties of Bacillus thuringiensis delta-endotoxins to cotton bollworm (*Helicoverpa zea*) and pink bollworm (*Pecinophora gossypiella*) midgut brush border membrane vsicles; Pesticide Biochem. & Physio. Academic Press, US; vol. 67 (3), pp. 198-216; 2000.
Notification of Transmittal of the International Search Report dated Nov. 20, 3016 mailed in International Application No. PCT/US16/40382 filed Jun. 30, 2016.
Crickmore N., et al.,"Revision of the nomenclature for the Bacillus thuringiensis pesticidal crystal proteins", Microbiology and Molecular Biology Reviews, American Society for Microbiology, 1998, vol. 62, No. 3, pp. 807-813.
Widner W R et al, "Two Highly Related Insecticidal Crystal Proteins of *Bacillus thuringiensis* Subsp. Kurstaki Possess Different Host Range Specificities", Journal of Bacteriology, 1989, vol. 171, No. 2, pp. 965-974.
Kota M et al, "Overexpression of the Bacillus thuringiensis (BT) Cry2Aa2 protein in chloroplasts confers resistance to plants against susceptible and Bt-resistant insects", Proceedings of The National Academy of Sciences of USA, National Academy of Science., 1999, vol. 96, No. 5, pp. 1840-1845.
Pakula A. et al., "Genetic analysis of protein stability and function", Annual Review Genet., 1989, vol. 23, pp. 289-310

* cited by examiner

*Primary Examiner* — Russell T Boggs
(74) *Attorney, Agent, or Firm* — Amy Krom

(57) ABSTRACT

Novel insecticidal proteins that are toxic to lepidopteran pests are disclosed. The DNA encoding the insecticidal proteins can be used to transform prokaryotic and eukaryotic organisms to express the insecticidal proteins. The recombinant organisms or compositions containing the recombinant organisms or the insecticidal proteins alone or in combination with an appropriate agricultural carrier can be used to control lepidopteran pests in various environments.

18 Claims, No Drawings

Specification includes a Sequence Listing.

COMPOSITIONS AND METHODS FOR CONTROLLING PLANT PESTS

The official copy of the sequence listing is submitted electronically via EFS-Web as an ASCII formatted sequence listing with a file named "80838-WO-REG-ORG-P-1_SeqList_ST25.txt", created on Jul. 7, 2015, and having a size of 56 kilobytes and is filed concurrently with the specification. The sequence listing contained in this ASCII formatted document is part of the specification and is herein incorporated by reference in its entirety.

CROSS REFERENCE TO RELATED APPLICATIONS

This application claims the benefit of U.S. Ser. No. 62/189,573, filed Jul. 7, 2015, which is incorporated by reference in its entirety for all purposes.

FIELD OF THE INVENTION

This invention relates to pesticidal proteins and the nucleic acid molecules that encode them, as well as compositions and methods for controlling plant pests.

BACKGROUND

*Bacillus thuringiensis* (Bt) is a gram-positive spore forming soil bacterium characterized by its ability to produce crystalline inclusions that are specifically toxic to certain orders and species of plant pests, including insects, but are harmless to plants and other non-target organisms. For this reason, compositions comprising *Bacillus thuringiensis* strains or their insecticidal proteins can be used as environmentally-acceptable insecticides to control agricultural insect pests or insect vectors of a variety of human or animal diseases.

Crystal (Cry) proteins from *Bacillus thuringiensis* have potent insecticidal activity against predominantly lepidopteran, dipteran, and coleopteran pest insects. These proteins also have shown activity against pests in the Orders Hymenoptera, Homoptera, Phthiraptera, Mallophaga, and Acari pest orders, as well as other invertebrate orders such as Nemathelminthes, Platyhelminthes, and Sarcomastigorphora (Feitelson, J. 1993. The *Bacillus Thuringiensis* family tree. In Advanced Engineered Pesticides. Marcel Dekker, Inc., New York, N.Y.). These proteins were originally classified as CryI to CryVI based primarily on their insecticidal activity. The major classes were Lepidoptera-specific (I), Lepidoptera- and Diptera-specific (II), Coleoptera-specific (III), Diptera-specific (IV), and nematode-specific (V) and (VI). The proteins were further classified into subfamilies; more highly related proteins within each family were assigned divisional letters such as CryIA, CryIB, CryIC, etc. Even more closely related proteins within each division were given names such as CryIC(a), CryIC(b), etc. The terms "Cry toxin" and "delta-endotoxin" have been used interchangeably with the term "Cry protein." Current nomenclature for Cry proteins and genes is based upon amino acid sequence homology rather than insect target specificity (Crickmore et al. (1998) Microbiol. Mol. Biol. Rev. 62:807-813). In this more accepted classification, each toxin is assigned a unique name incorporating a primary rank (an Arabic number), a secondary rank (an uppercase letter), a tertiary rank (a lowercase letter), and a quaternary rank (another Arabic number). In the current classification, Roman numerals have been exchanged for Arabic numerals in the primary rank. For example, "CryIA(a)" under the older nomenclature is now "Cry1Aa" under the current nomenclature. According to Ibrahim et al. (2010, Bioeng. Bugs, 1:31-50), the Cry toxins can still be separated into six major classes according to their insect host specificities and include: Group 1-lepidopteran e.g., Cry1, Cry9 and Cry15); group 2-lepidopteran and dipteran (e.g., Cry2); group 3-coleopteran (Cry3, Cry7 and Cry8); group 4-dipteran (Cry4, Cry10, Cry11, Cry16, Cry17, Cry19 and Cry20); group 5-lepidopteran and coleopteran (Cry1I); and group 6-nematodes (Cry6). The Cry1I, Cry2, Cry3, Cry10 and Cry11 toxins (73-82 kDa) are unique because they appear to be natural truncations of the larger Cry1 and Cry4 proteins (130-140 kDa).

Cry proteins are globular protein molecules which accumulate as protoxins in crystalline form during the sporulation stage of Bt. After ingestion by a pest, the crystals are typically solubilized to release protoxins, which can range in size, for example, from 130-140 kDa for many of the lepidopteran-active Cry proteins, such as Cry1 and Cry9, and 60-80 kDa for the coleopteran-active Cry3 proteins and the lepidopteran/dipteran-active Cry2 proteins. After the crystals are solubilized by a susceptible insect the released protoxins are processed by proteases in the insect gut, for example trypsin and chymotrypsin, to produce a protease-resistant core Cry protein toxin. This proteolytic processing involves the removal of amino acids from different regions of the various Cry protoxins. For example, Cry protoxins that are 130-140 kDa are typically activated through the proteolytic removal of an N-terminal peptide of 25-30 amino acids and approximately half of the remaining protein from the C-terminus resulting in an approximately 60-70 kDa mature Cry toxin. The protoxins that are 60-80 kDa, e.g. Cry2 and Cry3, are also processed but not to the same extent as the larger protoxins. The smaller protoxins typically have equal or more amino acids removed from the N-terminus than the larger protoxins but less amino acids removed from the C-terminus. For example, proteolytic activation of Cry2 family members typically involves the removal of approximately 40-50 N-terminal amino acids. Many of the Cry proteins are quite toxic to specific target insects, but many have narrow spectrums of activity.

Cry proteins generally have five conserved sequence domains, and three conserved structural domains (see, for example, de Maagd et al. (2001) Trends Genetics 17:193-199). The first conserved structural domain, called Domain I, typically consists of seven alpha helices and is involved in membrane insertion and pore formation. Domain II typically consists of three beta-sheets arranged in a Greek key configuration, and domain III typically consists of two antiparallel beta-sheets in 'jelly-roll' formation (de Maagd et al., 2001, supra). Domains II and III are involved in receptor recognition and binding, and are therefore considered determinants of toxin specificity.

Numerous commercially valuable plants, including common agricultural crops, are susceptible to attack by plant pests including insect and nematode pests, causing substantial reductions in crop yield and quality. For example, plant pests are a major factor in the loss of the world's important agricultural crops. About $8 billion are lost every year in the United States alone due to infestations of invertebrate pests including insects. Insect pests are also a burden to vegetable and fruit growers, to producers of ornamental flowers, and to home gardeners.

Insect pests are mainly controlled by intensive applications of chemical pesticides, which are active through inhibition of insect growth, prevention of insect feeding or reproduction, or cause death. Biological pest control agents, such as *Bacillus thuringiensis* strains expressing pesticidal toxins such as Cry proteins, have also been applied to crop plants with satisfactory results, offering an alternative or compliment to chemical pesticides. The genes coding for some of these Cry proteins have been isolated and their expression in heterologous hosts such as transgenic plants have been shown to provide another tool for the control of economically important insect pests.

Good insect control can thus be reached, but certain chemicals can sometimes also affect non-target beneficial insects and certain biologicals have a very narrow spectrum of activity. In addition, the continued use of certain chemical and biological control methods heightens the chance for insect pests to develop resistance to such control measures. This has been partially alleviated by various resistance management practices, but there remains a need to develop new and effective pest control agents that provide an economic benefit to farmers and that are environmentally acceptable. Particularly needed are control agents that can target to a wider spectrum of economically important insect pests and that efficiently control insect strains that are or could become resistant to existing insect control agents.

SUMMARY

In view of these needs, it is an object of the present invention to provide new pest control agents by providing new *Bacillus thuringiensis* (Bt) isolates as well as novel genes and pesticidal proteins that may be used to control a variety of plant pests.

The invention provides compositions and methods for conferring pesticidal activity to bacteria, plants, plant cells, tissues and seeds. In particular, chimeric genes comprising novel polynucleotides that encode Cry proteins isolated from Bt and sequences substantially identical thereto, whose expression results in proteins with toxicity to economically important insect pests, particularly insect pests that infest plants, are provided. The invention is further drawn to the novel Cry proteins resulting from the expression of the polynucleotides, and to compositions and formulations containing the Cry proteins, which are toxic to insects by inhibiting the ability of insect pests to survive, grow and reproduce, or of limiting insect-related damage or loss to crop plants. Cry proteins of the invention include native Cry proteins and mutant or variant Cry proteins that have one or more amino acid substitutions, additions or deletions. Examples of mutant Cry proteins include without limitation those that are mutated to have a broader spectrum of activity or higher specific activity than their native Cry protein counterparts, those mutated to introduce an epitope to generate antibodies that differentially recognize the mutated protein from the native protein or those mutated to modulate expression in a transgenic organism. The novel Cry proteins of the invention are highly toxic to insect pests. For example, the Cry proteins of the invention can be used to control one or more economically important insect pests such as black cutworm (*Agrotis ipsilon*), European corn borer (*Ostrinia nubilalis*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (*Richia albicosta*), tobacco budworm (*Heliothis virescens*), Asian corn borer (*Ostrinia nubilalis*), cotton bollworm (*Helicoverpa armigera*), striped stem borer (*Chilo suppressalis*), pink stem borer (*Sesamia calamistis*), rice leaffolder (*Cnaphalocrocis medinalis*), and the like.

The invention also provides synthetic polynucleotides that encode the Cry proteins of the invention that have one or more codons optimized for expression in transgenic organisms such as transgenic bacteria or transgenic plants.

The invention is further drawn to expression cassettes and recombinant vectors comprising a polynucleotide that encodes a Cry protein of the invention. The invention also provides transformed bacteria, plants, plant cells, tissues, and seeds comprising a chimeric gene, or an expression cassette or a recombinant vector which are useful in expressing a Cry protein of the invention in the transformed bacteria, plants, plant cells, tissues and seeds.

The invention is also drawn to isolated *Bacillus thuringiensis* (Bt) strains that produce the Cry proteins of the invention. Such Bt strains may be a naturally occurring isolate or a recombinant Bt strain which produce one or more of the Cry proteins of the invention.

The invention is also drawn to methods of using polynucleotides of the invention, for example in DNA constructs or chimeric genes or expression cassettes or recombinant vectors for transformation and expression in organisms, including plants and microorganisms, such as bacteria. The nucleotide or amino acid sequences may be native or synthetic sequences that have been designed for expression in an organism such as a plant or bacteria or in making hybrid Cry toxins with enhanced pesticidal activity. The invention is further drawn to methods of making the Cry proteins and to methods of using the polynucleotide sequences and Cry proteins, for example in microorganisms to control insects or in transgenic plants to confer protection from insect damage.

Another aspect of the invention includes insecticidal compositions and formulations comprising the Cry proteins or *Bacillus thuringiensis* strains of the invention, and methods of using the compositions or formulations to control insect populations, for example by applying the compositions or formulations to insect-infested areas, or to prophylactically treat insect-susceptible areas or plants to confer protection against the insect pests. Optionally, the compositions or formulations of the invention may, in addition to the Cry protein or Bt strain of the invention, comprises other pesticidal agents such as chemical pesticides in order to augment or enhance the insect-controlling capability of the composition or formulation.

The compositions and methods of the invention are useful for controlling insect pests that attack plants, particularly crop plants. The compositions of the invention are also useful for generating altered or improved Cry proteins that have pesticidal activity, or for detecting the presence of a Cry protein or nucleic acids in commercial products or transgenic organisms.

These and other features, aspects, and advantages of the invention will become better understood with reference to the following detailed description and claims.

BRIEF DESCRIPTION OF THE SEQUENCES IN THE SEQUENCE LISTING

SEQ ID NO:1 is a nucleotide sequence encoding a BT-0016 protein.

SEQ ID NO:2 is a nucleotide sequence encoding a BT-0026 protein.

SEQ ID NO:3 is a nucleotide sequence encoding a BT-0032 protein.

SEQ ID NO:4 is a codon optimized sequence encoding a BT-0016 protein.

SEQ ID NO:5 is a codon optimized sequence encoding a BT-0026 protein.

SEQ ID NO:6 is a codon optimized sequence encoding a BT-0032 protein.

SEQ ID NO:7 is a nucleotide sequence encoding a mutant BT-0016 protein.

SEQ ID NO:8 is a nucleotide sequence encoding a mutant BT-0026 protein.

SEQ ID NO:9 is a nucleotide sequence encoding a mutant BT-0032 protein.

SEQ ID NO: 10 is an amino acid sequence of a BT-0016 protein.

SEQ ID NO: 11 is an amino acid sequence of a BT-0026 protein.

SEQ ID NO: 12 is an amino acid sequence of a BT-0032 protein.

SEQ ID NO: 13 is an amino acid sequence of a mutant BT-0016 protein.

SEQ ID NO: 14 is an amino acid sequence of a mutant BT-0026 protein.

SEQ ID NO: 15 is an amino acid sequence of a mutant BT-0032 protein.

SEQ ID NOs:16-17 are primer sequences useful in the invention.

DETAILED DESCRIPTION

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. Thus, the invention contemplates that in some embodiments of the invention, any feature or combination of features set forth herein can be excluded or omitted. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

Definitions

As used herein and in the appended claims, the singular forms "a," "and," and "the" include plural reference unless the context clearly dictates otherwise. Thus, for example, reference to "a plant" is a reference to one or more plants and includes equivalents thereof known to those skilled in the art, and so forth. As used herein, the word "or" means any one member of a particular list and also includes any combination of members of that list (i.e., includes also "and").

The term "about" is used herein to mean approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent, preferably 10 percent up or down (higher or lower). With regard to a temperature the term "about" means±1° C., preferably ±0.5° C. Where the term "about" is used in the context of this invention (e.g., in combinations with temperature or molecular weight values) the exact value (i.e., without "about") is preferred.

By "activity" of a toxic Cry protein of the invention is meant that the toxic protein functions as an orally active insect control agent, has a toxic effect, or is able to disrupt or deter insect feeding, which may or may not cause death of the insect. When a toxic protein of the invention is delivered to the insect, the result is typically death of the insect, or the insect does not feed upon the source that makes the toxic protein available to the insect.

As used herein, the term "amplified" means the construction of multiple copies of a nucleic acid molecule or multiple copies complementary to the nucleic acid molecule using at least one of the nucleic acid molecules as a template. Amplification systems include the polymerase chain reaction (PCR) system, ligase chain reaction (LCR) system, nucleic acid sequence based amplification (NASBA, Cangene, Mississauga, Ontario), Q-Beta Replicase systems, transcription-based amplification system (TAS), and strand displacement amplification (SDA). See, e.g., Diagnostic Molecular Microbiology: Principles and Applications, PERSING et al., Ed., American Society for Microbiology, Washington, D.C. (1993). The product of amplification is termed an "amplicon."

The term "chimeric construct" or "chimeric gene" or "chimeric polynucleotide" or "chimeric nucleic acid" (or similar terms) as used herein refers to a construct or molecule comprising two or more polynucleotides of different origin assembled into a single nucleic acid molecule. The term "chimeric construct", "chimeric gene", "chimeric polynucleotide" or "chimeric nucleic acid" refers to any construct or molecule that contains, without limitation, (1) polynucleotides (e.g., DNA), including regulatory and coding polynucleotides that are not found together in nature (i.e., at least one of the polynucleotides in the construct is heterologous with respect to at least one of its other polynucleotides), or (2) polynucleotides encoding parts of proteins not naturally adjoined, or (3) parts of promoters that are not naturally adjoined. Further, a chimeric construct, chimeric gene, chimeric polynucleotide or chimeric nucleic acid may comprise regulatory polynucleotides and coding polynucleotides that are derived from different sources, or comprise regulatory polynucleotides and coding polynucleotides derived from the same source, but arranged in a manner different from that found in nature. In some embodiments of the invention, the chimeric construct, chimeric gene, chimeric polynucleotide or chimeric nucleic acid comprises an expression cassette comprising a polynucleotide of the invention under the control of regulatory polynucleotides, particularly under the control of regulatory polynucleotides functional in plants or bacteria.

A "coding sequence" is a nucleic acid sequence that is transcribed into RNA such as mRNA, rRNA, tRNA, snRNA, sense RNA or antisense RNA. Preferably the RNA is then translated in an organism to produce a protein.

As used herein, a "codon optimized" sequence means a nucleotide sequence of a recombinant, transgenic, or synthetic polynucleotide wherein the codons are chosen to reflect the particular codon bias that a host cell or organism may have. This is typically done in such a way so as to preserve the amino acid sequence of the polypeptide encoded by the codon optimized nucleotide sequence. In certain embodiments, the DNA sequence of the recombinant DNA construct includes sequence that has been codon optimized for the cell (e.g., an animal, plant, or fungal cell) in which the construct is to be expressed. For example, a construct to be expressed in a plant cell can have all or parts of its sequence (e.g., the first gene suppression element or the gene expression element) codon optimized for expression in a plant. See, for example, U.S. Pat. No. 6,121,014, incorporated herein by reference.

To "control" insects means to inhibit, through a toxic effect, the ability of insect pests to survive, grow, feed, or reproduce, or to limit insect-related damage or loss in crop plants or to protect the yield potential of a crop when grown in the presence of insect pests. To "control" insects may or may not mean killing the insects, although it preferably means killing the insects.

The terms "comprises" or "comprising," when used in this specification, specify the presence of stated features, integers, steps, operations, elements, or components, but do not preclude the presence or addition of one or more other features, integers, steps, operations, elements, components, or groups thereof.

As used herein, the transitional phrase "consisting essentially of" (and grammatical variants) means that the scope of a claim is to be interpreted to encompass the specified materials or steps recited in the claim "and those that do not materially alter the basic and novel characteristic(s)" of the claimed invention. Thus, the term "consisting essentially of" when used in a claim of this invention is not intended to be interpreted to be equivalent to "comprising."

In the context of the invention, "corresponding to" or "corresponds to" means that when the amino acid sequences of variant or homolog Cry proteins are aligned with each other, the amino acids that "correspond to" certain enumerated positions in the variant or homolog protein are those that align with these positions in a reference protein but that are not necessarily in these exact numerical positions relative to the particular reference amino acid sequence of the invention. For example, if SEQ ID NO: 10 is the reference sequence and is aligned with SEQ ID NO:12, the Met623 of SEQ ID NO:12 "corresponds to" Met614 of SEQ ID NO:10.

As used herein, the term "Cry protein" means an insecticidal protein of a *Bacillus thuringiensis* crystal delta-endotoxin type. The term "Cry protein" can refer to the protoxin form or any insecticidally active fragment or toxin thereof.

To "deliver" a composition or toxic protein means that the composition or toxic protein comes in contact with an insect, which facilitates the oral ingestion of the composition or toxic protein, resulting in a toxic effect and control of the insect. The composition or toxic protein can be delivered in many recognized ways, including but not limited to, transgenic plant expression, formulated protein composition(s), sprayable protein composition(s), a bait matrix, or any other art-recognized protein delivery system.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide group.

"Effective insect-controlling amount" means that concentration of a toxic protein that inhibits, through a toxic effect, the ability of insects to survive, grow, feed or reproduce, or limits insect-related damage or loss in crop plants or protects the yield potential of a crop when grown in the presence of insect pests. "Effective insect-controlling amount" may or may not mean killing the insects, although it preferably means killing the insects.

"Expression cassette" as used herein means a nucleic acid molecule capable of directing expression of at least one polynucleotide of interest, such as a polynucleotide that encodes a Cry protein of the invention, in an appropriate host cell, comprising a promoter operably linked to the polynucleotide of interest which is operably linked to a termination signal. An "expression cassette" also typically comprises additional polynucleotides required for proper translation of the polynucleotide of interest. The expression cassette may also comprise other polynucleotides not necessary in the direct expression of a polynucleotide of interest but which are present due to convenient restriction sites for removal of the cassette from an expression vector. The expression cassette comprising the polynucleotide(s) of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e. the polynucleotide of interest in the expression cassette does not occur naturally in the host cell and must have been introduced into the host cell or an ancestor of the host cell by a transformation process or a breeding process. The expression of the polynucleotide(s) of interest in the expression cassette is generally under the control of a promoter. In the case of a multicellular organism, such as a plant, the promoter can also be specific or preferential to a particular tissue, or organ, or stage of development. An expression cassette, or fragment thereof, can also be referred to as "inserted polynucleotide" or "insertion polynucleotide" when transformed into a plant.

A "gene" is defined herein as a hereditary unit comprising one or more polynucleotides that occupies a specific location on a chromosome or plasmid and that contains the genetic instruction for a particular characteristic or trait in an organism.

A "gut protease" is a protease naturally found in the digestive tract of an insect. This protease is usually involved in the digestion of ingested proteins. Examples of gut proteases include trypsin, which typically cleaves peptides on the C-terminal side of lysine (K) or arginine (R) residues, and chymotrypsin, which typically cleaves peptides on the C-terminal side of phenylalanine (F), tryptophan (W) or tyrosine (Y).

The term "heterologous" when used in reference to a gene or a polynucleotide or a polypeptide refers to a gene or a polynucleotide or a polypeptide that is or contains a part thereof not in its natural environment (i.e., has been altered by the hand of man). For example, a heterologous gene may include a polynucleotide from one species introduced into another species. A heterologous gene may also include a polynucleotide native to an organism that has been altered in some way (e.g., mutated, added in multiple copies, linked to a non-native promoter or enhancer polynucleotide, etc.). Heterologous genes further may comprise plant gene polynucleotides that comprise cDNA forms of a plant gene; the cDNAs may be expressed in either a sense (to produce mRNA) or anti-sense orientation (to produce an anti-sense RNA transcript that is complementary to the mRNA transcript). In one aspect of the invention, heterologous genes are distinguished from endogenous plant genes in that the heterologous gene polynucleotide are typically joined to polynucleotides comprising regulatory elements such as promoters that are not found naturally associated with the gene for the protein encoded by the heterologous gene or with plant gene polynucleotide in the chromosome, or are associated with portions of the chromosome not found in nature (e.g., genes expressed in loci where the gene is not normally expressed). Further, a "heterologous" polynucleotide refers to a polynucleotide not naturally associated with a host cell into which it is introduced, including non-naturally occurring multiple copies of a naturally occurring polynucleotide.

"Homologous recombination" is the exchange ("crossing over") of DNA fragments between two DNA molecules or chromatids of paired chromosomes in a region of identical polynucleotides. A "recombination event" is herein understood to mean a meiotic crossing-over.

A nucleic acid sequence is "isocoding" with a reference nucleic acid sequence when the nucleic acid sequence encodes a polypeptide having the same amino acid sequence as the polypeptide encoded by the reference nucleic acid sequence. For example, SEQ ID NO:4 is isocoding with SEQ ID NO: 1 because they both encode the amino acid sequence represented by SEQ ID NO: 10.

The term "isolated" nucleic acid molecule, polynucleotide or protein is a nucleic acid molecule, polynucleotide or protein that no longer exists in its natural environment. An isolated nucleic acid molecule, polynucleotide or protein of the invention may exist in a purified form or may exist in a recombinant host such as in a transgenic bacteria or a transgenic plant.

A "nucleic acid molecule" is single- or double-stranded DNA or RNA that can be isolated from any source. In the context of the present invention, the nucleic acid molecule is preferably a segment of DNA.

"Operably linked" refers to the association of polynucleotides on a single nucleic acid fragment so that the function of one affects the function of the other. For example, a promoter is operably linked with a coding polynucleotide or functional RNA when it is capable of affecting the expression of that coding polynucleotide or functional RNA (i.e., that the coding polynucleotide or functional RNA is under the transcriptional control of the promoter). Coding polynucleotide in sense or antisense orientation can be operably linked to regulatory polynucleotides.

As used herein "pesticidal," insecticidal," and the like, refer to the ability of a Cry protein of the invention to control a pest organism or an amount of a Cry protein that can control a pest organism as defined herein. Thus, a pesticidal Cry protein can kill or inhibit the ability of a pest organism (e.g., insect pest) to survive, grow, feed, or reproduce.

A "plant" is any plant at any stage of development, particularly a seed plant.

A "plant cell" is a structural and physiological unit of a plant, comprising a protoplast and a cell wall. The plant cell may be in the form of an isolated single cell or a cultured cell, or as a part of a higher organized unit such as, for example, plant tissue, a plant organ, or a whole plant.

"Plant cell culture" means cultures of plant units such as, for example, protoplasts, cell culture cells, cells in plant tissues, pollen, pollen tubes, ovules, embryo sacs, zygotes and embryos at various stages of development.

"Plant material" refers to leaves, stems, roots, flowers or flower parts, fruits, pollen, egg cells, zygotes, seeds, cuttings, cell or tissue cultures, or any other part or product of a plant.

A "plant organ" is a distinct and visibly structured and differentiated part of a plant such as a root, stem, leaf, flower bud, or embryo.

"Plant tissue" as used herein means a group of plant cells organized into a structural and functional unit. Any tissue of a plant in planta or in culture is included. This term includes, but is not limited to, whole plants, plant organs, plant seeds, tissue culture and any groups of plant cells organized into structural or functional units. The use of this term in conjunction with, or in the absence of, any specific type of plant tissue as listed above or otherwise embraced by this definition is not intended to be exclusive of any other type of plant tissue.

A "polynucleotide" refers to a polymer composed of many nucleotide monomers covalently bonded in a chain. Such "polynucleotides" includes DNA, RNA, modified oligo nucleotides (e.g., oligonucleotides comprising bases that are not typical to biological RNA or DNA, such as 2'-O-methylated oligonucleotides), and the like. In some embodiments, a nucleic acid or polynucleotide can be single-stranded, double-stranded, multi-stranded, or combinations thereof. Unless otherwise indicated, a particular nucleic acid or polynucleotide of the present invention optionally comprises or encodes complementary polynucleotides, in addition to any polynucleotide explicitly indicated.

"Polynucleotide of interest" refers to any polynucleotide which, when transferred to an organism, e.g., a plant, confers upon the organism a desired characteristic such as insect resistance, disease resistance, herbicide tolerance, antibiotic resistance, improved nutritional value, improved performance in an industrial process, production of commercially valuable enzymes or metabolites or altered reproductive capability.

The term "promoter" refers to a polynucleotide, usually upstream (5') of its coding polynucleotide, which controls the expression of the coding polynucleotide by providing the recognition for RNA polymerase and other factors required for proper transcription.

A "protoplast" is an isolated plant cell without a cell wall or with only parts of the cell wall.

As used herein, the term "recombinant" refers to a form of nucleic acid (e.g., DNA or RNA) or protein or an organism that would not normally be found in nature and as such was created by human intervention. As used herein, a "recombinant nucleic acid molecule" is a nucleic acid molecule comprising a combination of polynucleotides that would not naturally occur together and is the result of human intervention, e.g., a nucleic acid molecule that is comprised of a combination of at least two polynucleotides heterologous to each other, or a nucleic acid molecule that is artificially synthesized and comprises a polynucleotide that deviates from the polynucleotide that would normally exist in nature, or a nucleic acid molecule that comprises a transgene artificially incorporated into a host cell's genomic DNA and the associated flanking DNA of the host cell's genome. An example of a recombinant nucleic acid molecule is a DNA molecule resulting from the insertion of a transgene into a plant's genomic DNA, which may ultimately result in the expression of a recombinant RNA or protein molecule in that organism. As used herein, a "recombinant plant" is a plant that would not normally exist in nature, is the result of human intervention, and contains a transgene or heterologous nucleic acid molecule incorporated into its genome. As a result of such genomic alteration, the recombinant plant is distinctly different from the related wild-type plant.

"Regulatory elements" refer to sequences involved in controlling the expression of a nucleotide sequence. Regulatory elements comprise a promoter operably linked to the nucleotide sequence of interest and termination signals. They also typically encompass sequences required for proper translation of the nucleotide sequence.

The term "identity" or "identical" or "substantially identical," in the context of two nucleic acid or amino acid sequences, refers to two or more sequences or subsequences that have at least 60%, preferably at least 80%, more preferably at least 90%, even more preferably at least 95%, and most preferably at least 99% nucleotide or amino acid residue identity, when compared and aligned for maximum correspondence, as measured using one of the following sequence comparison algorithms or by visual inspection. Preferably, the substantial identity exists over a region of the sequences that is at least about 50 residues or bases in length, more preferably over a region of at least about 100 residues or bases, and most preferably the sequences are substantially identical over at least about 150 residues or bases. In an especially preferred embodiment, the sequences are substantially identical over the entire length of the coding regions. Furthermore, substantially identical nucleic acid or amino acid sequences perform substantially the same function.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2: 482 (1981), by the homology alignment algorithm of Needleman & Wunsch, J. Mol. Biol. 48: 443 (1970), by the search for similarity method of Pearson & Lipman, Proc. Nat'l. Acad Sci. USA 85: 2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, Ausubel et al., infra).

One example of an algorithm that is suitable for determining percent sequence identity and sequence similarity is the BLAST algorithm, which is described in Altschul et al., J. Mol. Biol. 215: 403-410 (1990). Software for performing BLAST analyses is publicly available through the National Center for Biotechnology Information (National Center for Biotechnology Information, U.S. National Library of Medicine, 8600 Rockville Pike, Bethesda, Md. 20894 USA). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, Proc. Natl. Acad Sci. USA 89: 10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90: 5873-5787 (1993)). One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

Another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) Laboratory Techniques in Biochemistry and Molecular Biology-Hybridization with Nucleic Acid Probes part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but not to other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.15M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone homologous nucleotide sequences that are substantially identical to reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

A further indication that two nucleic acid sequences or proteins are substantially identical is that the protein encoded by the first nucleic acid is immunologically cross reactive with, or specifically binds to, the protein encoded by the second nucleic acid. Thus, a protein is typically substantially identical to a second protein, for example, where the two proteins differ only by conservative substitutions.

"Synthetic" refers to a nucleotide sequence comprising bases or structural features that are not present in the natural sequence. For example, an artificial sequence encoding a Cry protein of the invention that resembles more closely the G+C content and the normal codon distribution of dicot or monocot plant genes is said to be synthetic.

As used herein, a Cry protein that is "toxic" to an insect pest is meant that the Cry protein functions as an orally active insect control agent to kill the insect pest, or the Cry protein is able to disrupt or deter insect feeding, or causes growth inhibition to the insect pest, both of which may or may not cause death of the insect. When a Cry protein of the invention is delivered to an insect or an insect comes into oral contact with the Cry protein, the result is typically death of the insect, or the insect's growth is slowed, or the insect stops feeding upon the source that makes the toxic Cry protein available to the insect.

"Transformation" is a process for introducing heterologous nucleic acid into a host cell or organism. In particular, "transformation" means the stable integration of a DNA molecule into the genome of an organism of interest.

"Transformed/transgenic/recombinant" refer to a host organism such as a bacterium or a plant into which a heterologous nucleic acid molecule has been introduced. The nucleic acid molecule can be stably integrated into the genome of the host or the nucleic acid molecule can also be present as an extrachromosomal molecule. Such an extrachromosomal molecule can be auto-replicating. Transformed cells, tissues, or plants are understood to encompass not only the end product of a transformation process, but also transgenic progeny thereof. A "non-transformed", "non-transgenic", or "non-recombinant" host refers to a wild-type organism, e.g., a bacterium or plant, which does not contain the heterologous nucleic acid molecule.

Nucleotides are indicated by their bases by the following standard abbreviations: adenine (A), cytosine (C), thymine (T), and guanine (G). Amino acids are likewise indicated by the following standard abbreviations: alanine (Ala; A), arginine (Arg; R), asparagine (Asn; N), aspartic acid (Asp; D), cysteine (Cys; C), glutamine (Gln; Q), glutamic acid (Glu; E), glycine (Gly; G), histidine (His; H), isoleucine (Ile; 1), leucine (Leu; L), lysine (Lys; K), methionine (Met; M), phenylalanine (Phe; F), proline (Pro; P), serine (Ser; S), threonine (Thr; T), tryptophan (Trp; W), tyrosine (Tyr; Y), and valine (Val; V).

This invention provides compositions and methods for controlling harmful plant pests. Particularly, the invention relates to Cry proteins that may be isolated from bacteria, such as *Bacillus thuringiensis*, that are toxic to insect pests and to polynucleotides that comprise nucleotide sequences that encode the Cry proteins, and to the making and using of the polynucleotides and Cry proteins to control insect pests.

According to some embodiments, the invention provides a nucleic acid molecule or optionally an isolated nucleic acid molecule comprising a nucleotide sequence encoding a Cry protein in its protoxin form or a biologically active or toxin fragment thereof, wherein the nucleotide sequence (a) has at least 80% to at least 99% sequence identity with any of SEQ ID NOs: 1-3 or a toxin-encoding fragment thereof; or (b) encodes a protein comprising an amino acid sequence that has at least 80% to at least 99% sequence identity with any of SEQ ID NOs:10-12 or a toxin fragment thereof; or (c) is a synthetic sequence of (a) or (b) that has codons optimized for expression in a transgenic organism. In other embodiments, the nucleotide sequence comprises any of SEQ ID NOs: 1-3 or any toxin-encoding fragments of any of SEQ ID NOs: 1-3. In other embodiments, the synthetic nucleotide sequence comprises any of SEQ ID NOs:4-9 or any toxin-encoding fragments of any of SEQ ID NOs:4-9.

Polynucleotides that are fragments of Cry protein protoxin-encoding polynucleotides are also encompassed by the invention. By "fragment" is intended a portion of the nucleotide sequence encoding a Cry protein. A fragment of a nucleotide sequence may encode a biologically active portion of a Cry protein, the so called "toxin fragment," or it may be a fragment that can be used as a hybridization probe or PCR primer using methods disclosed below. Nucleic acid molecules that are fragments of a Cry protein encoding nucleotide sequence comprise at least about 15, 20, 50, 75, 100, 200, 300, 350, 400, 450, 500, 550, 600, 650, 700, 750, 800, 850, 900, 950, 1000, 1050, 1100, 1150, 1200, 1250, 1300, 1350, 1400, 1450 contiguous nucleotides, or up to the number of nucleotides present in a full-length Cry protein encoding nucleotide sequence disclosed herein (for example, 1875 nucleotides for SEQ ID NO: 1) depending upon the intended use. By "contiguous" nucleotides is intended nucleotide residues that are immediately adjacent to one another. Some fragments of the nucleotide sequences of the invention will encode toxin fragments that retain the biological activity of the Cry protein and, hence, retain insecticidal activity. By "retains insecticidal activity" is intended that the fragment will have at least about 30%, preferably at least about 50%, more preferably at least about 70%, even more preferably at least about 80% of the insecticidal activity of the Cry protein. Methods for measuring insecticidal activity are well known in the art. See, for example, Czapla and Lang (1990) J. Econ. Entomol. 83:2480-2485; Andrews et al. (1988) Biochem. J. 252:199-206; Marrone et al. (1985) J. of Economic Entomology 78:290-293; and U.S. Pat. No. 5,743,477, all of which are herein incorporated by reference in their entirety.

A toxin fragment of a Cry protein of the invention will encode at least about 15, 25, 30, 50, 75, 100, 125, 150, 175, 200, 250, 300, 350, 400, and 450 contiguous amino acids, or up to the total number of amino acids present in a full-length Cry protein of the invention (for example, 623 amino acids for SEQ ID NO:10).

In some embodiments, a nucleic acid molecule of the invention comprises, consists essentially of or consists of a nucleotide sequence encoding a Cry protein comprising an amino acid sequence that has at least 80% to at least 99% sequence identity with any of SEQ ID NOs:10-12 or a toxin fragment thereof. In some other embodiments, the amino acid sequence comprises, consists essentially of or consists of any of SEQ ID NOs:10-12 or a toxin fragment thereof. Thus, in some embodiments, Cry proteins which have been activated by means of proteolytic processing, for example, by proteases prepared from the gut of an insect, may be characterized and the N-terminal or C-terminal amino acids of the activated toxin fragment identified. In this aspect of the invention, the skilled person can determine that, for example, the toxin fragment of SEQ ID NO: 10 likely comprises amino acids from about 43 to about 623 or from about 44 to about 623 of SEQ ID NO: 10, or the toxin fragment of SEQ ID NO: 11 likely comprises amino acids from about amino acid 41 to about 598 or from about 41 to about 631 or from about 42 to about 631 or from about 42 to 631 of SEQ ID NO: 11, or the toxin fragment of SEQ ID NO: 12 likely comprises amino acids from about amino acid 42 to about 585 or from about 42 to about 633 or from about amino acid 43 to about 585 or from about 43 to about 633 of SEQ ID NO: 12. Cry protein variants produced by introduction or elimination of protease processing sites at appropriate positions in the coding sequence to allow, or eliminate, proteolytic cleavage of a larger variant protein by insect, plant or microorganism proteases are also within the scope of the invention. The end result of such manipulation is understood to be the generation of toxin fragment molecules having the same or better activity as the intact Cry protoxin protein.

In some embodiments of the invention, a chimeric gene is provided that comprises a heterologous promoter operably linked to a polynucleotide comprising, consisting essentially of or consisting of a nucleotide sequence that encodes a Cry protein toxic to a lepidopteran pest, wherein the nucleotide sequence (a) has at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%) to at least 99% (99%, 99.1%, 99.2%, 99.3%, 99.4%, 99.5%, 99.6%, 99.7%, 99.8%, 99.9%) sequence identity with any one of SEQ ID NOs: 1-3, or a toxin-encoding fragment thereof; or (b) encodes a protein comprising an amino acid sequence that has at least 80% (e.g., 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%) to at least 99% (99%, 99.1%, 99.2%, 99.3%, 99.4%, 99.5%, 99.6%, 99.7%, 99.8%, 99.9%) sequence identity with any one of SEQ ID NOs:10-12, or a toxin fragment thereof; or (c) is a synthetic sequence of (a) or (b) that has codons optimized for expression in a transgenic organism.

In other embodiments, the heterologous promoter is a plant-expressible promoter. For example, without limitation, the plant-expressible promoter can be selected from the group of promoters consisting of ubiquitin, cestrum yellow virus, corn TrpA, OsMADS 6, maize H3 histone, bacteriophage T3 gene 9 5' UTR, corn sucrose synthetase 1, corn alcohol dehydrogenase 1, corn light harvesting complex, corn heat shock protein, maize mtl, pea small subunit RuBP carboxylase, rice actin, rice cyclophilin, Ti plasmid mannopine synthase, Ti plasmid nopaline synthase, *petunia* chalcone isomerase, bean glycine rich protein 1, potato patatin, lectin, CaMV 35S and S-E9 small subunit RuBP carboxylase promoter.

In additional embodiments, the protein encoded by the chimeric gene is toxic to one or more lepidopteran pests selected from the group consisting of European corn borer (*Ostrinia nubilalis*), black cutworm (*Agrotis ipsilon*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (Richia albicosta), tobacco budworm (*Heliothis virescens*), Asian corn borer (*Ostrinia nubilalis*), cotton bollworm (*Helicoverpa armigera*), striped stem borer (*Chilo suppressalis*), pink stem borer (*Sesamia calamistis*) and rice leaffolder (*Cnaphalocrocis medinalis*).

In further embodiments, the polynucleotide comprises, consists essentially of or consists of a nucleotide sequence that has at least 80% to at least 99% sequence identity with SEQ ID NO: 1, or a toxin-encoding fragment thereof, or has at least 80% to at least 99% sequence identity with SEQ ID NO:2, or a toxin-encoding fragment thereof, or has at least 80% to at least 99% sequence identity with SEQ ID NO:3, or a toxin-encoding fragment thereof.

In other embodiments, the polynucleotide comprises, consists essentially of or consists of any one of SEQ ID NOs: 1-3, or a toxin-encoding fragment thereof.

In other embodiments, the polynucleotide comprises, consists essentially of or consists of a nucleotide sequence that encodes a protein comprising, consisting essentially of or consisting of an amino acid sequence that has at least 80% to at least 99% sequence identity with any one of SEQ ID NOS: 10-12, or a toxin fragment thereof.

In still other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO: 10, or a toxin fragment thereof.

In further embodiments, the amino acid sequence has at least 80%, or at least 81%, or at least 82%, or at least 83%, or at least 84%, or at least 85%, or at least 86%, or at least 87%, or at least 88%, or at least 89% at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:11, or a toxin fragment thereof.

In still further embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO: 12, or a toxin fragment thereof.

In some embodiments, the chimeric gene of the invention comprises a polynucleotide comprising a synthetic sequence of a nucleotide sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% with any of SEQ ID NOS:4-9, wherein the synthetic sequence has codons optimized for expression is a transgenic organism. In other embodiments, the chimeric gene of the invention comprises a polynucleotide comprising a synthetic sequence of a nucleotide sequence that encodes a protein comprising an amino acid sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any of SEQ ID NOS: 10-15, or a toxin fragment thereof, wherein the synthetic sequence has codons optimized for expression is a transgenic organism. In further embodiments, the transgenic organism is a transgenic bacteria or a transgenic plant.

In some embodiments, the invention provides a synthetic polynucleotide comprising, consisting essentially of or consisting of a nucleotide sequence that encodes a protein that is toxic to a lepidopteran pest, wherein the nucleotide sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any one of SEQ ID NOS:4-9, or a toxin-encoding fragment thereof.

In other embodiments, the invention provides a synthetic polynucleotide comprising, consisting essentially of or consisting of a nucleotide sequence that encodes a protein that is toxic to a lepidopteran pest, wherein the nucleotide sequence encodes an amino acid sequence that has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with any one of SEQ ID NOS: 10-15, or a toxin fragment thereof.

Cry proteins of the invention may be isolated from certain *Bacillus thuringiensis* (Bt) strains such as C0633, C0724 and C1100. It will be recognized that Cry proteins of the invention may also be isolated from other Bt strains and that such Bt strains can be isolated by standard techniques and tested for toxicity to a lepidopteran pest of the invention. Generally Bt strains can be isolated from any environmental sample, including soil, plant, insect, grain elevator dust, and other sample material, etc., by methods known in the art. See, for example, Travers et al. (1987) Appl. Environ. Microbiol. 53:1263-1266; Saleh et al. (1969) Can J. Microbiol. 15:1101-1104; DeLucca et al. (1981) Can J. Microbiol. 27:865-870; and Norris, et al. (1981) "The genera *Bacillus* and *Sporolactobacillus*," In Starr et al. (eds.), The Prokaryotes: A Handbook on Habitats, Isolation, and Identification of Bacteria, Vol. II, Springer-Verlog Berlin Heidelberg. After isolation, Bt strains can be tested for toxicity to a lepidopteran pest and Cry proteins encompassed by the invention can be identified. Therefore, in some embodiments, the invention provides an isolated *Bacillus thuringiensis* (Bt) strain that produces a Cry protein or a recombinant Cry protein comprising, consisting essentially of or consisting of an amino acid sequence having at least 80% to at least 99% sequence identity to any of SEQ ID NOs: 10-12. In other embodiments, the Bt strain is selected from the group consisting of C0633, C0724 and C1100. In still further embodiments, the Cry protein or recombinant Cry protein comprises, consists essentially of or consists of any of SEQ ID NOs:10-12.

According to some embodiments, the invention provides an optionally isolated Cry protein that is toxic to a lepidopteran pest, wherein the protein comprises, consists essentially of or consists of (a) an amino acid sequence that has at least 80% sequence identity to at least 99% sequence identity with an amino acid sequence represented by any one of SEQ ID NOs:10-15, or a toxin fragment thereof; or (b) an amino acid sequence that is encoded by a nucleotide sequence that has at least 80% sequence identity to at least 99% sequence identity with a nucleotide sequence represented by any one of SEQ ID NOs:4-9, or a toxin-encoding fragment thereof.

In other embodiments, the optionally isolated Cry protein comprises, consists essentially of or consists of an amino acid sequence that has at least 80% to at least 99% sequence identity with any one of SEQ ID NOS: 10-15., or a toxin fragment thereof. In still other embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO: 10, or a toxin fragment thereof.

In further embodiments, the amino acid sequence has at least 80%, or at least 81%, or at least 82%, or at least 83%, or at least 84%, or at least 85%, or at least 86%, or at least 87%, or at least 88%, or at least 89% at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO: 11, or a toxin fragment thereof.

In still further embodiments, the amino acid sequence has at least 90%, or at least 91%, or at least 92%, or at least 93%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO: 12, or a toxin fragment thereof.

In some embodiments, the amino acid sequence comprises, consists essentially of or consists of any one of SEQ ID NOs:10-15, or a toxin fragment thereof. In other embodiments, the amino acid sequence is encoded by a nucleotide sequence comprising, consisting essentially of or consisting of any of SEQ ID NOs: 1-3, or a toxin-encoding fragment thereof.

In other embodiments, the Cry proteins of the invention are toxic to a lepidopteran pest selected from the group consisting of European corn borer (*Ostrinia nubilalis*), black cutworm (*Agrotis ipsilon*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (Richia albicosta), tobacco budworm (*Heliothis virescens*), Asian corn borer (*Ostrinia nubilalis*), cotton bollworm (*Helicoverpa armigera*), striped stem borer (*Chilo suppressalis*), pink stem borer (*Sesamia calamistis*) and rice leaffolder (*Cnaphalocrocis medinalis*).

In some embodiments, the invention encompasses a recombinant Cry protein that is toxic to a lepidopteran pest, wherein the recombinant Cry protein comprises, consists essentially of or consists of (a) an amino acid sequence that has at least 80% to at least 99% sequence identity with an amino acid sequence represented by any of SEQ ID NOs: 10-15, or a toxin fragment thereof; or (b) an amino acid sequence that is encoded by a nucleotide sequence that has at 80% to at least 99% sequence identity with a nucleotide sequence represented by any of SEQ ID NOs:4-9, or a toxin-encoding fragment thereof.

In other embodiments, the recombinant Cry protein comprises, consists essentially of or consists of an amino acid sequence that has at least 80% to at least 99% sequence identity with any one of SEQ ID NOs:10-15, or a toxin fragment thereof. In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 93%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:10, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO: 11, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO: 12, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO:13, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO: 14, or a toxin fragment thereof.

In still other embodiments, the amino acid sequence has at least 80%, or at least 81%, or at least 82%, or at least 83%, or at least 84%, or at least 85%, or at least 86%, or at least 87%, or at least 88%, or at least 89%, or at least 90%, or at least 91%, or at least 92%, or at least 94%, or at least 94%, or at least 95%, or at least 96%, or at least 97%, or at least 98%, or at least 99%, or at least 99.1%, or at least 99.2%, or at least 99.3%, or at least 99.4%, or at least 99.5% or at least 99.6%, or at least 99.7%, or at least 99.8%, or at least 99.9% sequence identity with SEQ ID NO: 15, or a toxin fragment thereof.

In still further embodiments, the recombinant Cry protein comprises, consists essentially of or consists of an amino acid sequence of any of SEQ ID NOs: 10-15, or a toxin fragment thereof. In other embodiments, the recombinant Cry protein is encoded by a nucleotide sequence that comprises, consists essentially of or consists of any of SEQ ID NOs:4-9, or a toxin-encoding fragment thereof.

Antibodies raised in response to immune challenge by a native or mutant BT-0016, BT-0026 and BT-0032 and the like or related Cry proteins are also encompassed by the invention. Such antibodies may be produced using standard immunological techniques for production of polyclonal antisera and, if desired, immortalizing the antibody-producing cells of the immunized host for sources of monoclonal antibody production. Techniques for producing antibodies to any substance of interest are well known, e.g., as in Harlow and Lane (1988. Antibodies a laboratory manual. pp. 726. Cold Spring Harbor Laboratory) and as in Goding (Monoclonal Antibodies: Principles & practice.1986. Academic Press, Inc., Orlando, Fla.). The present invention encompasses insecticidal proteins that cross-react with antibodies, particularly monoclonal antibodies, raised against one or more of the insecticidal Cry proteins of the present invention.

The antibodies produced in the invention are also useful in immunoassays for determining the amount or presence of a native or mutant BT-0016, BT-0026 and BT-0032 or related Cry protein in a biological sample. Such assays are also useful in quality-controlled production of compositions containing one or more of the Cry proteins of the invention or related toxic proteins. In addition, the antibodies can be used to assess the efficacy of recombinant production of one or more of the Cry proteins of the invention or a related protein, as well as for screening expression libraries for the presence of a nucleotide sequence encoding one or more of the Cry proteins of the invention or related protein coding sequences. Antibodies are useful also as affinity ligands for purifying or isolating any one or more of the proteins of the invention and related proteins. The Cry proteins of the invention and proteins containing related antigenic epitopes may be obtained by over expressing full or partial lengths of a sequence encoding all or part of a Cry protein of the invention or a related protein in a preferred host cell.

It is recognized that DNA sequences that encode a native Cry protein of the invention may be altered by various methods, and that these alterations may result in DNA sequences encoding proteins with amino acid sequences different than that encoded by a native Cry protein of the invention. A Cry protein may be altered in various ways to make a mutant Cry protein including amino acid substitutions, deletions, truncations, and insertions of one or more amino acids of any of SEQ ID NOs:10-12, including up to about 2, about 3, about 4, about 5, about 6, about 7, about 8, about 9, about 10, about 15, about 20, about 25, about 30, about 35, about 40, about 45, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions. Methods for such manipulations are generally known in the art. For example, amino acid sequence variants of a native Cry protein can be prepared by mutations in a polynucleotide that encodes the protein. This may also be accomplished by one of several forms of mutagenesis or in directed evolution. In some aspects, the changes encoded in the amino acid sequence will not substantially affect the function of the protein. Such variants will possess the desired insecticidal activity. In some embodiments of the invention, nucleotide sequences represented by SEQ ID NOs: 1-3 are altered to introduce amino acid substitutions in the encoded protein. In other embodiments, the resulting mutant protein is encoded by a synthetic mutant polynucleotide comprising a nucleotide sequence represented by any one of SEQ ID NOs:7-9. In other embodiments, the mutant proteins comprise, consist essentially of or consist of an amino acid sequence represented by any one of SEQ ID NOs:13-15.

It is understood that the ability of an insecticidal protein to confer insecticidal activity may be improved by the use of such techniques upon the compositions of this invention. For example, one may express a Cry protein in host cells that exhibit high rates of base mis-incorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the Cry protein mutations in a non-mutagenic strain, and identify mutated genes with insecticidal activity, for example by performing an assay to test for insecticidal activity. Generally, the protein is mixed and used in feeding assays. See, for example Marrone et al. (1985) J. of Economic Entomology 78:290-293. Such assays can include contacting plants with one or more pests and determining the plant's ability to survive or cause the death of the pests. Examples of mutations that result in increased toxicity are found in Schnepf et al. (1998) Microbiol. Mol. Biol. Rev. 62:775-806.

Alternatively, alterations may be made to an amino acid sequence of the invention at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

A Cry protein of the invention can also be mutated to introduce an epitope to generate antibodies that recognize the mutated protein. Therefore, in some embodiments, the invention provides a mutated Cry protein, wherein an amino acid substitution in a native Cry protein produces a mutant Cry protein having an antigenic region that allows the mutant Cry protein to be distinguished from the native Cry protein in a protein detection assay.

In some embodiments, the invention provides a method of making an antibody that differentially recognizes a mutated Cry protein from the native Cry protein from which the mutated Cry protein is derived, the method comprising the steps of substituting amino acids in an antigenic loop of a native Cry protein and raising antibodies that specifically recognize the mutated antigenic loop in the mutated Cry protein and does not recognize the native Cry protein. In one embodiment, the antigenic loop is identified in non-conserved regions outside of domain I of the native Cry protein. In another embodiment, the antigenic loop is not a loop involved in the Cry protein's insect gut receptor recognition or involved in the protease activation of the Cry protein.

Variant nucleotide and amino acid sequences of the invention also encompass sequences derived from mutagenic and recombinogenic procedures such as DNA shuffling. With such a procedure, one or more different toxic protein coding regions can be used to create a new toxic protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) Proc. Natl. Acad. Sci. USA 91:10747-10751; Stemmer (1994) Nature 370:389-391; Crameri et al. (1997) Nature Biotech. 15:436-438; Moore et al. (1997) J. Mol. Biol. 272:336-347; Zhang et al. (1997) Proc. Natl. Acad. Sci. USA 94:4504-4509; Crameri et al. (1998) Nature 391:288-291; and U.S. Pat. Nos. 5,605,793 and 5,837,458.

Domain swapping or shuffling is another mechanism for generating altered Cry proteins of the invention. Domains may be swapped between Cry proteins, resulting in hybrid or chimeric toxic proteins with improved pesticidal activity or target spectrum. Methods for generating recombinant proteins and testing them for pesticidal activity are well known in the art (see, for example, Naimov et al. (2001) Appl. Environ. Microbiol. 67:5328-5330; de Maagd et al. (1996) Appl. Environ. Microbiol. 62:1537-1543; Ge et al. (1991) J. Biol. Chem. 266:17954-17958; Schnepf et al. (1990) J. Biol. Chem. 265:20923-20930; Rang et al. 91999) Appl. Environ. Microbiol. 65:2918-2925). In some embodiments, the invention provides hybrid Cry proteins comprising at a C-terminus, amino acids from a first Cry protein of the invention and at an N-terminus, amino acids from a second Cry protein of the invention different from the first Cry protein of the invention.

In some embodiments, the invention provides a recombinant vector comprising a polynucleotide, a nucleic acid molecule, an expression cassette or a chimeric gene of the invention. In other embodiments, the vector is further defined as a plasmid, cosmid, phagemid, artificial chromosome, phage or viral vector. Certain vectors for use in transformation of plants and other organisms are known in the art.

Thus, some embodiments of the invention are directed to expression cassettes designed to express the polynucleotides and nucleic acid molecules of the invention. As used herein, "expression cassette" means a nucleic acid molecule having at least a control sequence operatively linked to a nucleotide sequence of interest. In this manner, for example, plant promoters operably linked to the nucleotide sequences to be expressed are provided in expression cassettes for expression in a plant, plant part or plant cell.

An expression cassette comprising a polynucleotide of interest may be chimeric, meaning that at least one of its components is heterologous with respect to at least one other of its other components. An expression cassette may also be one that is naturally occurring but has been obtained in a recombinant form useful for heterologous expression. Typically, however, the expression cassette is heterologous with respect to the host, i.e., the particular nucleic acid sequence of the expression cassette does not occur naturally in the host cell and must have been introduced into the host cell or an ancestor of the host cell by a transformation event.

In addition to the promoters operatively linked to the nucleotide sequences of the invention, an expression cassette of this invention also can include other regulatory sequences. As used herein, "regulatory sequences" means nucleotide sequences located upstream (5' non-coding sequences), within or downstream (3' non-coding sequences) of a coding sequence, and which influence the transcription, RNA processing or stability, or translation of the associated coding sequence. Regulatory sequences include, but are not limited to, enhancers, introns, translation leader sequences, termination signals, and polyadenylation signal sequences.

In some embodiments, an expression cassette of the invention also can include polynucleotides that encode other desired traits in addition to the Cry proteins of the invention. Such expression cassettes comprising the stacked traits may be used to create plants, plant parts or plant cells having a desired phenotype with the stacked traits (i.e., molecular stacking). Such stacked combinations in plants can also be created by other methods including, but not limited to, cross breeding plants by any conventional methodology. If stacked by genetically transforming the plants, the nucleotide sequences of interest can be combined at any time and in any order. For example, a transgenic plant comprising one or more desired traits can be used as the target to introduce further traits by subsequent transformation. The additional nucleotide sequences can be introduced simultaneously in a co-transformation protocol with a nucleotide sequence, nucleic acid molecule, nucleic acid construct, or composition of this invention, provided by any combination of expression cassettes. For example, if two nucleotide sequences will be introduced, they can be incorporated in separate cassettes (trans) or can be incorporated on the same cassette (cis). Expression of polynucleotides can be driven by the same promoter or by different promoters. It is further recognized that polynucleotides can be stacked at a desired genomic location using a site-specific recombination system. See, e.g., Int'l Patent Application Publication Nos. WO 99/25821; WO 99/25854; WO 99/25840; WO 99/25855 and WO 99/25853.

The expression cassette also can include an additional coding sequence for one or more polypeptides or double stranded RNA molecules (dsRNA) of interest for agronomic traits that primarily are of benefit to a seed company, grower or grain processor. A polypeptide of interest can be any polypeptide encoded by a nucleotide sequence of interest. Non-limiting examples of polypeptides of interest that are suitable for production in plants include those resulting in agronomically important traits such as herbicide resistance (also sometimes referred to as "herbicide tolerance"), virus resistance, bacterial pathogen resistance, insect resistance, nematode resistance, or fungal resistance. See, e.g., U.S. Pat. Nos. 5,569,823; 5,304,730; 5,495,071; 6,329,504; and 6,337,431. The polypeptide also can be one that increases plant vigor or yield (including traits that allow a plant to grow at different temperatures, soil conditions and levels of sunlight and precipitation), or one that allows identification of a plant exhibiting a trait of interest (e.g., a selectable marker, seed coat color, etc.). Various polypeptides of interest, as well as methods for introducing these polypeptides into a plant, are described, for example, in U.S. Pat. Nos. 4,761,373; 4,769,061; 4,810,648; 4,940,835; 4,975,374; 5,013,659; 5,162,602; 5,276,268; 5,304,730; 5,495,071; 5,554,798; 5,561,236; 5,569,823; 5,767,366; 5,879,903; 5,928,937; 6,084,155; 6,329,504 and 6,337,431; as well as US Patent Publication No. 2001/0016956. See also, on the World Wide Web at lifesci.sussex.ac.uk/home/Neil_Crickmore/Bt/.

Polynucleotides conferring resistance/tolerance to an herbicide that inhibits the growing point or meristem, such as an imidazalinone or a sulfonylurea can also be suitable in some embodiments of the invention. Exemplary polynucleotides in this category code for mutant ALS and AHAS enzymes as described, e.g., in U.S. Pat. Nos. 5,767,366 and 5,928,937. U.S. Pat. Nos. 4,761,373 and 5,013,659 are directed to plants resistant to various imidazalinone or sulfonamide herbicides. U.S. Pat. No. 4,975,374 relates to plant cells and plants containing a nucleic acid encoding a mutant glutamine synthetase (GS) resistant to inhibition by herbicides that are known to inhibit GS, e.g., phosphinothricin and methionine sulfoximine. U.S. Pat. No. 5,162,602 discloses plants resistant to inhibition by cyclohexanedione and aryloxyphenoxypropanoic acid herbicides. The resistance is conferred by an altered acetyl coenzyme A carboxylase (ACCase).

Polypeptides encoded by nucleotides sequences conferring resistance to glyphosate are also suitable for the invention. See, e.g., U.S. Pat. Nos. 4,940,835 and 4,769,061. U.S. Pat. No. 5,554,798 discloses transgenic glyphosate resistant maize plants, which resistance is conferred by an altered 5-enolpyruvyl-3-phosphoshikimate (EPSP) synthase gene.

Polynucleotides coding for resistance to phosphono compounds such as glufosinate ammonium or phosphinothricin, and pyridinoxy or phenoxy propionic acids and cyclohexones are also suitable. See, European Patent Application No. 0 242 246. See also, U.S. Pat. Nos. 5,879,903, 5,276,268 and 5,561,236.

Other suitable polynucleotides include those coding for resistance to herbicides that inhibit photosynthesis, such as a triazine and a benzonitrile (nitrilase) See, U.S. Pat. No. 4,810,648. Additional suitable polynucleotides coding for herbicide resistance include those coding for resistance to 2,2-dichloropropionic acid, sethoxydim, haloxyfop, imidazolinone herbicides, sulfonylurea herbicides, triazolopyrimidine herbicides, s-triazine herbicides and bromoxynil. Also suitable are polynucleotides conferring resistance to a protox enzyme, or that provide enhanced resistance to plant diseases; enhanced tolerance of adverse environmental conditions (abiotic stresses) including but not limited to drought, excessive cold, excessive heat, or excessive soil salinity or extreme acidity or alkalinity; and alterations in plant architecture or development, including changes in developmental timing. See, e.g., U.S. Patent Publication No. 2001/0016956 and U.S. Pat. No. 6,084,155.

Additional suitable polynucleotides include those coding for pesticidal (e.g., insecticidal) polypeptides. These polypeptides may be produced in amounts sufficient to control, for example, insect pests (i.e., insect controlling amounts). It is recognized that the amount of production of a pesticidal polypeptide in a plant necessary to control insects or other pests may vary depending upon the cultivar, type of pest, environmental factors and the like. Polynucleotides useful for additional insect or pest resistance include, for example, those that encode toxins identified in *Bacillus* organisms. Polynucleotides comprising nucleotide sequences encoding *Bacillus thuringiensis* (Bt) Cry proteins from several subspecies have been cloned and recombinant clones have been found to be toxic to lepidopteran, dipteran and coleopteran insect larvae. Examples of such Bt insecticidal proteins include the Cry proteins such as Cry1Aa, Cry1Ab, Cry1Ac, Cry1B, Cry1C, Cry1D, Cry1Ea, Cry1Fa, Cry3A, Cry9A, Cry9B, Cry9C, and the like, as well as vegetative insecticidal proteins such as Vip1, Vip2, Vip3, and the like. A full list of Bt-derived proteins can be found on the worldwide web at *Bacillus thuringiensis* Toxin Nomenclature Database maintained by the University of Sussex (see also, Crickmore et al. (1998) *Microbiol. Mol. Biol. Rev.* 62:807-813).

Polypeptides that are suitable for production in plants further include those that improve or otherwise facilitate the conversion of harvested plants or plant parts into a commercially useful product, including, for example, increased or altered carbohydrate content or distribution, improved fermentation properties, increased oil content, increased protein content, improved digestibility, and increased nutraceutical content, e.g., increased phytosterol content, increased tocopherol content, increased stanol content or increased vitamin content. Polypeptides of interest also include, for example, those resulting in or contributing to a reduced content of an unwanted component in a harvested crop, e.g., phytic acid, or sugar degrading enzymes. By "resulting in" or "contributing to" is intended that the polypeptide of interest can directly or indirectly contribute to the existence of a trait of interest (e.g., increasing cellulose degradation by the use of a heterologous cellulase enzyme).

In some embodiments, the polypeptide contributes to improved digestibility for food or feed. Xylanases are hemicellulolytic enzymes that improve the breakdown of plant cell walls, which leads to better utilization of the plant nutrients by an animal. This leads to improved growth rate and feed conversion. Also, the viscosity of the feeds containing xylan can be reduced. Heterologous production of xylanases in plant cells also can facilitate lignocellulosic conversion to fermentable sugars in industrial processing.

Numerous xylanases from fungal and bacterial microorganisms have been identified and characterized (see, e.g., U.S. Pat. No. 5,437,992; Coughlin et al. (1993) "Proceedings of the Second TRICEL Symposium on *Trichoderma reesei* Cellulases and Other Hydrolases" Espoo; Souminen and Reinikainen, eds. (1993) *Foundation for Biotechnical and Industrial Fermentation Research* 8:125-135; U.S. Patent Publication No. 2005/0208178; and PCT Publication No. WO 03/16654). In particular, three specific xylanases (XYL-I, XYL-II, and XYL-III) have been identified in *T. reesei* (Tenkanen et al. (1992) *Enzyme Microb. Technol.* 14:566; Torronen et al. (1992) *Bio/Technology* 10:1461; and Xu et al. (1998) *Appl. Microbiol. Biotechnol.* 49:718).

In other embodiments, a polypeptide useful for the invention can be a polysaccharide degrading enzyme. Plants of this invention producing such an enzyme may be useful for generating, for example, fermentation feedstocks for bioprocessing. In some embodiments, enzymes useful for a fermentation process include alpha amylases, proteases, pullulanases, isoamylases, cellulases, hemicellulases, xylanases, cyclodextrin glycotransferases, lipases, phytases, laccases, oxidases, esterases, cutinases, granular starch hydrolyzing enzyme and other glucoamylases.

Polysaccharide-degrading enzymes include: starch degrading enzymes such as $\alpha$-amylases (EC 3.2.1.1), glucuronidases (E.C. 3.2.1.131); exo-1,4-$\alpha$-D glucanases such as amyloglucosidases and glucoamylase (EC 3.2.1.3), $\beta$-amylases (EC 3.2.1.2), $\alpha$-glucosidases (EC 3.2.1.20), and other exo-amylases; starch debranching enzymes, such as a) isoamylase (EC 3.2.1.68), pullulanase (EC 3.2.1.41), and the like; b) cellulases such as exo-1,4-3-cellobiohydrolase (EC 3.2.1.91), exo-1,3-$\beta$-D-glucanase (EC 3.2.1.39), P-glucosidase (EC 3.2.1.21); c) L-arabinases, such as endo-1,5-$\alpha$-L-arabinase (EC 3.2.1.99), $\alpha$-arabinosidases (EC 3.2.1.55) and the like; d) galactanases such as endo-1,4-$\beta$-D-galactanase (EC 3.2.1.89), endo-1,3-$\beta$-D-galactanase (EC 3.2.1.90), $\alpha$-galactosidase (EC 3.2.1.22), $\beta$-galactosidase (EC 3.2.1.23) and the like; e) mannanases, such as endo-1,4-$\beta$-D-mannanase (EC 3.2.1.78), $\beta$-mannosidase (EC 3.2.1.25), a-mannosidase (EC 3.2.1.24) and the like; f) xylanases, such as endo-1,4-$\beta$-xylanase (EC 3.2.1.8), $\beta$-D-xylosidase (EC 3.2.1.37), 1,3-$\beta$-D-xylanase, and the like; and g) other enzymes such as a-L-fucosidase (EC 3.2.1.51), $\alpha$-L-rhamnosidase (EC 3.2.1.40), levanase (EC 3.2.1.65), inulanase (EC 3.2.1.7), and the like. In one embodiment, the $\alpha$-amylase is the synthetic α-amylase, Amy797E, described is U.S. Pat. No. 8,093,453, herein incorporated by reference in its entirety.

Further enzymes which may be used with the invention include proteases, such as fungal and bacterial proteases. Fungal proteases include, but are not limited to, those obtained from *Aspergillus, Trichoderma, Mucor* and *Rhizopus*, such as *A. niger, A. awamori, A. oryzae* and *M. miehei*. In some embodiments, the polypeptides of this invention can be cellobiohydrolase (CBH) enzymes (EC 3.2.1.91). In one embodiment, the cellobiohydrolase enzyme can be CBH1 or CBH2.

Other enzymes useful with the invention include, but are not limited to, hemicellulases, such as mannases and arabinofuranosidases (EC 3.2.1.55); ligninases; lipases (e.g., E.C. 3.1.1.3), glucose oxidases, pectinases, xylanases, transglucosidases, alpha 1,6 glucosidases (e.g., E.C. 3.2.1.20); esterases such as ferulic acid esterase (EC 3.1.1.73) and acetyl xylan esterases (EC 3.1.1.72); and cutinases (e.g. E.C. 3.1.1.74).

Double stranded RNA molecules useful with the invention include, but are not limited to those that suppress target insect genes. As used herein the words "gene suppression", when taken together, are intended to refer to any of the well-known methods for reducing the levels of protein produced as a result of gene transcription to mRNA and subsequent translation of the mRNA. Gene suppression is also intended to mean the reduction of protein expression from a gene or a coding sequence including posttranscriptional gene suppression and transcriptional suppression. Posttranscriptional gene suppression is mediated by the homology between of all or a part of a mRNA transcribed from a gene or coding sequence targeted for suppression and the corresponding double stranded RNA used for suppression, and refers to the substantial and measurable reduction of the amount of available mRNA available in the cell for binding by ribosomes. The transcribed RNA can be in the sense orientation to effect what is called co-suppression, in the anti-sense orientation to effect what is called anti-sense suppression, or in both orientations producing a dsRNA to effect what is called RNA interference (RNAi). Transcriptional suppression is mediated by the presence in the cell of a dsRNA, a gene suppression agent, exhibiting substantial sequence identity to a promoter DNA sequence or the complement thereof to effect what is referred to as promoter trans suppression. Gene suppression may be effective against a native plant gene associated with a trait, e.g., to provide plants with reduced levels of a protein encoded by the native gene or with enhanced or reduced levels of an affected metabolite. Gene suppression can also be effective against target genes in plant pests that may ingest or contact plant material containing gene suppression agents, specifically designed to inhibit or suppress the expression of one or more homologous or complementary sequences in the cells of the pest. Such genes targeted for suppression can encode an essential protein, the predicted function of which is selected from the group consisting of muscle formation, juvenile hormone formation, juvenile hormone regulation, ion regulation and transport, digestive enzyme synthesis, maintenance of cell membrane potential, amino acid biosynthesis, amino acid degradation, sperm formation, pheromone synthesis, pheromone sensing, antennae formation, wing formation, leg formation, development and differentiation, egg formation, larval maturation, digestive enzyme formation, haemolymph synthesis, haemolymph maintenance, neurotransmission, cell division, energy metabolism, respiration, and apoptosis.

In some embodiments, the invention provides a transgenic non-human host cell comprising a polynucleotide, a nucleic acid molecule, a chimeric gene, an expression cassette or a recombinant vector of the invention. The transgenic non-human host cell can include, but is not limited to, a plant cell, a yeast cell, a bacterial cell or an insect cell. Accordingly, in some embodiments, the invention provides a bacterial cell selected from the genera *Bacillus, Brevibacillus, Clostridium, Xenorhabdus, Photorhabdus, Pasteuria, Escherichia, Pseudomonas, Erwinia, Serratia, Klebsiella, Salmonella, Pasteurella, Xanthomonas, Streptomyces, Rhizobium, Rhodopseudomonas, Methylophilius, Agrobacterium, Acetobacter, Lactobacillus, Arthrobacter, Azotobacter, Leuconostoc*, or *Alcaligenes*. Thus, for example, as biological insect control agents, the Cry proteins of the invention can be produced by expression of a chimeric gene encoding the Cry proteins of the invention in a bacterial cell. For example, in some embodiments, a *Bacillus thuringiensis* cell comprising a chimeric gene of the invention is provided.

In further embodiments, the invention provides a transgenic plant cell that is a dicot plant cell or a monocot plant cell. In additional embodiments, the dicot plant cell is selected from the group consisting of a soybean cell, sunflower cell, tomato cell, cole crop cell, cotton cell, sugar beet cell and tobacco cell. In further embodiments, the monocot cell is selected from the group consisting of a barley cell, maize cell, oat cell, rice cell, sorghum cell, sugar cane cell and wheat cell. In some embodiments, the invention provides a plurality of dicot cells or monocot cells expressing a Cry protein of the invention that is encoded by a chimeric gene of the invention. In other embodiments the plurality of cells are juxtaposed to form an apoplast and are grown in natural sunlight.

In other embodiments of the invention, an insecticidal Cry protein of the invention is expressed in a higher organism, for example, a plant. In this case, transgenic plants expressing effective amounts of the insecticidal protein protect themselves from plant pests such as insect pests. When an insect starts feeding on such a transgenic plant, it ingests the expressed insecticidal Cry protein. This can deter the insect from further biting into the plant tissue or may even harm or kill the insect. A polynucleotide of the invention is inserted into an expression cassette, which is then stably integrated in the genome of the plant. In other embodiments, the polynucleotide is included in a non-pathogenic self-replicating virus. Plants transformed in accordance with the invention may be monocots or dicots and include, but are not limited to, corn (maize), soybean, rice, wheat, barley, rye, oats, sorghum, millet, sunflower, safflower, sugar beet, cotton, sugarcane, oilseed rape, alfalfa, tobacco, peanuts, vegetables, including, sweet potato, bean, pea, chicory, lettuce, cabbage, cauliflower, broccoli, turnip, carrot, eggplant, cucumber, radish, spinach, potato, tomato, asparagus, onion, garlic, melons, pepper, celery, squash, pumpkin, zucchini, fruits, including, apple, pear, quince, plum, cherry, peach, nectarine, apricot, strawberry, grape, raspberry, blackberry, pineapple, avocado, papaya, mango, banana, and specialty plants, such as *Arabidopsis*, and woody plants such as coniferous and deciduous trees. Preferably, plants of the of the invention are crop plants such as maize, sorghum, wheat, sunflower, tomato, crucifers, peppers, potato, cotton, rice, soybean, sugar beet, sugarcane, tobacco, barley, oilseed rape, and the like.

Once a desired polynucleotide has been transformed into a particular plant species, it may be propagated in that species or moved into other varieties of the same species, particularly including commercial varieties, using traditional breeding techniques.

A polynucleotide of the invention is expressed in transgenic plants, thus causing the biosynthesis of the corresponding Cry protein, either in protoxin or mature toxin form, in the transgenic plants. In this way, transgenic plants with enhanced yield protection in the presence of insect pressure are generated. For their expression in transgenic plants, the nucleotide sequences of the invention may require modification and optimization. Although in many cases genes from microbial organisms can be expressed in plants at high levels without modification, low expression in transgenic plants may result from microbial nucleotide sequences having codons that are not preferred in plants. It is known in the art that living organisms have specific preferences for codon usage, and the codons of the nucleotide sequences described in this invention can be changed to conform with plant preferences, while maintaining the amino acids encoded thereby. Furthermore, high expression in plants, for example corn plants, is best achieved from coding sequences that have at least about 35% GC content, or at least about 45%, or at least about 50%, or at least about 60%. Microbial nucleotide sequences that have low GC contents may express poorly in plants due to the existence of ATTTA motifs that may destabilize messages, and AATAAA motifs that may cause inappropriate polyadenylation. Although certain gene sequences may be adequately expressed in both monocotyledonous and dicotyledonous plant species, sequences can be modified to account for the specific codon preferences and GC content preferences of monocotyledons or dicotyledons as these preferences have been shown to differ (Murray et al. Nucl. Acids Res. 17:477-498 (1989)). In addition, the nucleotide sequences are screened for the existence of illegitimate splice sites that may cause message truncation. All changes required to be made within the nucleotide sequences such as those described above are made using well known techniques of site directed mutagenesis, PCR, and synthetic gene construction using the methods described for example in U.S. Pat. Nos. 5,625,136; 5,500,365 and 6,013,523.

In some embodiments, the invention provides synthetic coding sequences or polynucleotide made according to the procedure disclosed in U.S. Pat. No. 5,625,136, herein incorporated by reference. In this procedure, maize preferred codons, i.e., the single codon that most frequently encodes that amino acid in maize, are used. The maize preferred codon for a particular amino acid can be derived, for example, from known gene sequences from maize. For example, maize codon usage for 28 genes from maize plants is found in Murray et al., Nucleic Acids Research 17:477-498 (1989), the disclosure of which is incorporated herein by reference. Specifically exemplified synthetic sequences of the present invention made with maize optimized codons are represented by any one of SEQ ID NOs: 4-9. It is recognized that codons optimized for expression in one plant species will also function in other plant species but possibly not at the same level as the plant species for which the codons were optimized. In this manner, the nucleotide sequences can be optimized for expression in any plant. It is recognized that all or any part of a nucleotide sequence may be optimized or synthetic. That is, a polynucleotide may comprise a nucleotide sequence that is part native sequence and part codon optimized sequence.

For efficient initiation of translation, sequences adjacent to the initiating methionine may require modification. For example, they can be modified by the inclusion of sequences known to be effective in plants. Joshi has suggested an appropriate consensus for plants (NAR 15:6643-6653 (1987)) and Clonetech suggests a further consensus translation initiator (1993/1994 catalog, page 210). These consensuses are suitable for use with the nucleotide sequences of this invention. The sequences are incorporated into constructions comprising the nucleotide sequences, up to and including the ATG (while leaving the second amino acid unmodified), or alternatively up to and including the GTC subsequent to the ATG (with the possibility of modifying the second amino acid of the transgene).

The novel Cry protein coding sequences of the invention, either as their native sequence or as synthetic sequences as described above, can be operably fused to a variety of promoters for expression in plants including constitutive, inducible, temporally regulated, developmentally regulated, chemically regulated, tissue-preferred and tissue-specific promoters to prepare recombinant DNA molecules, i.e., chimeric genes. The choice of promoter will vary depending on the temporal and spatial requirements for expression, and also depending on the target species. Thus, expression of the nucleotide sequences of this invention in leaves, in stalks or stems, in ears, in inflorescences (e.g. spikes, panicles, cobs, etc.), in roots, or seedlings is preferred. In many cases, however, protection against more than one type of insect pest is sought, and thus expression in multiple tissues is desirable. Although many promoters from dicotyledons have been shown to be operational in monocotyledons and vice versa, ideally dicotyledonous promoters are selected for expression in dicotyledons, and monocotyledonous promoters for expression in monocotyledons. However, there is no restriction to the provenance of selected promoters; it is sufficient that they are operational in driving the expression of the nucleotide sequences in the desired cell.

Suitable constitutive promoters include, for example, CaMV 35S promoter (SEQ ID NO:1546; Odell et al., Nature 313:810-812, 1985); *Arabidopsis* At6669 promoter (SEQ ID NO:1652; see PCT Publication No. W004081173A2); maize Ubi 1 (Christensen et al., Plant Mol. Biol. 18:675-689, 1992); rice actin (McElroy et al., Plant Cell 2:163-171, 1990); pEMU (Last et al., Theor. Appl. Genet. 81:581-588, 1991); CaMV 19S (Nilsson et al., Physiol. Plant 100:456-462, 1997); GOS2 (de Pater et al., Plant J November; 2(6):837-44, 1992); ubiquitin (Christensen et al., Plant Mol. Biol. 18: 675-689, 1992); Rice cyclophilin (Bucholz et al., Plant Mol Biol. 25(5):837-43, 1994); Maize H3 histone (Lepetit et al., Mol. Gen. Genet. 231: 276-285, 1992); Actin 2 (An et al., Plant J. 10(1); 107-121, 1996), constitutive root tip CT2 promoter (SEQ ID NO: 1535; see also PCT application No. IL/2005/000627) and Synthetic Super MAS (Ni et al., The Plant Journal 7: 661-76, 1995). Other constitutive promoters include those in U.S. Pat. Nos. 5,659,026, 5,608,149; 5,608,144; 5,604,121; 5,569,597: 5,466,785; 5,399,680; 5,268,463; and 5,608,142.Molec. Biol.

Tissue-specific or tissue-preferential promoters useful for the expression of the novel cry protein coding sequences of the invention in plants, particularly maize, are those that direct expression in root, pith, leaf or pollen. Suitable tissue-specific promoters include, but not limited to, leaf-specific promoters [such as described, for example, by Yamamoto et al., Plant J. 12:255-265, 1997; Kwon et al., Plant Physiol. 105:357-67, 1994; Yamamoto et al., Plant Cell Physiol. 35:773-778, 1994; Gotor et al., Plant J. 3:509-18, 1993; Orozco et al., Plant Mol. Biol. 23:1129-1138, 1993; and Matsuoka et al., Proc. Natl. Acad. Sci. USA 90:9586-9590, 1993], seed-preferred promoters [e.g., from seed specific genes (Simon, et al., Plant Mol. Biol. 5. 191, 1985; Scofield, et al., J. Biol. Chem. 262: 12202, 1987; Baszczynski, et al., Plant Mol. Biol. 14: 633, 1990), Brazil Nut albumin (Pearson' et al., Plant Mol. Biol. 18: 235-245, 1992), legumin (Ellis, et al. Plant Mol. Biol. 10: 203-214, 1988), Glutelin (rice) (Takaiwa, et al., Mol. Gen. Genet. 208: 15-22, 1986; Takaiwa, et al., FEBS Letts. 221: 43-47, 1987), Zein (Matzke et al., Plant Mol Biol, 143).323-32 1990), napA (Stalberg, et al., Planta 199: 515-519, 1996), Wheat SPA (Albanietal, Plant Cell, 9: 171-184, 1997), sunflower oleosin (Cummins, et al., Plant Mol. Biol. 19: 873-876, 1992)], endosperm specific promoters [e.g., wheat LMW and HMW, glutenin-1 (Mol Gen Genet 216:81-90, 1989; NAR 17:461-2), wheat a, b and g gliadins (EMB03:1409-15, 1984), Barley ltrl promoter, barley BI, C, D hordein (Theor Appl Gen 98:1253-62, 1999; Plant J 4:343-55, 1993; Mol Gen Genet 250:750-60, 1996), Barley DOF (Mena et al., The Plant Journal, 116(1): 53-62, 1998), Biz2 (EP99106056.7), Synthetic promoter (Vicente-Carbajosa et al., Plant J. 13: 629-640, 1998), rice prolamin NRP33, rice-globulin Glb-1 (Wu et al., Plant Cell Physiology 39(8) 885-889, 1998), rice alpha-globulin REB/OHP-1 (Nakase et al. Plant Mol. Biol. 33: 513-S22, 1997), rice ADP-glucose PP (Trans Res 6:157-68, 1997), maize ESR gene family (Plant J 12:235-46, 1997), sorgum gamma-kafirin (Plant Mol. Biol 32:1029-35, 1996)], embryo specific promoters [e.g., rice OSH1 (Sato et al., Proc. Nati. Acad. Sci. USA, 93: 8117-8122), KNOX (Postma-Haarsma of al, Plant Mol. Biol. 39:257-71, 1999), rice oleosin (Wu et at, J. Biochem., 123:386, 1998)], flower-specific promoters [e.g., AtPRP4, chalene synthase (chsA) (Van der Meer, et al., Plant Mol. Biol. 15, 95-109, 1990), LAT52 (Twell et al., Mol. Gen Genet. 217:240-245; 1989), apetala-3, plant reproductive tissues [e.g., OsMADS promoters (U.S. Patent Application 2007/0006344)].

The nucleotide sequences of this invention can also be expressed under the regulation of promoters that are chemically regulated. This enables the Cry proteins of the invention to be synthesized only when the crop plants are treated with the inducing chemicals. Examples of such technology for chemical induction of gene expression is detailed in the published application EP 0 332 104 and U.S. Pat. No. 5,614,395. In one embodiment, the chemically regulated promoter is the tobacco PR-1a promoter.

Another category of promoters useful in the invention is that which is wound inducible. Numerous promoters have been described which are expressed at wound sites and also at the sites of phytopathogen infection. Ideally, such a promoter should only be active locally at the sites of insect invasion, and in this way the insecticidal proteins only accumulate in cells that need to synthesize the insecticidal proteins to kill the invading insect pest. Examples of promoters of this kind include those described by Stanford et al. Mol. Gen. Genet. 215:200-208 (1989), Xu et al. Plant Molec. Biol. 22:573-588 (1993), Logemann et al. Plant Cell 1:151-158 (1989), Rohrmeier & Lehle, Plant Molec. Biol. 22:783-792 (1993), Firek et al. Plant Molec. Biol. 22:129-142 (1993), and Warner et al. Plant J. 3:191-201 (1993).

Non-limiting examples of promoters that cause tissue specific expression patterns that are useful in the invention include green tissue specific, root specific, stem specific, or flower specific. Promoters suitable for expression in green tissue include many that regulate genes involved in photosynthesis and many of these have been cloned from both monocotyledons and dicotyledons. One such promoter is the maize PEPC promoter from the phosphoenol carboxylase gene (Hudspeth & Grula, Plant Molec. Biol. 12:579-589 (1989)). Another promoter for root specific expression is that described by de Framond (FEBS 290:103-106 (1991) or U.S. Pat. No. 5,466,785). Another promoter useful in the invention is the stem specific promoter described in U.S. Pat. No. 5,625,136, which naturally drives expression of a maize trpA gene.

In addition to the selection of a suitable promoter, constructs for expression of an insecticidal toxin in plants require an appropriate transcription terminator to be operably linked downstream of the heterologous nucleotide sequence. Several such terminators are available and known in the art (e.g. tml from CaMV, E9 from rbcS). Any available terminator known to function in plants can be used in the context of this invention.

Numerous other sequences can be incorporated into expression cassettes described in this invention. These include sequences that have been shown to enhance expression such as intron sequences (e.g. from Adhl and bronzel) and viral leader sequences (e.g. from TMV, MCMV and AMV).

It may be preferable to target expression of the nucleotide sequences of the present invention to different cellular localizations in the plant. In some cases, localization in the cytosol may be desirable, whereas in other cases, localization in some subcellular organelle may be preferred. Any mechanism for targeting gene products, e.g., in plants, can be used to practice this invention, and such mechanisms are known to exist in plants and the sequences controlling the functioning of these mechanisms have been characterized in some detail. Sequences have been characterized which cause the targeting of gene products to other cell compartments Amino terminal sequences can be responsible for targeting a protein of interest to any cell compartment, such as, a vacuole, mitochondrion, peroxisome, protein bodies, endoplasmic reticulum, chloroplast, starch granule, amyloplast, apoplast or cell wall of a plant (e.g. Unger et. al. Plant Molec. Biol. 13: 411-418 (1989); Rogers et. al. (1985) Proc. Natl. Acad. Sci. USA 82: 6512-651; U.S. Pat. No. 7,102,057; WO 2005/096704, all of which are hereby incorporated by reference. Optionally, the signal sequence may be an N-terminal signal sequence from waxy, an N-terminal signal sequence from gamma-zein, a starch binding domain, a C-terminal starch binding domain, a chloroplast targeting sequence, which imports the mature protein to the chloroplast (Comai et. al. (1988) J. Biol. Chem. 263: 15104-15109; van den Broeck, et. al. (1985) Nature 313: 358-363; U.S. Pat. No. 5,639,949) or a secretion signal sequence from aleurone cells (Koehler & Ho, Plant Cell 2: 769-783 (1990)). Additionally, amino terminal sequences in conjunction with carboxy terminal sequences are responsible for vacuolar targeting of gene products (Shinshi et. al. (1990) Plant Molec. Biol. 14: 357-368). In one embodiment, the signal sequence selected includes the known cleavage site, and the fusion constructed takes into account any amino acids after the cleavage site(s), which are required for cleavage. In some cases this requirement may be fulfilled by the addition of a small number of amino acids between the cleavage site and the transgene ATG or, alternatively, replacement of some amino acids within the transgene sequence. These construction techniques are well known in the art and are equally applicable to any cellular compartment.

It will be recognized that the above-described mechanisms for cellular targeting can be utilized not only in conjunction with their cognate promoters, but also in conjunction with heterologous promoters so as to effect a specific cell-targeting goal under the transcriptional regulation of a promoter that has an expression pattern different to that of the promoter from which the targeting signal derives.

Plant Transformation

Procedures for transforming plants are well known and routine in the art and are described throughout the literature. Non-limiting examples of methods for transformation of plants include transformation via bacterial-mediated nucleic acid delivery (e.g., via *Agrobacterium*), viral-mediated nucleic acid delivery, silicon carbide or nucleic acid whisker-mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) or biological mechanism that results in the introduction of nucleic acid into the plant cell, including any combination thereof. General guides to various plant transformation methods known in the art include Miki et al. ("Procedures for Introducing Foreign DNA into Plants" in *Methods in Plant Molecular Biology and Biotechnology*, Glick, B. R. and Thompson, J. E., Eds. (CRC Press, Inc., Boca Raton, 1993), pages 67-88) and Rakowoczy-Trojanowska (*Cell. Mol. Biol. Lett.* 7:849-858 (2002)).

For *Agrobacterium*-mediated transformation, binary vectors or vectors carrying at least one T-DNA border sequence are suitable, whereas for direct gene transfer (e.g., particle bombardment and the like) any vector is suitable and linear DNA containing only the construction of interest can be used. In the case of direct gene transfer, transformation with a single DNA species or co-transformation can be used (Schocher et al., *Biotechnology* 4:1093-1096 (1986)). For both direct gene transfer and *Agrobacterium*-mediated transfer, transformation is usually (but not necessarily) undertaken with a selectable marker that may be a positive selection (Phosphomannose Isomerase), provide resistance to an antibiotic (kanamycin, hygromycin or methotrexate) or a herbicide (glyphosate or glufosinate). However, the choice of selectable marker is not critical to the invention.

*Agrobacterium*-mediated transformation is a commonly used method for transforming plants because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) *Plant Cell* 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hifgen & Willmitzer (1988) *Nucleic Acids Res.* 16:9877).

Dicots as well as monocots may be transformed using *Agrobacterium*. Methods for *Agrobacterium*-mediated transformation of rice include well known methods for rice transformation, such as those described in any of the following: European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). Agrobacteria transformed by such a vector can then be used in known manner for the transformation of plants, such as plants used as a model, like *Arabidopsis* or crop plants such as, by way of example, tobacco plants, for example by immersing bruised leaves or chopped leaves in an agrobacterial solution and then culturing them in suitable media. The transformation of plants by means of *Agrobacterium tumefaciens* is described, for example, by Hagen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

As discussed previously, another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of interest. Alternatively, a cell or cells can be surrounded by the vector so that the vector is carried into the cell by the wake of the particle. Biologically active particles (e.g., a dried yeast cell, a dried bacterium or a bacteriophage, each containing one or more nucleic acids sought to be introduced) also can be propelled into plant tissue.

In other embodiments, a polynucleotide of the invention can be directly transformed into the plastid genome. A major advantage of plastid transformation is that plastids are generally capable of expressing bacterial genes without substantial modification, and plastids are capable of expressing multiple open reading frames under control of a single promoter. Plastid transformation technology is extensively described in U.S. Pat. Nos. 5,451,513, 5,545,817, and 5,545,818, in PCT application no. WO 95/16783, and in McBride et al. (1994) *Proc. Nati. Acad. Sci. USA* 91, 7301-7305. The basic technique for chloroplast transformation involves introducing regions of cloned plastid DNA flanking a selectable marker together with the gene of interest into a suitable target tissue, e.g., using biolistics or protoplast transformation (e.g., calcium chloride or PEG mediated transformation). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin or streptomycin can be utilized as selectable markers for transformation (Svab, Z., Hajdukiewicz, P., and Maliga, P. (1990) *Proc. Natl. Acad. Sci. USA* 87, 8526-8530; Staub, J. M., and Maliga, P. (1992) *Plant Cell* 4, 39-45). The presence of cloning sites between these markers allows creation of a plastid targeting vector for introduction of foreign genes (Staub, J. M., and Maliga, P. (1993) *EMBO J.* 12, 601-606). Substantial increases in transformation frequency can be obtained by replacement of the recessive rRNA or r-protein antibiotic resistance genes with a dominant selectable marker, the bacterial aadA gene encoding the spectinomycin-cletoxifying enzyme aminoglycoside-3'-adenyltransferase (Svab, Z., and Maliga, P. (1993) *Proc. Natl. Acad. Sci. USA* 90, 913-917). Previously, this marker had been used successfully for high-frequency transformation of the plastid genome of the green alga *Chlamydomonas reinhardtii* (Goldschmidt-Clermont, M. (1991) *Nucl. Acids Res.* 19:4083-4089). Other selectable markers useful for plastid transformation are known in the art and encompassed within the scope of the invention. Typically, approximately 15-20 cell division cycles following transformation are required to reach a homoplastidic state. Plastid expression, in which genes are inserted by homologous recombination into all of the several thousand copies of the circular plastid genome present in each plant cell, takes advantage of the enormous copy number advantage over nuclear-expressed genes to permit expression levels that can readily exceed 10% of the total soluble plant protein. In one embodiment, a polynucleotide of the invention can be inserted into a plastid-targeting vector and transformed into the plastid genome of a desired plant host. Thus, plants homoplastic for plastid genomes containing a nucleotide sequence of the invention can be obtained, which are capable of high expression of the polynucleotide.

Methods of selecting for transformed, transgenic plants, plant cells or plant tissue culture are routine in the art and can be employed in the methods of the invention provided herein. For example, a recombinant vector of the invention also can include an expression cassette comprising a nucleotide sequence for a selectable marker, which can be used to select a transformed plant, plant part or plant cell. As used herein, "selectable marker" means a nucleotide sequence that when expressed imparts a distinct phenotype to the plant, plant part or plant cell expressing the marker and thus allows such transformed plants, plant parts or plant cells to be distinguished from those that do not have the marker. Such a nucleotide sequence may encode either a selectable or screenable marker, depending on whether the marker confers a trait that can be selected for by chemical means, such as by using a selective agent (e.g., an antibiotic, herbicide, or the like), or on whether the marker is simply a trait that one can identify through observation or testing, such as by screening (e.g., the R-locus trait). Of course, many examples of suitable selectable markers are known in the art and can be used in the expression cassettes described herein.

Examples of selectable markers include, but are not limited to, a nucleotide sequence encoding neo or nptII, which confers resistance to kanamycin, G418, and the like (Potrykus et al. (1985) *Mol. Gen. Genet.* 199:183-188); a nucleotide sequence encoding bar, which confers resistance to phosphinothricin; a nucleotide sequence encoding an altered 5-enolpyruvylshikimate-3-phosphate (EPSP) synthase, which confers resistance to glyphosate (Hinchee et al. (1988) *Biotech.* 6:915-922); a nucleotide sequence encoding a nitrilase such as bxn from *Klebsiella ozaenae* that confers resistance to bromoxynil (Stalker et al. (1988) *Science* 242:419-423); a nucleotide sequence encoding an altered acetolactate synthase (ALS) that confers resistance to imidazolinone, sulfonylurea or other ALS-inhibiting chemicals (EP Patent Application No. 154204); a nucleotide sequence encoding a methotrexate-resistant dihydrofolate reductase (DHFR) (Thillet et al. (1988) *J. Biol. Chem.* 263:12500-12508); a nucleotide sequence encoding a dalapon dehalogenase that confers resistance to dalapon; a nucleotide sequence encoding a mannose-6-phosphate isomerase (also referred to as phosphomannose isomerase (PMI)) that confers an ability to metabolize mannose (U.S. Pat. Nos. 5,767,378 and 5,994,629); a nucleotide sequence encoding an altered anthranilate synthase that confers resistance to 5-methyl tryptophan; or a nucleotide sequence encoding hph that confers resistance to hygromycin. One of skill in the art is capable of choosing a suitable selectable marker for use in an expression cassette of this invention.

Additional selectable markers include, but are not limited to, a nucleotide sequence encoding β-glucuronidase or uidA (GUS) that encodes an enzyme for which various chromogenic substrates are known; an R-locus nucleotide sequence that encodes a product that regulates the production of anthocyanin pigments (red color) in plant tissues (Dellaporta et al., "Molecular cloning of the maize R-nj allele by transposon-tagging with Ac" 263-282 In: *Chromosome Structure and Function: Impact of New Concepts,* 18th Stadler Genetics Symposium (Gustafson & Appels eds., Plenum Press 1988)); a nucleotide sequence encoding β-lactamase, an enzyme for which various chromogenic substrates are known (e.g., PADAC, a chromogenic cephalosporin) (Sutcliffe (1978) *Proc. Natl. Acad. Sci. USA* 75:3737-3741); a nucleotide sequence encoding xylE that encodes a catechol dioxygenase (Zukowsky et al. (1983) *Proc. Natl. Acad. Sci. USA* 80:1101-1105); a nucleotide sequence encoding tyrosinase, an enzyme capable of oxidizing tyrosine to DOPA and dopaquinone, which in turn condenses to form melanin (Katz et al. (1983) *J. Gen. Microbiol.* 129:2703-2714); a nucleotide sequence encoding β-galactosidase, an enzyme for which there are chromogenic substrates; a nucleotide sequence encoding luciferase (lux) that allows for bioluminescence detection (Ow et al. (1986) *Science* 234:856-859); a nucleotide sequence encoding aequorin which may be employed in calcium-sensitive bioluminescence detection (Prasher et al. (1985) *Biochem. Biophys. Res. Comm.* 126:1259-1268); or a nucleotide sequence encoding green fluorescent protein (Niedz et al. (1995) *Plant Cell Reports* 14:403-406). One of skill in the art is capable of choosing a suitable selectable marker for use in an expression cassette of this invention.

Further, as is well known in the art, intact transgenic plants can be regenerated from transformed plant cells, plant tissue culture or cultured protoplasts using any of a variety of known techniques. Plant regeneration from plant cells, plant tissue culture or cultured protoplasts is described, for example, in Evans et al. (*Handbook of Plant Cell Cultures,* Vol. 1, MacMilan Publishing Co. New York (1983)); and Vasil I. R. (ed.) (*Cell Culture and Somatic Cell Genetics of Plants,* Acad. Press, Orlando, Vol. I (1984), and Vol. II (1986)).

Additionally, the genetic properties engineered into the transgenic seeds and plants, plant parts, or plant cells of the invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

A polynucleotide therefore can be introduced into the plant, plant part or plant cell in any number of ways that are well known in the art, as described above. Therefore, no particular method for introducing one or more polynucleotides into a plant is relied upon, rather any method that allows the one or more polynucleotides to be stably integrated into the genome of the plant can be used. Where more than one polynucleotides is to be introduced, the respective polynucleotides can be assembled as part of a single nucleic acid molecule, or as separate nucleic acid molecules, and can be located on the same or different nucleic acid molecules. Accordingly, the polynucleotides can be introduced into the cell of interest in a single transformation event, in separate transformation events, or, for example, in plants, as part of a breeding protocol.

Additional embodiments of the invention include harvested products produced from the transgenic plants or parts thereof of the invention, as well as a processed product produced from the harvested products. A harvested product can be a whole plant or any plant part, as described herein. Thus, in some embodiments, non-limiting examples of a harvested product include a seed, a fruit, a flower or part thereof (e.g., an anther, a stigma, and the like), a leaf, a stem, and the like. In other embodiments, a processed product includes, but is not limited to, a flour, meal, oil, starch, cereal, and the like produced from a harvested seed or other plant part of the invention, wherein said seed or other plant part comprises a nucleic acid molecule/polynucleotide/nucleotide sequence of this invention.

In other embodiments, the invention provides an extract from a transgenic seed or a transgenic plant of the invention, wherein the extract comprises a nucleic acid molecule, a polynucleotide, a nucleotide sequence or a toxic protein of the invention. Extracts from plants or plant parts can be made according to procedures well known in the art (See, de la Torre et al., *Food, Agric. Environ.* 2(1):84-89 (2004); Guidet, *Nucleic Acids Res.* 22(9): 1772-1773 (1994); Lipton et al., *Food Agric. Immun.* 12:153-164 (2000)).

Insecticidal Compositions

In some embodiments, the invention provides an insecticidal composition comprising a Cry protein of the invention in an agriculturally acceptable carrier. As used herein an "agriculturally-acceptable carrier" can include natural or synthetic, organic or inorganic material which is combined with the active Cry protein to facilitate its application to or in the plant, or part thereof. Examples of agriculturally acceptable carriers include, without limitation, powders, dusts, pellets, granules, sprays, emulsions, colloids, and solutions. Agriculturally-acceptable carriers further include, but are not limited to, inert components, dispersants, surfactants, adjuvants, tackifiers, stickers, binders, or combinations thereof, that can be used in agricultural formulations. Such compositions can be applied in any manner that brings the pesticidal proteins or other pest control agents in contact with the pests. Accordingly, the compositions can be applied to the surfaces of plants or plant parts, including seeds, leaves, flowers, stems, tubers, roots, and the like. In other embodiments, a plant producing a Cry protein of the invention in planta is an agricultural-carrier of the expressed Cry protein.

In further embodiments, the insecticidal composition comprises a bacterial cell or a transgenic bacterial cell of the invention, wherein the bacterial cell or transgenic bacterial cell produces a Cry protein of the invention. Such an insecticidal composition can be prepared by desiccation, lyophilization, homogenization, extraction, filtration, centrifugation, sedimentation, or concentration of a culture of *Bacillus thuringiensis* (Bt). Such Bt cultures can be selected from the group of Bt strains consisting of C0633, C0724, C1100 described below in the Examples or transgenic Bt cultures. In additional embodiments, the composition comprises from about 1% to about 99% by weight of the Cry protein of the invention.

The Cry proteins of the invention can be used in combination with other pest control agents to increase pest target range or for the prevention or management of insect resistance. Therefore, in some embodiments, the invention provides a composition that controls one or more plant pests, wherein the composition comprises a first Cry protein of the invention and a second pest control agent different from the first Cry protein. In other embodiments, the composition is a formulation for topical application to a plant. In still other embodiments, the composition is a transgenic plant. In further embodiments, the composition is a combination of a formulation topically applied to a transgenic plant. In some embodiments, the formulation comprises the first Cry protein of the invention when the transgenic plant comprises the second pest control agent. In other embodiments, the formulation comprises the second pest control agent when the transgenic plant comprises the first Cry protein of the invention.

In some embodiments, the second pest control agent can be an agent selected from the group consisting of a chemical pesticide, such as an insecticide, a *Bacillus thuringiensis* (Bt) insecticidal protein, a Xenorhabdus insecticidal protein, a *Photorhabdus* insecticidal protein, a *Brevibacillus laterosporus* insecticidal protein, a *Bacillus sphaericus* insecticidal protein, a protease inhibitors (both serine and cysteine types), lectins, alpha-amylase, peroxidase, cholesterol oxidase and a double stranded RNA (dsRNA) molecule.

In other embodiments, the second pest control agent is a chemical pesticide selected from the group consisting of pyrethroids, carbamates, neonicotinoids, neuronal sodium channel blockers, insecticidal macrocyclic lactones, gamma-aminobutyric acid (GABA) antagonists, insecticidal ureas and juvenile hormone mimics. In other embodiments, the chemical pesticide is selected from the group consisting of abamectin, acephate, acetamiprid, amidoflumet (S-1955), avermectin, azadirachtin, azinphos-methyl, bifenthrin, binfenazate, buprofezin, carbofuran, chlorfenapyr, chlorfluazuron, chlorpyrifos, chlorpyrifos-methyl, chromafenozide, clothianidin, cyfluthrin, beta-cyfluthrin, cyhalothrin, lambda-cyhalothrin, cypermethrin, cyromazine, deltamethrin, diafenthiuron, diazinon, diflubenzuron, dimethoate, diofenolan, emamectin, endosulfan, esfenvalerate, ethiprole, fenothicarb, fenoxycarb, fenpropathrin, fenproximate, fenvalerate, fipronil, flonicamid, flucythrinate, tau-fluvalinate, flufenerim (UR-50701), flufenoxuron, fonophos, halofenozide, hexaflumuron, imidacloprid, indoxacarb, isofenphos, lufenuron, malathion, metaldehyde, methamidophos, methidathion, methomyl, methoprene, methoxychlor, monocrotophos, methoxyfenozide, nithiazin, novaluron, noviflumuron (XDE-007), oxamyl, parathion, parathion-methyl, permethrin, phorate, phosalone, phosmet, phosphamidon, pirimicarb, profenofos, pymetrozine, pyridalyl, pyriproxyfen, rotenone, spinosad, spiromesifin (BSN 2060), sulprofos, tebufenozide, teflubenzuron, tefluthrin, terbufos, tetrachlorvinphos, thiacloprid, thiamethoxam, thiodicarb, thiosultap-sodium, tralomethrin, trichlorfon and triflumuron, aldicarb, oxamyl, fenamiphos, amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad. In still other embodiments, the chemical pesticide is selected from the group consisting of cypermethrin, cyhalothrin, cyfluthrin and beta-cyfluthrin, esfenvalerate, fenvalerate, tralomethrin, fenothicarb, methomyl, oxamyl, thiodicarb, clothianidin, imidacloprid, thiacloprid, indoxacarb, spinosad, abamectin, avermectin, emamectin, endosulfan, ethiprole, fipronil, flufenoxuron, triflumuron, diofenolan, pyriproxyfen, pymetrozine and amitraz.

In additional embodiments, the second pest control agent can be one or more of any number of *Bacillus thuringiensis* insecticidal proteins including but not limited to a Cry protein, a vegetative insecticidal protein (VIP) and insecticidal chimeras of any of the preceding insecticidal proteins. In other embodiments, the second pest control agent is a Cry protein selected from the group consisting of Cry1Aa, Cry1Ab, Cry1Ac, Cry1Ad, Cry1Ae, Cry1Af, Cry1Ag, Cry1Ah, Cry1Ai, Cry1Aj, Cry1Ba, Cry1Bb, Cry1Bc, Cry1Bd, Cry1Be, Cry1Bf, Cry1Bg, Cry1Bh, Cry1Bi, Cry1Ca, Cry1Cb, Cry1Da, Cry1Db, Cry1Dc, Cry1Dd, Cry1Ea, Cry1Eb, Cry1Fa, Cry1Fb, Cry1Ga, Cry1Gb, Cry1Gc, Cry1Ha, Cry1Hb, Cry1Hc, Cry1Ia, Cry1Ib, Cry1Ic, Cry1Id, Cry1Ie, Cry1If, Cry1Ig, Cry1Ja, Cry1Jb, Cry1Jc, Cry1Jd, Cry1Ka, Cry1La, Cry1Ma, Cry1Na, Cry1Nb, Cry2Aa, Cry2Ab, Cry2Ac, Cry2Ad, Cry2Ae, Cry2Af, Cry2Ag, Cry2Ah, Cry2Ai, Cry2Aj, Cry2Ak, Cry2Al, Cry2Ba, Cry3Aa, Cry3Ba, Cry3Bb, Cry3Ca, Cry4Aa, Cry4Ba, Cry4Ca, Cry4Cb, Cry4Cc, Cry5Aa, Cry5Ab, Cry5Ac, Cry5Ad, Cry5Ba, Cry5Ca, Cry5 Da, Cry5Ea, Cry6Aa, Cry6Ba, Cry7Aa, Cry7Ab, Cry7Ac, Cry7Ba, Cry7Bb, Cry7Ca, Cry7Cb, Cry7 Da, Cry7Ea, Cry7Fa, Cry7Fb, Cry7Ga, Cry7Gb, Cry7Gc, Cry7Gd, Cry7Ha, Cry7Ia, Cry7Ja, Cry7Ka, Cry7Kb, Cry7La, Cry8Aa, Cry8Ab, Cry8Ac, Cry8Ad, Cry8Ba, Cry8Bb, Cry8Bc, Cry8Ca, Cry8 Da, Cry8Db, Cry8Ea, Cry8Fa, Cry8Ga, Cry8Ha, Cry8Ia, Cry8Ib, Cry8Ja, Cry8Ka, Cry8Kb, Cry8La, Cry8Ma, Cry8Na, Cry8 Pa, Cry8Qa, Cry8Ra, Cry8Sa, Cry8Ta, Cry9Aa, Cry9Ba, Cry9Bb, Cry9Ca, Cry9 Da, Cry9Db, Cry9Dc, Cry9Ea, Cry9Eb, Cry9Ec, Cry9Ed, Cry9Ee, Cry9Fa, Cry9Ga, Cry10Aa, Cry11Aa, Cry11Ba, Cry11Bb, Cry12Aa, Cry13Aa, Cry14Aa, Cry14Ab, Cry15Aa, Cry16Aa, Cry17Aa, Cry18Aa, Cry18Ba, Cry18Ca, Cry19Aa, Cry19Ba, Cry19Ca, Cry20Aa, Cry20Ba, Cry21Aa, Cry21Ba, Cry21Ca, Cry21 Da, Cry21Ea, Cry21Fa, Cry21Ga, Cry21Ha, Cry22Aa, Cry22Ab, Cry22Ba, Cry22Bb, Cry23Aa, Cry24Aa, Cry24Ba, Cry24Ca, Cry25Aa, Cry26Aa, Cry27Aa, Cry28Aa, Cry29Aa, Cry29Ba, Cry30Aa, Cry30Ba, Cry30Ca, Cry30 Da, Cry30Db, Cry30Ea, Cry30Fa, Cry30Ga, Cry31Aa, Cry31Ab, Cry31Ac, Cry31Ad, Cry32Aa, Cry32Ab, Cry32Ba, Cry32Ca, Cry32Cb, Cry32 Da, Cry32Ea, Cry32Eb, Cry32Fa, Cry32Ga, Cry32Ha, Cry32Hb, Cry32Ia, Cry32Ja, Cry32Ka, Cry32La, Cry32Ma, Cry32 Mb, Cry32Na, Cry32Oa, Cry32 Pa, Cry32Qa, Cry32Ra, Cry32Sa, Cry32Ta, Cry32Ua, Cry33Aa, Cry34Aa, Cry34Ab, Cry34Ac, Cry34Ba, Cry35Aa, Cry35Ab, Cry35Ac, Cry35Ba, Cry36Aa, Cry37Aa, Cry38Aa, Cry39Aa, Cry40Aa, Cry40Ba, Cry40Ca, Cry40 Da, Cry41Aa, Cry41Ab, Cry41Ba, Cry42Aa, Cry43Aa, Cry43Ba, Cry43Ca, Cry43Cb, Cry43Cc, Cry44Aa, Cry45Aa, Cry46Aa Cry46Ab, Cry47Aa, Cry48Aa, Cry48Ab, Cry49Aa, Cry49Ab, Cry50Aa, Cry50Ba, Cry51Aa, Cry52Aa, Cry52Ba, Cry53Aa, Cry53Ab, Cry54Aa, Cry54Ab, Cry54Ba, Cry55Aa, Cry56Aa, Cry57Aa, Cry57Ab, Cry58Aa, Cry59Aa, Cry59Ba, Cry60Aa, Cry60Ba, Cry61Aa, Cry62Aa, Cry63Aa, Cry64Aa, Cry65Aa, Cry66Aa, Cry67Aa, Cry68Aa, Cry69Aa, Cry69Ab, Cry70Aa, Cry70Ba, Cry70Bb, Cry71Aa, Cry72Aa and Cry73Aa.

In further embodiments, the second pest control agent is a Vip3 vegetative insecticidal protein selected from the group consisting of Vip3Aa1, Vip3Aa2, Vip3Aa3, Vip3Aa4, Vip3Aa5, Vip3Aa6, Vip3Aa7, Vip3Aa8, Vip3Aa9, Vip3Aa10, Vip3Aa11, Vip3Aa12, Vip3Aa13, Vip3Aa14, Vip3Aa15, Vip3Aa16, Vip3Aa17, Vip3Aa18, Vip3Aa19, Vip3Aa20, Vip3Aa21, Vip3Aa22, Vip3Aa23, Vip3Aa24, Vip3Aa25, Vip3Aa26, Vip3Aa27, Vip3Aa28, Vip3Aa29, Vip3Aa30, Vip3Aa31, Vip3Aa32, Vip3Aa33, Vip3Aa34, Vip3Aa35, Vip3Aa36, Vip3Aa37, Vip3Aa38, Vip3Aa39, Vip3Aa40, Vip3Aa41, Vip3Aa42, Vip3Aa43, Vip3Aa44, Vip3Ab1, Vip3Ab2, Vip3Ac1, Vip3Ad1, Vip3Ad2, Vip3Ae1, Vip3Af1, Vip3Af2, Vip3Af3, Vip3Ag 1,Vip3Ag2, Vip3Ag3 HM117633, Vip3Ag4, Vip3Ag5, Vip3Ah1, Vip3Ba1, Vip3Ba2, Vip3Bb1, Vip3Bb2 and Vip3Bb3.

In still further embodiments, the first Cry protein of the invention and the second pest control agent are co-expressed in a transgenic plant. This co-expression of more than one pesticidal principle in the same transgenic plant can be achieved by genetically engineering a plant to contain and express all the genes necessary. Alternatively, a plant, Parent 1, can be genetically engineered for the expression of the Cry protein of the invention. A second plant, Parent 2, can be genetically engineered for the expression of a second pest control agent. By crossing Parent 1 with Parent 2, progeny plants are obtained which express all the genes introduced into Parents 1 and 2.

In other embodiments, the invention provides a stacked transgenic plant resistant to plant pest infestation comprising a DNA sequence encoding a dsRNA for suppression of an essential gene in a target pest and a DNA sequence encoding a Cry protein of the invention exhibiting biological activity against the target pest. It has been reported that dsRNAs are ineffective against certain lepidopteran pests (Rajagopol et al. 2002. J. Biol. Chem. 277:468-494), likely due to the high pH of the midgut which destabilizes the dsRNA. Therefore, in some embodiments where the target pest is a lepidopteran pest, a Cry protein of the invention acts to transiently reduce the midgut pH which serves to stabilize the co-ingested dsRNA rendering the dsRNA effective in silencing the target genes.

In addition to providing compositions, the invention provides methods of producing a Cry protein toxic to a lepidopteran pest. Such a method comprises, culturing a transgenic non-human host cell that comprises polynucleotide or a chimeric gene or nucleic acid molecule or a recombinant vector of the invention under conditions in which the host cell produces a protein toxic to the lepidopteran pest. In some embodiments, the transgenic non-human host cell is a plant cell. In some other embodiments, the plant cell is a maize cell. In other embodiments, the conditions under which the plant cell or maize cell are grown include natural sunlight. In other embodiments, the transgenic non-human host cell is a bacterial cell. In still other embodiments, the transgenic non-human host cell is a yeast cell.

In other embodiments of the method, the lepidopteran pest is selected from the group consisting of European corn borer (*Ostrinia nubilalis*), black cutworm (*Agrotis ipsilon*), fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwest corn borer (*Diatraea grandiosella*), western bean cutworm (Richia albicosta), tobacco budworm (*Heliothis virescens*), Asian corn borer (*Ostrinia nubilalis*), cotton bollworm (*Helicoverpa armigera*), striped stem borer (*Chilo suppressalis*), pink stem borer (*Sesamia calamistis*), rice leaffolder (*Cnaphalocrocis medinalis*), and any combination thereof.

In further embodiments of the method, the chimeric gene comprises any of SEQ ID NOs: 1-3, or a toxin-encoding fragment thereof. In still other embodiments, the produced protein comprises an amino acid sequence of any of SEQ ID NOs: 10-12, or a toxin fragment thereof.

In some embodiments of the method, the chimeric gene comprises a nucleotide sequence that is codon optimized for expression in a plant. In other embodiments, the chimeric gene comprises any of SEQ ID NOs:4-9, or a toxin-encoding fragment thereof. In further embodiments, the produced protein comprises an amino acid sequence of any of SEQ ID NOs:10-15, or a toxin fragment thereof.

In further embodiments, the invention provides a method of producing a pest-resistant (e.g., an insect-resistant) transgenic plant, comprising: introducing into a plant a polynucleotide, a chimeric gene, a recombinant vector, an expression cassette or a nucleic acid molecule of the invention comprising a nucleotide sequence that encodes a Cry protein of the invention, wherein the nucleotide sequence is expressed in the plant, thereby conferring to the plant resistance to at least a lepidopteran insect pest, and producing a insect-resistant transgenic plant. In some embodiments, a pest-resistant transgenic plant is resistant to at least European corn borer (*Ostrinia nubilalis*) or black cutworm (*Agrotis ipsilon*) as compared to a control plant lacking the polynucleotide, chimeric gene, recombinant vector, expression cassette or nucleic acid molecule of the invention. In some embodiments, the introducing is achieved by transforming the plant. In other embodiments, the introducing is achieved by crossing a first plant comprising the chimeric gene, recombinant vector, expression cassette or nucleic acid molecule of the invention with a different second plant.

In some embodiments, a transgenic plant of the invention that is resistant to at least European corn borer (*Ostrinia nubilalis*) or black cutworm (*Agrotis ipsilon*) is further resistant to at least one additional insect, wherein the additional insect includes, but is not limited to, fall armyworm (*Spodoptera frugiperda*), corn earworm (*Helicoverpa zea*), sugarcane borer (*Diatraea saccharalis*), velvetbean caterpillar (*Anticarsia gemmatalis*), soybean looper (*Chrysodeixis includes*), southwestern corn borer (*Diatraea grandiosella*), western bean cutworm (Richia albicosta), tobacco budworm (*Heliothis virescens*), Asian corn borer (*Ostrinia nubilalis*), cotton bollworm (*Helicoverpa armigera*), striped stem borer (*Chilo suppressalis*), pink stem borer (*Sesamia calamistis*) or rice leaffolder (*Cnaphalocrocis medinalis*), and any combination thereof.

In further embodiments, a method of controlling at least a lepidopteran insect pest such as European corn borer (*Ostrinia nubilalis*) or black cutworm (*Agrotis ipsilon*) is provided, the method comprising delivering to the insects an effective amount of a Cry protein of the invention. To be effective, the Cry protein is first orally ingested by the insect. However, the Cry protein can be delivered to the insect in many recognized ways. The ways to deliver a protein orally to an insect include, but are not limited to, providing the protein (1) in a transgenic plant, wherein the insect eats (ingests) one or more parts of the transgenic plant, thereby ingesting the polypeptide that is expressed in the transgenic plant; (2) in a formulated protein composition(s) that can be applied to or incorporated into, for example, insect growth media; (3) in a protein composition(s) that can be applied to the surface, for example, sprayed, onto the surface of a plant part, which is then ingested by the insect as the insect eats one or more of the sprayed plant parts; (4) a bait matrix; or (5) any other art-recognized protein delivery system. Thus, any method of oral delivery to an insect can be used to deliver the toxic Cry proteins of the invention. In some particular embodiments, the Cry protein of the invention is delivered orally to an insect, wherein the insect ingests one or more parts of a transgenic plant.

In other embodiments, the Cry protein of the invention is delivered orally to an insect, wherein the insect ingests one or more parts of a plant sprayed with a composition comprising the Cry proteins of the invention. Delivering the compositions of the invention to a plant surface can be done using any method known to those of skill in the art for applying compounds, compositions, formulations and the like to plant surfaces. Some non-limiting examples of delivering to or contacting a plant or part thereof include spraying, dusting, sprinkling, scattering, misting, atomizing, broadcasting, soaking, soil injection, soil incorporation, drenching (e.g., root, soil treatment), dipping, pouring, coating, leaf or stem infiltration, side dressing or seed treatment, and the like, and combinations thereof. These and other procedures for contacting a plant or part thereof with compound(s), composition(s) or formulation(s) are well-known to those of skill in the art.

In some embodiments, the invention encompasses a method of providing a farmer with a means of controlling a lepidopteran pest, the method comprising supplying or selling to the farmer plant material such as a seed, the plant material comprising a polynucleotide, chimeric gene, expression cassette or a recombinant vector capable of expressing a Cry protein of the invention in a plant grown from the seed, as described above.

Embodiments of this invention can be better understood by reference to the following examples. The foregoing and following description of embodiments of the invention and the various embodiments are not intended to limit the claims, but are rather illustrative thereof. Therefore, it will be understood that the claims are not limited to the specific details of these examples. It will be appreciated by those skilled in the art that other embodiments of the invention may be practiced without departing from the spirit and the scope of the disclosure, the scope of which is defined by the appended claims.

EXAMPLES

Example 1. Identification of Active Bt Strains

*Bacillus thuringiensis* isolates were cultured from spores present in current collections and maintained on T3+ penicillin agar plates. Each isolate was grown aerobically in 24 well deep blocks for about 10 days at 28° C. until sporulation, which was verified by staining with Coomasie blue/acetic acid and visualization with a microscope. After sporulation both the soluble and insoluble fractions were tested for activity against lepidopteran species of interest. Fractions were tested in a surface contamination bioassay, where the fractions were overlaid onto a multispecies artificial diet. Each isolate was screened against at least four lepidopteran species, including *Helicoverpa zea* (corn earworm), *Agrotis ipsilon* (black cutworm), *Ostrinia nubilalis* (European corn borer), and *Spodoptera frugiperda* (fall armyworm) with a sample size of 12 neonate larvae. The duration of each assay was about 7 days at room temperature; the plates were scored for mortality as well as larval growth inhibition. Observed mortality at an increase of 30% over the negative control was considered active. Based on the initial insect testing, strains C0633, C0724 and C1100 were selected for further analysis.

Example 2: Isolation and Sequencing of Bt Genes

Fosmid Genomic Library Construction:

For some Bt strains that were identified in Example 1, genes encoding the putatively active proteins were isolated using a fosmid library method essentially as described in Park et al. (FEMSLett. 284:28-34 (2008). The fosmid library was constructed using a CopyControl™ Fosmid Library Production Kit (Epicentre, Madison, Wis.) according to the manufacturer's protocol. Briefly, purified DNA from each Bt strain (approximately 0.5 µg) was treated enzymatically to end repair the blunt ends, and was then ligated into the fosmid vector pCC1FOS (Epicentre). After in vitro packaging into lambda phages and infection of *Escherichia coli* (*E. coli*) EPI300-T1®, the bacterial cells were plated on Luria-Bertani (LB) that contained 12.5 µg/ml chloramphenicol. The plates were incubated at about 37° C. for 24 h before the selection of colonies. Transfected *E. coli* colonies were transferred to 96-well plates that contained 150 µl of chloramphenicol-containing LB medium and were incubated at 37° C. for 24 h.

Colony Hybridization Screen: A fosmid library was plated at a density of 300 cfu per 100×15 mm L-agar plus 15 g/ml chloramphenicol plate. A total of 3000 fosmids were plated. The filter hybridizations were performed using Immobilon-Ny+ 87 mm filter circles (EMD Millipore, Billerica, Mass.). Colony lifts were completed as follows: filters were placed on plates for about 5 min, then using forceps, filters were lifted from the agar surface and placed colony side up on Whatman filter paper soaked with 0.5 M NaOH for 5 min. Colony filters were then placed on Whatman filter paper soaked in 2×SSC for 5 min. DNA was immobilized to the membrane with a UV Stratalinker® set at 2000×100 µJ (Stratagene, Inc., La Jolla, Calif.). The filters are then air dried on Whatman filter paper. Filters were pre-hybridized and hybridized in 250 mM NaPO4, pH 7.0, 7% SDS, 1% BSA at 65° C. as described by the supplier. Hybridization filters were washed in 2×SSC, 0.5% SDS for 30 min at 65° C., followed by 0.2×SSC, 0.2% SDS for 30 min at 65° C. Filters were exposed to X-ray film (Kodak® BIOMAX® XAR, Fisher Scientific, Pittsburgh, Pa.) overnight with intensifying screens at −80° C. Positive colonies were patched to L agar with plus 15 g/ml chloramphenicol.

Hybridization Probes:

PCR primers were designed to amplify a fragment of a cry2-like gene from the genomic DNA of a Bt strain designated C0633. The primer pair included a forward primer designated OAR2609a having the sequence GTTTAAACATGAATAATGTATTGAATAGCG (SEQ ID NO: 16) and a reverse primer designated OAR2610a having the sequence GGCGCGCCTTAATACAGTGGTAGAAGATTAG (SEQ ID NO: 17). The PCR reaction was run under the following cycle conditions: [94° C., 5 min], 25× [94° C., 30 sec, 55° C., 30 sec, 72° C. 2 min]. The reaction contained 1× One Taq® buffer (New England Biolabs, Beverly, Mass.), 200 m dNTP, 80 ng DNA, 2.5U One Taq® DNA polymerase, 50 ng each primer and sterile distilled water to 50 µl total reaction.

The resulting amplicon was separated on 1% agarose TAE gel containing ethidium bromide. The amplicon was viewed under UV light and cut out of the gel. The DNA was isolated using a gel extraction kit as described by the supplier (Qiagen, Valencia, Calif.). Probes were labeled with EasyTide (α-32P) dCTP 3000 Ci/mmol (Perkin Elmer, Waltham, Mass.) using Rediprime II random prime labeling system (GE Healthcare, Pittsburgh, Pa.). Unincorporated nucleotides were removed using Micro Bio-Spin 30 Chromatography columns (Biorad, Hercules, Calif.). Probes were heated at 95° C. for 5 min before addition to hybridization solution.

Bt Gene Sequencing:

DNA preps for 2-4 independent clones are prepped following the manufacturer's instructions (Qiagen). Sequencing reactions with primers designed to both strands of the predicted nucleotide sequence of interest were carried out using the BigDye™ Terminator Kit (Applied Biosystems, Foster City, Calif.) according to manufacturer's instructions. Reaction products were electrophoresed on ABI373 or ABI377 sequencing instruments. All sequencing data are analyzed using the Phred/Phrap/Consed software package (University of Washington) to an error ratio equal to or less than $10^{-4}$ at the consensus sequence level. The sequence was assembled with the program Sequencher™ (Version 4.7, Gene Codes Corp., Ann Arbor, Mich.). Each gene was sequenced to 4× coverage.

Example 3. Bt Gene Cloning and Synthesis

Cry2-specific primer pairs were designed to facilitate the identification and cloning of cry2-type genes. A primer pair was designed to hybridize to a 5' end of a cry2-type gene with the addition of a PmeI restriction site and to a 3' end with the addition of an AscI restriction site. The 5'forward primer was designated OAR2609a having the sequence GTTTAAACATGAATAATGTATTGAATAGG (SEQ ID NO: 16) and a reverse primer OAR2610a having the sequence GGCGCGCCCTACTCTTGTGTTTCAATAAA (SEQ ID NO: 17). The inserted restriction sites are underlined in the respective primers. The PCR reaction was carried out using the following cycle conditions: 30× [98° C., 10 sec, 55° C., 30 sec, 72° C., 2 min]. The reaction contained 1× Phusion HF buffer, 200 m dNTP, 80 ng DNA, 1U Phusion DNA polymerase (New England Biolabs), 50 ng each primer and sterile distilled water to 50 µl total reaction.

The PCR reaction was cleaned up using the Zymo Research DNA clean and concentrate kit. The DNA was digested with 10 U AscI (New England Biolabs) with 2.4 ug amplicon, 1× Cutsmart buffer in 40 ul and then incubated at 37° C. for 3 hours. The digested DNA was cleaned up using the Zymo Research DNA clean and concentrate kit.

The resulting amplicon was cloned into the TOPO pCR 4.0 vector as described by the supplier (Life Technologies). Isolated plasmid DNA was digested with PmeI and AscI as described by the supplier (New England Biolabs).

The PmeI/AscI fragment was cloned into a shuttle vector designated pCIB5634' designed for expression in both *E. coli* and *B. thuringiensis*. The pCIB5634' vector was digested with PmeI and AscI. The digested vector and the gene fragment were purified by running on a 1% agarose Tris Acetate EDTA buffer based gel. The fragments were cutout from the gel and cleaned up using the QIAGEN gel extraction kit as described by the supplier. The fragments were ligated together using a ligation kit from New England Biolabs as described by the supplier. The ligation reaction was transformed into TOP10 cells (Life Technologies) as described by the supplier and plated on L-agar containing 100 mg/ml ampicillin. Plasmid DNA was isolated from a single colony and the identified clone was sequenced again to 2× coverage to confirm the correct sequence.

Some Bt genes that were selected for recombinant production but were not directly cloned out of genomic DNA were submitted to third party vendors for whole gene synthesis. These synthesized Bt genes were sub-cloned into the above-described shuttle vectors for subsequent expression and testing for further biological activity.

Example 4. Genome Assembly and Analysis

Some Bt cry genes of the invention were isolated from the strains identified in Example 1 using a whole genome sequencing approach. Briefly, *Bacillus* DNA was sheared using a Covaris S2 ultrasonic device (Covaris, Inc., Woburn, Mass.) with the program DNA_400 bp set at duty cycle: 10%; intensity: 4; cycles/burst: 200. The DNA was treated with the NEBNext® Ultra™ End Repair/dA-tailing module (New England Biolabs, Inc. Ipswich, Mass.). Bioscience indexes 1-57 adapters (1-27 Brazil, 28-57 USA, UK and Switzerland) were ligated using NEB Quick Ligation™ as described by the supplier (New England Biolabs, Inc. Ipswich, Mass.). Ligations were cleaned up using Agencourt AMPure XP beads as described by the supplier (Beckman Coulter, Inc., Indianapolis, Ind.).

The library was size fractionated as follows: A 50 uL sample was mixed with 45 ul 75% bead mix (25% AMPure beads plus 75% NaCl/PEG solution TekNova cat # P4136). The mix was stirred and placed on magnetic rack. The resulting supernatant was transferred to a new well and 45 ul 50% bead mix (50% AMPure beads plus 50% NaCl/PEG solution TekNova cat # P4136) was added. This mix was stirred and placed on a magnetic rack. The resulting supernatant was removed and the beads were washed with 80% ethanol. 25 uL of elution buffer (EB) buffer was added and the mix placed on a magnetic rack. The final resulting supernatant was removed and placed in 1.5 mL tube. This method yielded libraries in the 525 DNA base pairs (bp) (insert plus adapter) size range.

The sized DNA library was amplified using KAPA Biosystem HiFi Hot Start (Kapa Biosystems, Inc., Wilmington, Mass.) using the following cycle conditions: [98° C., 45s]; 12×[98° C., 15s, 60° C., 30s, 72° C., 30s]; [72° C., 1 min]. Each reaction contained: 5 ul DNA library, 1 uL Bioscience universal primer (25 uM), 18 uL sterile water, luL Bioscience indexed primer (25 uM), 25 ul 2×KAPA HiFi polymerase.

Libraries were run on the Agilent 2100 Bioanalyzer (Agilent Technologies, Santa Clara, Calif.) using High Sensitivity chips to determine the library size range and average insert size. All libraries were processed for paired end (PE) sequencing (100 cycles per read; 12-24 libraries per lane) on a HiSeq 2500 sequencing system using standard manufacturer's sequencing protocols (Illumina, Inc., San Diego, Calif.).

A *Bacillus* computational analysis tool developed to identify and characterize likely Cry-like genes was used for prioritization of leads for further laboratory testing.

The genome assembly and analysis as well as the genomic library analysis described above led to the identification of three Cry2-like genes in the *Bacillus thuringiensis* strains with toxicity to at least European corn borer (*Ostrinia nubilalis*) or corn earworm (*Helicoverpa zea*). Identifying characteristics of the Cry2-like genes and proteins are shown in Table 1.

TABLE 1

Cry genes/proteins identified in *Bacillus thuringiensis* strains.

| Strain | Protein/ Gene Name | Nearest Cry Family Member | Molecular Weight (kD) | Nucleotide SEQ ID NO: | Amino Acid SEQ ID NO: |
|---|---|---|---|---|---|
| C0633 | BT0016 | Cry2Ba | 70.7 | 1 | 10 |
| C0724 | BT0026 | Cry2Aa | 71.1 | 2 | 11 |
| C1100 | BT0032 | Cry2Aa | 70.8 | 3 | 12 |

Example 5. Homology of BT0016, BT0026 and BT0032 to Known Bt Cry Proteins

A search of protein databases with the amino acid sequences of the proteins of the invention reveal that they are homologous to known insecticidal proteins. Comparison of the amino acid sequences of the proteins of the invention to the non-redundant (nr) database maintained by the NCBI (world wide web at ncbi.nlm.nih.gov) using the BLAST algorithm revealed that the proteins of the invention have the highest identity to proteins in the Cry2 family. More specifically, BT0016 has about 71% identity to Cry2A proteins, example sequences of which may be found at NCBI under accession numbers M31738, M23724, X57252, AF200816, AAQ52362, EF439818, ACH91610 and EU939453, and about 88% identity to Cry2B proteins, example sequences of which may be found at NCBI under accession numbers KC156658 and KF014123. BT0026 has about 77% identity to Cry2A proteins and about 66% identity to Cry2B proteins. BT0032 has about 88% identity to Cry2A proteins and about 72% identity to Cry2B proteins.

Example 6. Bt Protein Expression in Recombinant Host Cells

*Bacillus* Expression. The Cry proteins described in Example 4 were expressed in a crystal minus *Bacillus thuringiensis* (Bt) strain having no observable background insecticidal activity via a shuttle vector designated pCIB5634', designed for expression in both *E. coli* and Bt. Vector pCIB5634' comprises a Cry1Ac promoter that drives expression of the cloned Bt Cry gene and a erythromycin resistance marker. Expression cassettes comprising the Cry coding sequence of interest were transformed into the host Bt strain via electroporation and transgenic Bt strains were selected for on erythromycin containing agar plates. Selected transgenic Bt strains were grown to the sporulation phase in T3 media at 28° C. for 4-5 days. Cell pellets were harvested and washed iteratively before solubilization in high pH carbonate buffer (50 mM) containing 2 mM DTT.

*E. coli* Expression.

Cry proteins were expressed in *E. coli* strains using pET28a or pET29a vectors (Merck KGaA, Darmstadt, Germany). Constructs were transformed by electroporation and transgenic *E. coli* clones were selected for on kanamycin-containing agar plates. Selected transgenic *E. coli* strains were grown and Cry protein expression induced using IPTG induction at 28° C. Cells were resuspended in high pH carbonate buffer (50 mM) containing 2 mM DTT and then broken using a Microfluidics LV-1 homogenizer.

Expression Analysis.

Resulting cell lysates from either transgenic Bt or *E. coli* strains were then clarified via centrifugation and samples were analyzed for purity via SDS-PAGE and electropherogram using a BioRad Experion system (Biorad, Hercules, Calif.). Total protein concentrations were determined via Bradford or Thermo 660 assay. Purified Cry proteins were then tested in bioassays described below.

Example 7. Activity of Cry Proteins in Bioassays

The Cry proteins produced in Example 6 were tested against one or more of the following insect pest species using an art-recognized artificial diet bioassay method: fall armyworm (FAW; *Spodoptera frugiperda*), corn earworm (CEW; *Helicoverpa zea*), European corn borer (ECB; *Ostrinia nubilalis*), black cutworm (BCW; *Agrotis ipsilon*), sugarcane borer (SCB; *Diatraea saccharlis*), velvet bean caterpillar (VBC; *Anticarsia gemmatalis*), soybean looper (SBL; *Pseudoplusia includens*), southwestern corn borer (SWCB; *Diatraea grandiosella*), western bean cutworm (WBCW; *Striacosta albicosta*), tobacco budworm (TBW; *Heliothis virescens*), Asian corn borer (ACB; *Ostrinia nubilalis*), cotton bollworm (CBW; *Helicoverpa armigera*), striped stem borer (SSB; *Chilo suppressalis*), pink stem borer (PSB; *Sesamia inferens*) and rice leaf folder (RLF; *Cnaphalocrocis medinails*).

An equal amount of protein in solution was applied to the surface of an artifical insect diet (Bioserv, Inc., Frenchtown, N.J.) in 24 well plates. After the diet surface dried, larvae of the insect species being tested were added to each well. The plates were sealed and maintained at ambient laboratory conditions with regard to temperature, lighting and relative himidity. A positive-control group consisted of larvae exposed to a very active and broad-spectrum wild-type *Bacillus* strain. Negative control groups consisted of larvae exposed to insect diet treated with only the buffer solution and larvea on untreated insect diet; i.e. diet alone. Mortality was assessed after about 120 hours and scored relative to the controls.

Results are shown in Table 2, where a "−" means no activity compared to the control group, a "+/−" means 0-10% activity compared to check (this category also includes 0% mortality with strong larval growth inhibition), a "+" means 10-25% activity compared to check, a "++" means 26-75% activity compared to check, and a "+++" 76-100% activity compared to check. The designation "nt" in Table 2 means the indicated protein was not tested against that particular pest.

TABLE 2

Results of bioassays with Cry Proteins.

| BT Proteins | Insect Species | | | | | | | | |
|---|---|---|---|---|---|---|---|---|---|
| | FAW | CEW | ECB | BCW | SCB | VBC | SBL | SWCB | TBW |
| 0016 | +/− | +/− | − | − | nt | nt | nt | nt | nt |
| 0026 | − | ++ | − | − | − | nt | nt | nt | nt |
| 0032 | + | +/− | +++ | − | − | +++ | +++ | − | +++ |

Example 8. Vectoring of Genes for Plant Expression

Prior to expression in plants, synthetic polynucleotides comprising a nucleotide sequence encoding the mutant Cry protein, mBT-00032 (SEQ ID NO: 15) was synthesized on an automated gene synthesis platform (Genscript, Inc., Piscataway, N.J.). For this example, a first expression cassette was made comprising a maize ubiquitin promoter (Ubil) operably linked to the Cry protein coding sequence which was operably linked to a Nos terminator and a second expression cassette was made comprising a Ubil promoter operably linked to a phosphomannose isomerase (PMI) coding sequence which was operably linked to a Nos terminator. Expression of PMI allows for positive selection of transgenic plants on mannose. Both expression cassettes were cloned into a suitable vector for *Agrobacterium*-mediated maize transformation.

Example 9. Expression and Activity of Cry Proteins in Maize Plants

Transformation of immature maize embryos was performed essentially as described in Negrotto et al., 2000, Plant Cell Reports 19: 798 803. Briefly, *Agrobacterium* strain LBA4404 (pSB 1) comprising an expression vector described in Example 5 is grown on YEP (yeast extract (5 g/L), peptone (10 g/L), NaCl (5 g/L), 15 g/1 agar, pH 6.8) solid medium for 2-4 days at 28° C. Approximately $0.8\times10^9$ *Agrobacterium* cells are suspended in LS-inf media supplemented with 100 μM As. Bacteria are pre-induced in this medium for approximately 30-60 minutes.

Immature embryos from an inbred maize line are excised from 8-12 day old ears into liquid LS-inf+100 μM As. Embryos are rinsed once with fresh infection medium. *Agrobacterium* solution is then added and embryos are vortexed for 30 seconds and allowed to settle with the bacteria for 5 minutes. The embryos are then transferred scutellum side up to LSAs medium and cultured in the dark for two to three days. Subsequently, between approximately 20 and 25 embryos per petri plate are transferred to LSDc medium supplemented with cefotaxime (250 mg/l) and silver nitrate (1.6 mg/l) and cultured in the dark at approximately 28° C. for 10 days.

Immature embryos, producing embryogenic callus are transferred to LSD1M0.5S medium. The cultures are selected on this medium for approximately 6 weeks with a subculture step at about 3 weeks. Surviving calli are transferred to Reg1 medium supplemented with mannose. Following culturing in the light (16 hour light/8 hour dark regiment), green tissues are then transferred to Reg2 medium without growth regulators and incubated for about 1-2 weeks. Plantlets are transferred to Magenta GA-7 boxes (Magenta Corp, Chicago Ill.) containing Reg3 medium and grown in the light. After about 2-3 weeks, plants are tested for the presence of the PMI genes and the Bt cry gene by PCR. Positive plants from the PCR assay are transferred to a greenhouse for further evaluation.

Transgenic plants from 14 independent events were evaluated for copy number (determined by Taqman analysis), protein expression level (determined by ELISA), and efficacy against insect species of interest in leaf excision bioassays. Specifically, plant tissue was excised from single copy events (V3-V4 stage) and infested with neonate larvae of a target pest, then incubated at room temperature for about 5 days. Leaf disks from transgenic plants expressing BT-0032 were tested against European corn borer (*Ostrinia nubilalis*), corn earworm (*Helicoverpa zea*), fall armyworm (*Spodoptera frugiperda*) and tobacco budworm (*Heliothis virescens*).

Results of the bioassay confirmed that stably transformed plants expressing the BT-0032 Cry2-like protein in the range of 4.12-13.1 μg/gfw are active against corn earworm (*Helicopverpa zea*) and tobacco budworm (*Heliothis virescens*).

What is claimed is:

1. A chimeric gene comprising a heterologous promoter operably linked to a nucleic acid molecule comprising a nucleotide sequence that encodes a Cry protein that is toxic to a lepidopteran pest, wherein the nucleotide sequence (a) encodes a Cry protein comprising an amino acid sequence that has at least 99% sequence identity with SEQ ID NO:12, or a toxin fragment thereof; or (b) is a synthetic sequence of (a) that has codons optimized for expression in a transgenic organism.

2. The chimeric gene of claim 1, wherein the nucleotide sequence comprises SEQ ID NO:3, or a toxin-encoding fragment thereof.

3. The chimeric gene of claim 1, wherein the Cry protein comprises the amino acid sequence of SEQ ID NO:12, or a toxic fragment thereof.

4. The chimeric gene of claim 1, wherein the synthetic nucleotide sequence comprises SEQ ID NO:6, or a toxin-encoding fragment thereof.

5. The chimeric gene of claim 1, wherein the heterologous promoter is a plant expressible promoter.

6. The chimeric gene of claim 5, wherein the plant expressible promoter is selected from the group of promoters consisting of ubiquitin, cestrum yellow virus, corn TrpA, OsMADS 6, maize H3 histone, corn sucrose synthetase 1, corn alcohol dehydrogenase 1, corn heat shock protein, maize mtl, pea small subunit RuBP carboxylase, rice actin, rice cyclophilin, Ti plasmid mannopine synthase, Ti plasmid nopaline synthase, petunia chalcone isomerase, bean glycine rich protein 1, potato patatin, lectin, CaMV 35S and S-E9 small subunit RuBP carboxylase promoter.

7. A Cry protein encoded by the chimeric gene of claim 1, wherein the Cry protein comprises the amino acid sequence of SEQ ID NO:15.

8. An insecticidal composition comprising the Cry protein of claim 7 and an agriculturally acceptable carrier.

9. A recombinant vector comprising the chimeric gene of claim 1.

10. A transgenic bacterial or plant cell comprising the recombinant vector of claim 9.

11. The transgenic plant cell of claim 10, wherein the plant cell is a) a dicot plant cell; or b) a monocot plant cell; or c) a dicot plant cell selected from the group consisting of a soybean cell, sunflower cell, tomato cell, cole crop cell, cotton cell, sugar beet cell and tobacco cell; or d) a monocot plant cell selected from the group consisting of a barley cell, maize cell, oat cell, rice cell, sorghum cell, sugar cane cell and wheat cell.

12. A transgenic plant comprising the transgenic plant cell of claim 11, wherein the plant is a) a dicot plant; or b) a monocot plant; or c) a dicot plant selected from the group consisting of a soybean plant, sunflower plant, tomato plant, cole crop plant, cotton plant, sugar beet plant and a tobacco plant; or d) a monocot plant selected from the group consisting of a barley plant, maize plant, oat plant, rice plant, sorghum plant, sugar cane plant and a wheat plant.

13. A transgenic seed of the transgenic plant of claim 12, wherein said seed comprises the chimeric gene.

14. A harvested product derived from the transgenic plant of claim 12, wherein the harvested product comprises the chimeric gene.

15. A method of producing an insect-resistant transgenic plant, comprising: introducing into a plant the chimeric gene of claim 1, wherein the Cry protein is expressed in the plant, thereby producing an insect-resistant transgenic plant.

16. The method of claim 15, wherein the introducing step is achieved by a) transforming the plant; or b) crossing a first plant comprising the chimeric gene with a different second plant.

17. The method of claim 16 wherein the plant is a maize plant.

18. A method of controlling a lepidopteran pest, comprising delivering to the lepidopteran pest or an environment thereof a composition comprising an effective amount of the Cry protein of claim 7.

* * * * *

SEQUENCE LISTING

<160> NUMBER OF SEQ ID NOS: 17

<210> SEQ ID NO 1
<211> LENGTH: 1875
<212> TYPE: DNA
<213> ORGANISM: Bacillus thuringiensis

<400> SEQUENCE: 1

```
atgaataatg tattgaatag cgaaagacct actaagtgtg atgcgtataa cgtagtggct      60
catgatccat ttagttttga acataaatca gtagatacca tacaaaaaga atgggtggag     120
tggaaaagaa ccgatcatag tttatacgta tctcctattg tgggaactat agctaagttt     180
ctgctaaaga aaataggggg acttattgga aaaaggatat taagtgagtt aaagaattta     240
attttttccta gtggtagtac agcgtcaatg caagatattt taagaggagc agaacaattt     300
ttaaatcaaa gacttgatga agacaccttt gctcgtgtag aggcagaatt gagagggctt     360
caagcaaatg tagaggaatt taatcgacaa gtggacaatt ttttaaaccc aaatcaaacc     420
cctgttcctt tagcgataat cgattcggtt aatacattgc aacaattatt cttaagtaga     480
ttaccccagt tccagataca acgctatcag ctattattat tacctttatt tgcacaagca     540
gctaatttac atcttacttt tattcgagat gttattctta atgcagatga atggggaata     600
ccagaagcaa cggtgcgcac atatagacag cacctacaaa gatatacaca ggattactcc     660
aattattgta taaatacgta ccaaactgct ttccgggggtt taaacactcg tttacatgat     720
atgttagagt ttagaacatt tatgtttta aatgtattag actatgtatc catctggtcg     780
ttgtttaaat atcaaagtct gatggttact tcaactgcca atttatatgc ttcgggaagt     840
ggcagtaatc aattttttcac tgcacaagcc tggccatttt tatattccct cttccaggtt     900
aattcaaatt atataatgtc taattttggt ggtaaccgag agactgctac tgctggtgtt     960
cctggtttag ggggattttt attcaattt ttatttagtt ttagggttaa ttatactgga    1020
ggagtttcat ctggtctcct aggtgttgag ggaattttaa acaactttag ttgcaactcc    1080
tctttatcaa caccaattgt aagaagttgg ctggattcag gtatagaacg aagcgatatt    1140
caacataatt ggcgtacaga tatgtttctg agggctaatg gtgtaccttg tggtgctttt    1200
ccattaactc ttgttatgta tccaaatgtg acaatgaatt atttttcctga ttatttcatt    1260
cgtaacattt ccggaattat tcaaaatatt gataacatga atttgagtag accattacac    1320
tttaatgaag taagagattt aagaggcaat gaagttgcta ctttggtatc tgtgcatagt    1380
acaaaaaata atatctatgc tgcccatgaa aatggtacta tgattcattt ggcaccggaa    1440
gattatacag gtttcacaat gtcaccaata catgcaactc aagtgaataa tcagactcga    1500
acgtttattt ctgaaaaatt tggaaatcaa ggtgattcct tgagatttga gcaaactaac    1560
acaaccgctc gttatacgtt tagagggaat ggtaataatt ataatcttta tttaagagta    1620
tcatctcaag gaaattccaa tattcgagtt actataaatg gtagaaatta tactgtttca    1680
aatgttaata ctactacaaa taatgatgga gtacttgata tgaagctcg tttttcagat    1740
attcttattg ggaatgtagt ggcaagtgct aatactaatg taccttaga tataaatgtg    1800
acatttaaca ccgtacaaa atttgagctt atgaatatta tgtttgtgcc aactaatctt    1860
ctaccactgt attaa                                                    1875
```

<210> SEQ ID NO 2
<211> LENGTH: 1896
<212> TYPE: DNA
<213> ORGANISM: Bacillus thuringiensis

<400> SEQUENCE: 2

| | |
|---|---|
| atgaataatg tattaaatag cggaagaact accatttgtg atgggcataa cgtaatggct | 60 |
| caggatccct ttagttttca acataaatca ttagatacta tacaaaaaga atggacggaa | 120 |
| tggaaaagag atgatcatag tttatatgta gctcctgttg ttggaactgt tgcaatttt  | 180 |
| ctgctaaaga aattgggggg gttcgctgca aaaggatat tgaatgggtt atgggattta  | 240 |
| gtatttccta atgataatac caaactaatg caagatattt aagagagac agaaaaattt  | 300 |
| ctaaaccaaa gacttaatgc agacactctt tctcgagtaa atgcagaatt ggaggggctt | 360 |
| caaaaaaatg tagcggagtt aatagacaa gtggataatt ttttaaatcc taatcgaaac  | 420 |
| ccgactcttt tatcaataac ttctccagtt aatacaatgc aacaattgtt cctaaataga | 480 |
| ttaacgcagt ccagttacg aggatacgag ctgttattat accttttatt tgcacaagca  | 540 |
| gccaatttac atctttcctt tattagggac gttattctga atgcagagga atggggggatt | 600 |
| tcagcagcaa cgttacgcac atatcgaggt tacctaaaag actatacaaa agaatactct | 660 |
| aattattgta taaatacgta tcaaaccgca tttaaaaagt taaatactcc tttacacgaa | 720 |
| atgttagagt ttagaacata tatgtttta aatgtatttg aatatgtatc catttggtca  | 780 |
| ttgtttaagt atcagagtct tctggtatct tctggcgcaa atttatatgc tagtggtagt  | 840 |
| gggccacagc agaaacaatc atttagcgcg cagaactggc catttttata ttccctttc  | 900 |
| caagtgaatt ctaattatgt attaactggt tttagtggtt ttaggaattc ttttaccatg  | 960 |
| cctaatattg gtggttttccc cggttctact acaactcacg cattgtttag tcgagggct  | 1020 |
| aattatagtg gaggaatttc atctggtatc ataggggatga ctaatagtaa tcacaacttt | 1080 |
| aattgtagca ccgcttcttt acaaacacca tatactagaa gttggctgga ttcaggtaga | 1140 |
| gatcaacatg ccattaatac ctttacagat tggcagacag aatgttttca aacaacttcg | 1200 |
| gattcctggt gtggtgcctt tgtccccccgt ggtaatacga attatttccc agattatttt | 1260 |
| attcgtaata tttctggagt ttctttagtt gtcgggaatg aagatttaag aagaccgtta  | 1320 |
| cactataatg aaataagaaa tatagcaagt ccttccggaa ccctggtgg agggcgagct  | 1380 |
| tatatggcat ctgtgcacaa cagaaaaat aatatctatg ccgctcatga aatggtact   | 1440 |
| atgattcatt tggcgccgga tgataataca gggtttatta tatcgccgat acatgcaaca | 1500 |
| caagtaaata cgcagaatcg aacatttatt tccgagaaat ttggaaatca aggtgattcc | 1560 |
| ttacgatttg aacaaacaaa cacaacagct cgatacacat tagggggaaa gggcaatagt | 1620 |
| tataatctgt atttaagagt atcatcttta ggaaattcca ctattcgagt tacgataaac | 1680 |
| ggtaaggttt atactgttcc aaatgttaat accactacaa ataatgatgg ggttattgat  | 1740 |
| aatggatcac gttttcaga tgtttacatc ggtaacgtag tagcaaatga taagacgaat  | 1800 |
| gtaccgttag atataaatgt gacatttaat tctggtactc aatttgagct tatgaatatt | 1860 |
| atgtgtattc caactaatat tacaccactt tattaa | 1896 |

<210> SEQ ID NO 3
<211> LENGTH: 1902
<212> TYPE: DNA
<213> ORGANISM: Bacillus thuringiensis

<400> SEQUENCE: 3

| | |
|---|---|
| atgaatagtg tattgaatag cggaagaact actatttgtg atgcgtataa tgtagcggct | 60 |
| catgatccat ttagttttca acacaaatca ttagataccg tacaaaagga atggacggag | 120 |

```
tggaaaaaaa ataatcatag tttataccta gatcctattg ttggaactgt ggctagtttt 180
ctgttaaaga aagtggggag tcttgttgga aaaaggatac taagtgagtt acggaattta 240
atatttccta gtggtagtac aaatctaatg caagatattt taagggagac agaacaattc 300
ctaaatcaaa gacttaatac agataccctt gctcgtgtaa atgcagaatt gatagggctc 360
caagcgaata taagggagtt taatcaacaa gtagataatt ttttaaaccc tactcaaaac 420
cctgttcctt tatcaataac ttcttcggtt aatacaatgc agcaattatt tctaaataga 480
ttaccccagt tccagataca aggataccaa ctgttattat taccttttatt tgcacaggca 540
gccaatttac atctttcttt tattagagat gttattctta atgcagatga atggggtatt 600
tcagcagcaa cattacgtac gtatcgagat tacctgagaa attatacaag agattattct 660
aattattgta taaatacgta tcaaactgcg tttagagggt taaacacccg tttacacgat 720
atgttagaat ttagaacata tatgttttta aatgtatttg aatatgtatc catttggtca 780
ttgtttaaat atcagagtct tatggtatct tccggtgcta atttatatgc aagtggtagt 840
ggaccacagc agacccaatc atttacttca caagactggc catttttata ttctcttttc 900
caagttaatt cgaattatat attatctggt attagtggta ctaggctttc tattaccttc 960
cctaatattg gtggtttacc gggtagtact acaactcatt cattgaatag tgccagggtt 1020
aattatagcg gaggagtttc atctggtctc ataggggcga ctaatctcaa tcacaacttt 1080
aattgcagca cggtcctccc tcctttatca acaccatttg ttagaagttg gctggattca 1140
ggtacagatc gagagggcgt tgctacctct acgaattggc agacagaatc ctttcaaaca 1200
actttaagtt taaggtgtgg tgctttttca gcccgtggaa attcaaacta tttcccagat 1260
tattttatcc gtaatatttc tggggttcct ttagttatta gaaacgaaga tctaacaaga 1320
ccgttacact ataaccaaat aagaaatata gaaagtcctt cgggaacacc tggtggagca 1380
cgggcctatt tggtatctgt gcataacaga aaaaataata tctatgccgc taatgaaaat 1440
ggtactatga tccatttggc gccagaagat tatacaggat ttactatatc gccaatacat 1500
gccactcaag tgaataatca aactcgaaca tttatttctg aaaaatttgg aaatcaaggt 1560
gattctttaa ggtttgaaca aaacaacacg acagctcgtt atacgcttag agggaatgga 1620
aatagttaca atctttattt aagagtttct tcaataggaa attccactat tcgagttact 1680
ataaacggta gggtatatac tgctacaaat gttaatacta ctacaaataa cgatggagtt 1740
aatgataatg gagcccgttt ttcagatatt aatatcggta atatagtagc aagtagtaat 1800
tctgatgtac cattagatat aaatgtaaca ttaaactccg gtactcaatt tgatcttatg 1860
aatattatgc ttgtaccaac taatatttca ccactttatt aa 1902
```

<210> SEQ ID NO 4
<211> LENGTH: 1872
<212> TYPE: DNA
<213> ORGANISM: Artificial Sequence
<220> FEATURE:
<223> OTHER INFORMATION: Codon optimized version of BT-0016

<400> SEQUENCE: 4

```
atgaacaatg tgctcaacag cgagcgccca acgaagtgcg acgcttacaa cgtggtcgcc 60
cacgatcctt tctcattcga gcataagtcc gtggacacta tccagaagga gtgggtcgag 120
tggaagagga ccgatcactc cctctacgtg agcccgatcg tcggcaccat tgccaagttc 180
ctcctgaaga agatcggtgg cctgattggc aagcgcatcc tcagcgagct gaagaacctc 240
attttcccca gcgggtcgac ggcttcgatg caggacatcc tgaggggcgc cgagcagttc 300
```

```
ctgaaccaga ggctcgacga ggatacattc gccagggtgg aggctgagct gaggggcctc    360
caggctaacg tggaggagtt caatcgccag gttgacaact tcctgaaccc aaatcagacg    420
ccggttcccc tcgcgatcat tgattcagtg aacacactgc agcagctctt cctgtcccgg    480
ctcccgcagt tccagatcca gcgctaccag ctgctcctcc tgccactctt cgctcaggct    540
gcgaacctcc acctgacatt cattcgggac gtcatcctga acgccgatga gtggggcatc    600
cctgaggcga cggttcgcac atacaggcag catctccagc gctacaccca ggactactcc    660
aactactgca tcaatactta ccagacggcg ttccgcggcc tgaacaccag gctccacgac    720
atgctggagt tcaggacatt catgttcctg aacgttctcg attacgtgag catctggtcg    780
ctgttcaagt accagagcct catggtgacg tcgacagcca atctgtacgc gtctggctca    840
gggtccaacc agttcttcac ggcgcaggct tggccattcc tgtactccct cttccaggtg    900
aactctaatt acatcatgtc aaacttcggt ggcaacaggg agactgcgac ggccggcgtc    960
cctgggctcg gcgggttcct gttcaatttc ctcttcagct tcagggtgaa ctacaccggc   1020
ggggtctcca gcggcctcct gggggtggag ggcattctga acaatttctc ctgcaactcg   1080
tctctcagca ctccaatcgt ccgctcgtgg ctggactctg gcattgagag gtcggatatc   1140
cagcacaatt ggaggacgga catgttcctg agggccaacg ggtgccatg  cggcgctttc   1200
cctctcacgc tggtcatgta cccaaacgtt accatgaact acttccctga ctacttcatc   1260
aggaatattt ctggcatcat tcagaacatc gataacatga atctgtcacg gcccctccac   1320
ttcaatgagg tccgggacct gaggggcaac gaggttgcca ctctcgtctc tgttcattca   1380
accaagaaca atatctacgc tgcccacgag aacgggacta tgatccatct cgcgccggag   1440
gactacacgg gcttcacaat gtccccatt  catgctaccc aggtcaacaa tcagacgcgg   1500
acattcatct cggagaagtt cgggaaccag ggcgattctc tgcgcttcga gcagacgaac   1560
accacggcca ggtacacatt ccggggcaat gggaacaatt acaacctcta cctgcgcgtt   1620
tcatcccagg ggaactctaa tattcgcgtg actatcaacg gcaggaatta cacctccaac   1680
gtgaatacaa ctaccaacaa tgacggggtc ctcgataacg aggcgaggtt cagcgacatc   1740
ctgattggca acgttgtggc ttcggccaac actaatgttc cgctggatat taacgtgacc   1800
ttcaatactg gcaccaagtt cgagctgatg aacatcatgt tcgtcccgac caacctcctg   1860
cccctgtact aa                                                       1872
```

```

<210> SEQ ID NO 5
<211> LENGTH: 1896
<212> TYPE: DNA
<213> ORGANISM: Artificial Sequence
<220> FEATURE:
<223> OTHER INFORMATION: Codon optimized version of BT-0026.

<400> SEQUENCE: 5
atgaacaatg ttctgaattc cgggaggacc accatctgcg acggccacaa cgtgatggcc     60
caggacccgt tctccttcca gcataagtcg ctcgacacca ttcagaagga gtggacggag    120
tggaagaggg acgatcactc gctctacgtg gctccggtgg tgggcaccgt cgccatcttc    180
ctcctgaaga agctcggcgg gttcgccgcg aagaggattc tcaacggcct gtgggacctc    240
gtcttcccga acgataatac caagctcatg caggacatcc tgcgggagac ggagaagttc    300
ctgaatcaga ggctcaacgc ggatacgctg tcgagggtga acgctgagct ggagggcctc    360
cagaagaacg ttgcggagtt caatcggcag gtggacaact tcctcaaccc gaatcgcaac    420
```

```
cccactctcc tgtcaatcac ctccccagtc aatacgatgc agcagctctt cctgaaccgc      480
ctcacccagt tccagctgag gggctacgag ctgctgctcc tgcctctgtt cgctcaggct      540
gccaacctcc atctgtcttt catccgcgac gtgattctca acgccgagga gtggggatc       600
tcagcggcta cactccggac ttaccgcggc tacctgaagg attacaccaa ggagtactcc      660
aattactgca tcaacaccta ccagacggcc ttcaagaagc tgaacacacc actccacgag      720
atgctggagt tcaggactta catgttcctc aacgtgttcg agtatgtgtc catctggtcg      780
ctgttcaagt accagagcct cctggtctcc agcggcgcta acctctacgc ctcggggtcg      840
ggcccgcagc agaagcagtc tttctcagcc cagaactggc ccttcctgta ctccctcttc      900
caggttaata gcaactacgt gctgaccggg ttctctggct tccgcaattc attcacgatg      960
ccaaacatcg gtggcttccc tggctccaca actacccacg cgctcttctc ggctagggcc     1020
aactactctg gcgggatctc gtctgggatc attggcatga caaatagcaa ccataatttc     1080
aactgctcta ctgcgtcact ccagacaccg tacactcggt catggctgga ctccggccgc     1140
gatcagcacg ctatcaacac cttcacggac tggcagaccg agtgcttcca gacgacatcc     1200
gattcgtggt gcggggcttt cgtcccccagg gcaatacga actacttccc cgactacttc     1260
atcaggaata tttccggggt gagcctggtt gtgggcaacg aggatctccg caggcccctg     1320
cattacaatg agatccgcaa cattgcgtcc ccgtctggca ccctggcgg gggccgcgcg     1380
tacatggctt cggtccacaa caggaagaac aatatctacg ccgcgcacga gaacggcaca     1440
atgattcatc tcgccccaga cgataacacg ggcttcatca tttctcctat ccacgcgaca     1500
caagtgaata ctcagaaccg gaccttcatt tcagagaagt cgggaaccca gggcgactcc     1560
ctgcgcttcg agcagacaaa cactaccgcc aggtacactt tccggggggaa gggcaatagc     1620
tacaacctct acctgagggt ctcatccctc gggaattcga cgatccgggt tacaattaac     1680
ggcaaggtgt acaccgtccc aaatgttaac acgacaacta acaatgacgg cgtgatcgat     1740
aacggctcgc gcttctctga cgtctacatt ggcaatgtcg ttgcgaacga caagacgaat     1800
gtccctctgg atatcaacgt tacattcaat agcggcactc agttcgagct gatgaacatc     1860
atgtgcattc cgaccaacat tacgcccctg tactaa                              1896

<210> SEQ ID NO 6
<211> LENGTH: 1899
<212> TYPE: DNA
<213> ORGANISM: Artificial Sequence
<220> FEATURE:
<223> OTHER INFORMATION: Codon optimized version of BT-0032.

<400> SEQUENCE: 6
atgaactcgg ttctgaatag cgggaggacg acgatttgcg atgcctacaa tgttgcggcc       60
cacgaccct tctctttcca gcacaagtct ctcgacacag tccagaagga gtggactgag      120
tggaagaaga acaatcactc cctctacctc gacccgatcg ttggcaccgt ggcctcattc      180
ctcctgaaga aggtcggctc cctggtcggc aagcgcatcc tcagcgagct gcgcaacctc      240
attttcccgt ccggcagcac aaatctcatg caggacatcc tgcgcgagac tgagcagttc      300
ctgaaccaga ggctcaatac agatactctc gcgcgggtta acgctgagct gatcggcctc      360
caggcgaaca ttagggagtt caatcagcag gtggacaact tcctcaatcc aacccagaac      420
ccagttcctc tgagcatcac ctccagcgtg aacacgatgc agcagctctt cctgaatagg      480
ctcccccagt tccagattca gggctaccag ctcctgctcc tgccactgtt cgctcaggcc      540
gcgaacctcc acctgagctt catccgggac gtgattctga acgcggatga gtggggcatc      600
```

```
tcggctgcca cactccgcac ttacagggac tacctgcgga actacacgcg cgattacagc    660
aactactgca tcaataccta ccagacggcc ttccgcggcc tgaacaccag gctccatgac    720
atgctggagt tccgcacgta catgttcctc aacgttttcg agtatgtgtc catctggtcg    780
ctcttcaagt accagtccct gatggtctcg tctggcgcta acctgtacgc ttcgggctct    840
gggcctcagc agacccagtc tttcacgtca caggactggc cgttcctgta ctctctcttc    900
caggtgaact caaattacat cctctccggc attagcggga cacgcctgtc aatcactttc    960
ccaaacattg gcgggctccc aggctccacc acgacacact cgctgaactc tgccagggtc   1020
aattactccg gcggggtttc atccggcctc atcggggcga ccaacctgaa tcataacttc   1080
aattgctcga ccgtcctgcc accactctct acgccattcg ttcgctcatg gctcgactcc   1140
ggcacagata gggagggggt cgctaccagc acgaactggc agactgagtc cttccagact   1200
accctcagcc tgcgctgcgg cgctttcagc gctaggggga actcgaatta cttcccggac   1260
tacttcatcc ggaacatttc cggcgtcccc ctggttatca ggaacgagga tctcacacgg   1320
ccactgcact acaaccagat ccgcaatatt gagtcaccat ccggcacgcc cggcggcgcc   1380
agggcttacc tcgtgagcgt ccataaccgc aagaacaata tctacgcggc taacgagaat   1440
ggcaccatga ttcacctggc gccagaggac tacacagggt tcactatctc gcctattcat   1500
gctacgcagg tcaacaatca gacaaggact ttcatctcgg agaagttcgg caaccagggg   1560
gattctctcc ggttcgagca gaacaatacg acagccaggt acaccctgcg gggcaacggg   1620
aattcttaca acctctacct gcgcgtgtcc tccatcggca actcaacaat ccgcgtgact   1680
attaatggga gggtctacac cgcgacgaac gttaatacta ccacgaacaa tgacggcgtg   1740
aacgataatg ggctaggtt cagcgacatc aacattggca atatcgtcgc ctcttcaaac    1800
agcgacgtgc cgctcgatat taacgtcacc ctgaattcgg gcacgcagtt cgatctcatg   1860
aacatcatgc tggtgccaac caatatttcc cctctctac                          1899


<210> SEQ ID NO 7
<211> LENGTH: 1872
<212> TYPE: DNA
<213> ORGANISM: Artificial Sequence
<220> FEATURE:
<223> OTHER INFORMATION: Codon optimized version of mutant BT-0016

<400> SEQUENCE: 7
atgaacaatg tgctcaacag cgagcgccca accaagtgcg acgcttacaa cgtggtcgcc     60
cacgatcctt tctcattcga gcataagtcc gtggacacta tccagaagga gtgggtcgag    120
tggaagagga ccgatcactc cctctacgtg agcccgatcg tcggcaccat tgccaagttc    180
ctcctgaaga agatcggtgg cctgattggc aagcgcatcc tcagcgagct gaagaacctc    240
attttcccca gcgggtcgac ggcttcgatg caggacatcc tgaggggcgc cgagcagttc    300
ctgaaccaga ggctcgacga ggatacattc gccagggtgg aggctgagct gaggggcctc    360
caggctaacg tggaggagtt caatcgccag gttgacaact tcctgaaccc aaatcagacg    420
ccggttcccc tcgcgatcat tgattcagtg aacacactgc agcagctctt cctgtcccgg    480
ctcccgcagt tccagatcca gcgctaccag ctgctcctcc tgccactctt cgctcaggct    540
gcgaacctcc acctgacatt cattcgggac gtcatcctga acgccgatga gtggggcatc    600
cctgaggcga cggttcgcac atacaggcag catctccagc gctacaccca ggactactcc    660
aactactgca tcaatactta ccagacggcg ttccgcggcc tgaacaccag gctccacgac    720
```

-continued

```
atgctggagt tcaggacatt catgttcctg aacgttctcg attacgtgag catctggtcg    780
ctgttcaagt accagagcct catggtgacg tcgacagcca atctgtacgc gtctggctca    840
gggtccaacc agttcttcac ggcgcaggct tggccattcc tgtactccct cttccaggtg    900
aactctaatt acatcatgtc aaacttcggt ggcaacaggg agactgcgac ggccggcgtc    960
cctgggctcg gcgggttcct gttcaatttc ctcttcagct tcagggtgaa ctacaccggc   1020
ggggtctcca gcggcctcct gggggtggag ggcattctga acaatttctc ctgcaactcg   1080
tctctcagca ctccaatcgt ccgctcgtgg ctggactctg gcattgagag gtcggatatc   1140
cagcacaatt ggaggacgga catgttcctg agggccaacg gggtgccatg cggcgctttc   1200
cctctcacgc tggtcatgta cccaaacgtt accatgaact acttccctga ctacttcatc   1260
aggaatattt ctggcatcat tcagaacatc gataacatga atctgtcacg gcccctccac   1320
ttcaatgagg tccgggacct gaggggcaac gaggttgcca ctctcgtctc tgttcattca   1380
accaagaaca atatctacgc tgcccacgag aacgggacta tgatccatct cgcgccggag   1440
gactacacgg gcttcacaat gtcccccatt catgctaccc aggtcaacaa tcagacgcgg   1500
acattcatct cggagaagtt cgggaaccag ggcgattctc tgcgcttcga gcagacgaac   1560
accacggcca ggtacacatt ccggggcaat gggaacaatt acaacctcta cctgcgcgtt   1620
tcatcccagg ggaactctaa tattcgcgtg actatcaacg gcaggaatta cacctccaac   1680
gtgaatacaa ctaccaacaa tgacggggtc ctcgataacg aggcgaggtt cagcgacatc   1740
ctgattggca acgttgtggc ttcggccaac actaatgttc cgctggatat taacgtgacc   1800
ttcaatactg gaaccaagtt cgagctgatg aacctcatgt tcgtcccgac caacatcctg   1860
cccctgtact aa                                                        1872

<210> SEQ ID NO 8
<211> LENGTH: 1896
<212> TYPE: DNA
<213> ORGANISM: Artificial Sequence
<220> FEATURE:
<223> OTHER INFORMATION: Codon optimized version of mutant BT-0026.

<400> SEQUENCE: 8
atgaacaatg ttctgaattc cgggaggacc accatctgcg acggccacaa cgtgatggcc     60
caggacccgt tctccttcca gcataagtcg ctcgacacca ttcagaagga gtggacggag    120
tggaagaggg acgatcactc gctctacgtg gctccggtgg tgggcaccgt cgccatcttc    180
ctcctgaaga agctcggcgg gttcgccgcg aagaggattc tcaacggcct gtgggacctc    240
gtcttcccga acgataatac caagctcatg caggacatcc tgcgggagac ggagaagttc    300
ctgaatcaga ggctcaacgc ggatacgctg tcgagggtga acgctgagct ggagggcctc    360
cagaagaacg ttgcggagtt caatcggcag gtggacaact tcctcaaccc gaatcgcaac    420
cccactctcc tgtcaatcac ctccccagtc aatacgatgc agcagctctt cctgaaccgc    480
ctcacccagt tccagctgag ggctacgag ctgctgctcc tgcctctgtt cgctcaggct    540
gccaacctcc atctgtcttt catccgcgac gtgattctca acgccgagga gtgggggatc    600
tcagcggcta cactccggac ttaccgcggc tacctgaagg attacaccaa ggagtactcc    660
aattactgca tcaacaccta ccagacggcc ttcaagaagc tgaacacacc actccacgag    720
atgctggagt tcaggacata catgttcctc aacgtgttcg agtatgtgtc catctggtcg    780
ctgttcaagt accagagcct cctggtctcc agcggcgcta acctctacgc ctcggggtcg    840
ggcccgcagc agaagcagtc tttctcagcc cagaactggc ccttcctgta ctccctcttc    900
```

```
caggttaata gcaactacgt gctgaccggg ttctctggct tccgcaattc attcacgatg 960
ccaaacatcg gtggcttccc tggctccaca actacccacg cgctcttctc ggctagggcc 1020
aactactctg gcgggatctc gtctgggatc attggcatga caaatagcaa ccataatttc 1080
aactgctcta ctgcgtcact ccagacaccg tacactcggt catggctgga ctccggccgc 1140
gatcagcacg caatcaacac cttcacggac tggcagaccg agtgcttcca gacgacatcc 1200
gattcgtggt gcggggcttt cgtccccagg ggcaatacga actacttccc cgactacttc 1260
atcaggaata tttccggggt gagcctggtt gtgggcaacg aggatctccg caggcccctg 1320
cattacaatg agatccgcaa cattgcgtcc ccgtctggca cccctggcgg gggccgcgca 1380
tacatggctt cggtccacaa caggaagaac aatatctacg ccgcgcacga gaacggcaca 1440
atgattcatc tcgccccaga cgataacacg ggcttcatca tttctcctat ccacgcgaca 1500
caagtgaata ctcagaaccg gaccttcatt tcagagaagt tcgggaacca gggcgactcc 1560
ctgcgcttcg agcagacaaa cactaccgcc aggtacactt tccgggggaa gggcaatagc 1620
tacaacctct acctgagggt ctcatccctc gggaattcga cgatccgggt tacaattaac 1680
ggcaaggtgt acaccgtccc aaatgttaac acgacaacta acaatgacgg cgtgatcgat 1740
aacggctcgc gcttctctga cgtctacatt ggcaatgtcg ttgcgaacga caagacgaat 1800
gtccctctgg atctcaacgt tacattcaat agcggcactc agttcgagct gatgaacctc 1860
atgtgcattc caaccaacat tacgcccctg tactaa 1896

<210> SEQ ID NO 9
<211> LENGTH: 1902
<212> TYPE: DNA
<213> ORGANISM: Artificial Sequence
<220> FEATURE:
<223> OTHER INFORMATION: Codon optimized version of mutant BT-0032.

<400> SEQUENCE: 9
atgaactcgg ttctgaatag cgggaggacg acgatttgcg atgcctacaa tgttgcggcc 60
cacgacccct tctctttcca gcacaagtct ctcgacacag tccagaagga gtggactgag 120
tggaagaaga acaatcactc cctctacctc gacccgatcg ttggcaccgt ggcctcattc 180
ctcctgaaga aggtcggctc cctggtcggc aagcgcatcc tcagcgagct gcgcaacctc 240
attttcccgt ccggcagcac aaatctcatg caggacatcc tgcgcgagac tgagcagttc 300
ctgaaccaga ggctcaatac agatactctc gcgcgggtta acgctgagct gatcggcctc 360
caggcgaaca ttagggagtt caatcagcag gtggacaact tcctcaatcc aacccagaac 420
ccagttcctc tgagcatcac ctccagcgtg aacacgatgc agcagctctt cctgaatagg 480
ctcccccagt tccagattca gggctaccag ctcctgctcc tgccactgtt cgctcaggcc 540
gcgaacctcc acctgagctt catccgggac gtgattctga acgcggatga gtggggcatc 600
tcggctgcca cactccgcac ttacagggac tacctgcgga actacacgcg cgattacagc 660
aactactgca tcaataccta ccagacggcc ttccgcggcc tgaacaccag gctccatgac 720
atgctggagt tccgcacata catgttcctc aacgttttcg agtatgtgtc catctggtcg 780
ctcttcaagt accagtccct gatggtctcg tctggcgcta acctgtacgc ttcgggctct 840
gggcctcagc agacccagtc tttcacgtca caggactggc cgttcctgta ctctctcttc 900
caggtgaact caaattacat cctctccggc attagcggga cacgcctgtc aatcactttc 960
ccaaacattg gcgggctccc aggctccacc acgacacact cgctgaactc tgccagggtc 1020

```
aattactccg gcggggtttc atccggcctc atcggggcga ccaacctgaa tcataacttc   1080
aattgctcga ccgtcctgcc accactctct acgccattcg ttcgctcatg gctcgactcc   1140
ggcacagata gggaggggt cgctaccagc acgaactggc agactgagtc cttccagact   1200
accctcagcc tgcgctgcgg cgctttcagc gctaggggga actcgaatta cttcccggac   1260
tacttcatcc ggaacatttc cggcgtcccc ctggttatca ggaacgagga tctcacacgg   1320
ccactgcact acaaccagat ccgcaatatt gagtcaccat ccggcacgcc cggcggcgcc   1380
agggcttacc tcgtgagcgt ccataaccgc aagaacaata tctacgcggc taacgagaat   1440
ggcaccatga ttcacctggc gccagaggac tacacagggt tcactatctc gcctattcat   1500
gctacgcagg tcaacaatca gacaaggact ttcatctcgg agaagttcgg caaccagggg   1560
gattctctcc ggttcgagca gaacaatacg acagccaggt acaccctgcg gggcaacggg   1620
aattcttaca acctctacct gcgcgtgtcc tccatcggca actcaacaat ccgcgtgact   1680
attaatggga gggtctacac cgcgacgaac gttaatacta ccacgaacaa tgacggcgtg   1740
aacgataatg gggctaggtt cagcgacatc aacattggca atctcgtcgc ctcttcaaac   1800
agcgacgtgc cgctcgatat taacgtcacc ctgaattcgg gcacgcagtt cgatatcatg   1860
aacatcatgc tggtgccaac caatatttcc cctctctact ag                     1902
```

<210> SEQ ID NO 10
<211> LENGTH: 623
<212> TYPE: PRT
<213> ORGANISM: Bacillus thuringiensis

<400> SEQUENCE: 10

```
Met Asn Asn Val Leu Asn Ser Glu Arg Pro Thr Lys Cys Asp Ala Tyr
1               5                   10                  15

Asn Val Val Ala His Asp Pro Phe Ser Phe Glu His Lys Ser Val Asp
            20                  25                  30

Thr Ile Gln Lys Glu Trp Val Glu Trp Lys Arg Thr Asp His Ser Leu
        35                  40                  45

Tyr Val Ser Pro Ile Val Gly Thr Ile Ala Lys Phe Leu Leu Lys Lys
    50                  55                  60

Ile Gly Gly Leu Ile Gly Lys Arg Ile Leu Ser Glu Leu Lys Asn Leu
65                  70                  75                  80

Ile Phe Pro Ser Gly Ser Thr Ala Ser Met Gln Asp Ile Leu Arg Gly
                85                  90                  95

Ala Glu Gln Phe Leu Asn Gln Arg Leu Asp Glu Asp Thr Phe Ala Arg
            100                 105                 110

Val Glu Ala Glu Leu Arg Gly Leu Gln Ala Asn Val Glu Glu Phe Asn
        115                 120                 125

Arg Gln Val Asp Asn Phe Leu Asn Pro Asn Gln Thr Pro Val Pro Leu
    130                 135                 140

Ala Ile Ile Asp Ser Val Asn Thr Leu Gln Gln Leu Phe Leu Ser Arg
145                 150                 155                 160

Leu Pro Gln Phe Gln Ile Gln Arg Tyr Gln Leu Leu Leu Pro Leu
                165                 170                 175

Phe Ala Gln Ala Ala Asn Leu His Leu Thr Phe Ile Arg Asp Val Ile
            180                 185                 190

Leu Asn Ala Asp Glu Trp Gly Ile Pro Glu Ala Thr Val Arg Thr Tyr
        195                 200                 205

Arg Gln His Leu Gln Arg Tyr Thr Gln Asp Tyr Ser Asn Tyr Cys Ile
    210                 215                 220
```

```
Asn Thr Tyr Gln Thr Ala Phe Arg Gly Leu Asn Thr Arg Leu His Asp
225                 230                 235                 240

Met Leu Glu Phe Arg Thr Phe Met Phe Leu Asn Val Leu Asp Tyr Val
            245                 250                 255

Ser Ile Trp Ser Leu Phe Lys Tyr Gln Ser Leu Met Val Thr Ser Thr
        260                 265                 270

Ala Asn Leu Tyr Ala Ser Gly Ser Gly Ser Asn Gln Phe Phe Thr Ala
        275                 280                 285

Gln Ala Trp Pro Phe Leu Tyr Ser Leu Phe Gln Val Asn Ser Asn Tyr
290                 295                 300

Ile Met Ser Asn Phe Gly Gly Asn Arg Glu Thr Ala Thr Ala Gly Val
305                 310                 315                 320

Pro Gly Leu Gly Gly Phe Leu Phe Asn Phe Leu Phe Ser Phe Arg Val
                325                 330                 335

Asn Tyr Thr Gly Gly Val Ser Ser Gly Leu Leu Gly Val Glu Gly Ile
            340                 345                 350

Leu Asn Asn Phe Ser Cys Asn Ser Ser Leu Ser Thr Pro Ile Val Arg
        355                 360                 365

Ser Trp Leu Asp Ser Gly Ile Glu Arg Ser Asp Ile Gln His Asn Trp
370                 375                 380

Arg Thr Asp Met Phe Leu Arg Ala Asn Gly Val Pro Cys Gly Ala Phe
385                 390                 395                 400

Pro Leu Thr Leu Val Met Tyr Pro Asn Val Thr Met Asn Tyr Phe Pro
                405                 410                 415

Asp Tyr Phe Ile Arg Asn Ile Ser Gly Ile Ile Gln Asn Ile Asp Asn
            420                 425                 430

Met Asn Leu Ser Arg Pro Leu His Phe Asn Glu Val Arg Asp Leu Arg
        435                 440                 445

Gly Asn Glu Val Ala Thr Leu Val Ser Val His Ser Thr Lys Asn Asn
450                 455                 460

Ile Tyr Ala Ala His Glu Asn Gly Thr Met Ile His Leu Ala Pro Glu
465                 470                 475                 480

Asp Tyr Thr Gly Phe Thr Met Ser Pro Ile His Ala Thr Gln Val Asn
                485                 490                 495

Asn Gln Thr Arg Thr Phe Ile Ser Glu Lys Phe Gly Asn Gln Gly Asp
            500                 505                 510

Ser Leu Arg Phe Glu Gln Thr Asn Thr Thr Ala Arg Tyr Thr Phe Arg
        515                 520                 525

Gly Asn Gly Asn Asn Tyr Asn Leu Tyr Leu Arg Val Ser Ser Gln Gly
530                 535                 540

Asn Ser Asn Ile Arg Val Thr Ile Asn Gly Arg Asn Tyr Thr Ser Asn
545                 550                 555                 560

Val Asn Thr Thr Thr Asn Asn Asp Gly Val Leu Asp Asn Glu Ala Arg
                565                 570                 575

Phe Ser Asp Ile Leu Ile Gly Asn Val Val Ala Ser Ala Asn Thr Asn
            580                 585                 590

Val Pro Leu Asp Ile Asn Val Thr Phe Asn Thr Gly Thr Lys Phe Glu
        595                 600                 605

Leu Met Asn Ile Met Phe Val Pro Thr Asn Leu Leu Pro Leu Tyr
610                 615                 620

<210> SEQ ID NO 11
<211> LENGTH: 631
```

<212> TYPE: PRT
<213> ORGANISM: Bacillus thuringiensis

<400> SEQUENCE: 11

Met Asn Asn Val Leu Asn Ser Gly Arg Thr Thr Ile Cys Asp Gly His
1               5                   10                  15

Asn Val Met Ala Gln Asp Pro Phe Ser Phe Gln His Lys Ser Leu Asp
            20                  25                  30

Thr Ile Gln Lys Glu Trp Thr Glu Trp Lys Arg Asp Asp His Ser Leu
        35                  40                  45

Tyr Val Ala Pro Val Val Gly Thr Val Ala Ile Phe Leu Leu Lys Lys
    50                  55                  60

Leu Gly Gly Phe Ala Ala Lys Arg Ile Leu Asn Gly Leu Trp Asp Leu
65                  70                  75                  80

Val Phe Pro Asn Asp Asn Thr Lys Leu Met Gln Asp Ile Leu Arg Glu
                85                  90                  95

Thr Glu Lys Phe Leu Asn Gln Arg Leu Asn Ala Asp Thr Leu Ser Arg
            100                 105                 110

Val Asn Ala Glu Leu Glu Gly Leu Gln Lys Asn Val Ala Glu Phe Asn
        115                 120                 125

Arg Gln Val Asp Asn Phe Leu Asn Pro Asn Arg Asn Pro Thr Leu Leu
130                 135                 140

Ser Ile Thr Ser Pro Val Asn Thr Met Gln Gln Leu Phe Leu Asn Arg
145                 150                 155                 160

Leu Thr Gln Phe Gln Leu Arg Gly Tyr Glu Leu Leu Leu Pro Leu
                165                 170                 175

Phe Ala Gln Ala Ala Asn Leu His Leu Ser Phe Ile Arg Asp Val Ile
                180                 185                 190

Leu Asn Ala Glu Glu Trp Gly Ile Ser Ala Ala Thr Leu Arg Thr Tyr
            195                 200                 205

Arg Gly Tyr Leu Lys Asp Tyr Thr Lys Glu Tyr Ser Asn Tyr Cys Ile
    210                 215                 220

Asn Thr Tyr Gln Thr Ala Phe Lys Lys Leu Asn Thr Pro Leu His Glu
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
            260                 265                 270

Ala Asn Leu Tyr Ala Ser Gly Ser Gly Pro Gln Gln Lys Gln Ser Phe
        275                 280                 285

Ser Ala Gln Asn Trp Pro Phe Leu Tyr Ser Leu Phe Gln Val Asn Ser
    290                 295                 300

Asn Tyr Val Leu Thr Gly Phe Ser Gly Phe Arg Asn Ser Phe Thr Met
305                 310                 315                 320

Pro Asn Ile Gly Gly Phe Pro Gly Ser Thr Thr His Ala Leu Phe
                325                 330                 335

Ser Ala Arg Ala Asn Tyr Ser Gly Gly Ile Ser Ser Gly Ile Ile Gly
            340                 345                 350

Met Thr Asn Ser Asn His Asn Phe Asn Cys Ser Thr Ala Ser Leu Gln
        355                 360                 365

Thr Pro Tyr Thr Arg Ser Trp Leu Asp Ser Gly Arg Asp Gln His Ala
    370                 375                 380

Ile Asn Thr Phe Thr Asp Trp Gln Thr Glu Cys Phe Gln Thr Thr Ser
385                 390                 395                 400

```
Asp Ser Trp Cys Gly Ala Phe Val Pro Arg Gly Asn Thr Asn Tyr Phe
            405                 410                 415

Pro Asp Tyr Phe Ile Arg Asn Ile Ser Gly Val Ser Leu Val Val Gly
        420                 425                 430

Asn Glu Asp Leu Arg Arg Pro Leu His Tyr Asn Glu Ile Arg Asn Ile
            435                 440                 445

Ala Ser Pro Ser Gly Thr Pro Gly Gly Arg Ala Tyr Met Ala Ser
    450                 455                 460

Val His Asn Arg Lys Asn Asn Ile Tyr Ala Ala His Glu Asn Gly Thr
465                 470                 475                 480

Met Ile His Leu Ala Pro Asp Asp Asn Thr Gly Phe Ile Ile Ser Pro
                485                 490                 495

Ile His Ala Thr Gln Val Asn Thr Gln Asn Arg Thr Phe Ile Ser Glu
            500                 505                 510

Lys Phe Gly Asn Gln Gly Asp Ser Leu Arg Phe Glu Gln Thr Asn Thr
        515                 520                 525

Thr Ala Arg Tyr Thr Phe Arg Gly Lys Gly Asn Ser Tyr Asn Leu Tyr
    530                 535                 540

Leu Arg Val Ser Ser Leu Gly Asn Ser Thr Ile Arg Val Thr Ile Asn
545                 550                 555                 560

Gly Lys Val Tyr Thr Val Pro Asn Val Asn Thr Thr Asn Asn Asp
                565                 570                 575

Gly Val Ile Asp Asn Gly Ser Arg Phe Ser Asp Val Tyr Ile Gly Asn
            580                 585                 590

Val Val Ala Asn Asp Lys Thr Asn Val Pro Leu Asp Ile Asn Val Thr
                595                 600                 605

Phe Asn Ser Gly Thr Gln Phe Glu Leu Met Asn Ile Met Cys Ile Pro
            610                 615                 620

Thr Asn Ile Thr Pro Leu Tyr
625                 630

<210> SEQ ID NO 12
<211> LENGTH: 633
<212> TYPE: PRT
<213> ORGANISM: Bacillus thuringiensis

<400> SEQUENCE: 12

Met Asn Ser Val Leu Asn Ser Gly Arg Thr Thr Ile Cys Asp Ala Tyr
1               5                   10                  15

Asn Val Ala Ala His Asp Pro Phe Ser Phe Gln His Lys Ser Leu Asp
            20                  25                  30

Thr Val Gln Lys Glu Trp Thr Glu Trp Lys Lys Asn Asn His Ser Leu
        35                  40                  45

Tyr Leu Asp Pro Ile Val Gly Thr Val Ala Ser Phe Leu Leu Lys Lys
    50                  55                  60

Val Gly Ser Leu Val Gly Lys Arg Ile Leu Ser Glu Leu Arg Asn Leu
65                  70                  75                  80

Ile Phe Pro Ser Gly Ser Thr Asn Leu Met Gln Asp Ile Leu Arg Glu
                85                  90                  95

Thr Glu Gln Phe Leu Asn Gln Arg Leu Asn Thr Asp Thr Leu Ala Arg
            100                 105                 110

Val Asn Ala Glu Leu Ile Gly Leu Gln Ala Asn Ile Arg Glu Phe Asn
        115                 120                 125

Gln Gln Val Asp Asn Phe Leu Asn Pro Thr Gln Asn Pro Val Pro Leu
```

```
            130                 135                 140
Ser Ile Thr Ser Ser Val Asn Thr Met Gln Gln Leu Phe Leu Asn Arg
145                 150                 155                 160

Leu Pro Gln Phe Gln Ile Gln Gly Tyr Gln Leu Leu Leu Pro Leu
            165                 170                 175

Phe Ala Gln Ala Ala Asn Leu His Leu Ser Phe Ile Arg Asp Val Ile
            180                 185                 190

Leu Asn Ala Asp Glu Trp Gly Ile Ser Ala Ala Thr Leu Arg Thr Tyr
            195                 200                 205

Arg Asp Tyr Leu Arg Asn Tyr Thr Arg Asp Tyr Ser Asn Tyr Cys Ile
            210                 215                 220

Asn Thr Tyr Gln Thr Ala Phe Arg Gly Leu Asn Thr Arg Leu His Asp
225                 230                 235                 240

Met Leu Glu Phe Arg Thr Tyr Met Phe Leu Asn Val Phe Glu Tyr Val
            245                 250                 255

Ser Ile Trp Ser Leu Phe Lys Tyr Gln Ser Leu Met Val Ser Ser Gly
            260                 265                 270

Ala Asn Leu Tyr Ala Ser Gly Ser Gly Pro Gln Gln Thr Gln Ser Phe
            275                 280                 285

Thr Ser Gln Asp Trp Pro Phe Leu Tyr Ser Leu Phe Gln Val Asn Ser
            290                 295                 300

Asn Tyr Ile Leu Ser Gly Ile Ser Gly Thr Arg Leu Ser Ile Thr Phe
305                 310                 315                 320

Pro Asn Ile Gly Gly Leu Pro Gly Ser Thr Thr Thr His Ser Leu Asn
            325                 330                 335

Ser Ala Arg Val Asn Tyr Ser Gly Gly Val Ser Ser Gly Leu Ile Gly
            340                 345                 350

Ala Thr Asn Leu Asn His Asn Phe Asn Cys Ser Thr Val Leu Pro Pro
            355                 360                 365

Leu Ser Thr Pro Phe Val Arg Ser Trp Leu Asp Ser Gly Thr Asp Arg
            370                 375                 380

Glu Gly Val Ala Thr Ser Thr Asn Trp Gln Thr Glu Ser Phe Gln Thr
385                 390                 395                 400

Thr Leu Ser Leu Arg Cys Gly Ala Phe Ser Ala Arg Gly Asn Ser Asn
            405                 410                 415

Tyr Phe Pro Asp Tyr Phe Ile Arg Asn Ile Ser Gly Val Pro Leu Val
            420                 425                 430

Ile Arg Asn Glu Asp Leu Thr Arg Pro Leu His Tyr Asn Gln Ile Arg
            435                 440                 445

Asn Ile Glu Ser Pro Ser Gly Thr Pro Gly Gly Ala Arg Ala Tyr Leu
            450                 455                 460

Val Ser Val His Asn Arg Lys Asn Asn Ile Tyr Ala Ala Asn Glu Asn
465                 470                 475                 480

Gly Thr Met Ile His Leu Ala Pro Glu Asp Tyr Thr Gly Phe Thr Ile
            485                 490                 495

Ser Pro Ile His Ala Thr Gln Val Asn Asn Gln Thr Arg Thr Phe Ile
            500                 505                 510

Ser Glu Lys Phe Gly Asn Gln Gly Asp Ser Leu Arg Phe Glu Gln Asn
            515                 520                 525

Asn Thr Thr Ala Arg Tyr Thr Leu Arg Gly Asn Gly Asn Ser Tyr Asn
            530                 535                 540

Leu Tyr Leu Arg Val Ser Ser Ile Gly Asn Ser Thr Ile Arg Val Thr
545                 550                 555                 560
```

```
Ile Asn Gly Arg Val Tyr Thr Ala Thr Asn Val Asn Thr Thr Thr Asn
            565                 570                 575

Asn Asp Gly Val Asn Asp Asn Gly Ala Arg Phe Ser Asp Ile Asn Ile
            580                 585                 590

Gly Asn Ile Val Ala Ser Ser Asn Ser Asp Val Pro Leu Asp Ile Asn
            595                 600                 605

Val Thr Leu Asn Ser Gly Thr Gln Phe Asp Leu Met Asn Ile Met Leu
            610                 615                 620

Val Pro Thr Asn Ile Ser Pro Leu Tyr
625                 630

<210> SEQ ID NO 13
<211> LENGTH: 623
<212> TYPE: PRT
<213> ORGANISM: Artificial Sequence
<220> FEATURE:
<223> OTHER INFORMATION: Mutant BT-0016

<400> SEQUENCE: 13

Met Asn Asn Val Leu Asn Ser Glu Arg Pro Thr Lys Cys Asp Ala Tyr
1               5                   10                  15

Asn Val Val Ala His Asp Pro Phe Ser Phe Glu His Lys Ser Val Asp
            20                  25                  30

Thr Ile Gln Lys Glu Trp Val Glu Trp Lys Arg Thr Asp His

```
Gln Ala Trp Pro Phe Leu Tyr Ser Leu Phe Gln Val Asn Ser Asn Tyr
    290                 295                 300

Ile Met Ser Asn Phe Gly Gly Asn Arg Glu Thr Ala Thr Ala Gly Val
305                 310                 315                 320

Pro Gly Leu Gly Gly Phe Leu Phe Asn Phe Leu Phe Ser Phe Arg Val
                325                 330                 335

Asn Tyr Thr Gly Gly Val Ser Ser Gly Leu Leu Gly Val Glu Gly Ile
            340                 345                 350

Leu Asn Asn Phe Ser Cys Asn Ser Ser Leu Ser Thr Pro Ile Val Arg
        355                 360                 365

Ser Trp Leu Asp Ser Gly Ile Glu Arg Ser Asp Ile Gln His Asn Trp
    370                 375                 380

Arg Thr Asp Met Phe Leu Arg Ala Asn Gly Val Pro Cys Gly Ala Phe
385                 390                 395                 400

Pro Leu Thr Leu Val Met Tyr Pro Asn Val Thr Met Asn Tyr Phe Pro
                405                 410                 415

Asp Tyr Phe Ile Arg Asn Ile Ser Gly Ile Ile Gln Asn Ile Asp Asn
            420                 425                 430

Met Asn Leu Ser Arg Pro Leu His Phe Asn Glu Val Arg Asp Leu Arg
        435                 440                 445

Gly Asn Glu Val Ala Thr Leu Val Ser Val His Ser Thr Lys Asn Asn
    450                 455                 460

Ile Tyr Ala Ala His Glu Asn Gly Thr Met Ile His Leu Ala Pro Glu
465                 470                 475                 480

Asp Tyr Thr Gly Phe Thr Met Ser Pro Ile His Ala Thr Gln Val Asn
                485                 490                 495

Asn Gln Thr Arg Thr Phe Ile Ser Glu Lys Phe Gly Asn Gln Gly Asp
            500                 505                 510

Ser Leu Arg Phe Glu Gln Thr Asn Thr Thr Ala Arg Tyr Thr Phe Arg
        515                 520                 525

Gly Asn Gly Asn Asn Tyr Asn Leu Tyr Leu Arg Val Ser Ser Gln Gly
    530                 535                 540

Asn Ser Asn Ile Arg Val Thr Ile Asn Gly Arg Asn Tyr Thr Ser Asn
545                 550                 555                 560

Val Asn Thr Thr Thr Asn Asn Asp Gly Val Leu Asp Asn Glu Ala Arg
                565                 570                 575

Phe Ser Asp Ile Leu Ile Gly Asn Val Val Ala Ser Ala Asn Thr Asn
            580                 585                 590

Val Pro Leu Asp Ile Asn Val Thr Phe Asn Thr Gly Thr Lys Phe Glu
        595                 600                 605

Leu Met Asn Leu Met Phe Val Pro Thr Asn Ile Leu Pro Leu Tyr
    610                 615                 620

<210> SEQ ID NO 14
<211> LENGTH: 631
<212> TYPE: PRT
<213> ORGANISM: Artificial Sequence
<220> FEATURE:
<223> OTHER INFORMATION: Mutant BT-0026 protein.

<400> SEQUENCE: 14

Met Asn Asn Val Leu Asn Ser Gly Arg Thr Thr Ile Cys Asp Gly His
1               5                   10                  15

Asn Val Met Ala Gln Asp Pro Phe Ser Phe Gln His Lys Ser Leu Asp
            20                  25                  30
```

```
Thr Ile Gln Lys Glu Trp Thr Glu Trp Lys Arg Asp Asp His Ser Leu
            35                  40                  45

Tyr Val Ala Pro Val Val Gly Thr Val Ala Ile Phe Leu Leu Lys Lys
        50                  55                  60

Leu Gly Gly Phe Ala Ala Lys Arg Ile Leu Asn Gly Leu Trp Asp Leu
65                  70                  75                  80

Val Phe Pro Asn Asp Asn Thr Lys Leu Met Gln Asp Ile Leu Arg Glu
                85                  90                  95

Thr Glu Lys Phe Leu Asn Gln Arg Leu Asn Ala Asp Thr Leu Ser Arg
            100                 105                 110

Val Asn Ala Glu Leu Glu Gly Leu Gln Lys Asn Val Ala Glu Phe Asn
        115                 120                 125

Arg Gln Val Asp Asn Phe Leu Asn Pro Asn Arg Asn Pro Thr Leu Leu
    130                 135                 140

Ser Ile Thr Ser Pro Val Asn Thr Met Gln Gln Leu Phe Leu Asn Arg
145                 150                 155                 160

Leu Thr Gln Phe Gln Leu Arg Gly Tyr Glu Leu Leu Leu Leu Pro Leu
                165                 170                 175

Phe Ala Gln Ala Ala Asn Leu His Leu Ser Phe Ile Arg Asp Val Ile
            180                 185                 190

Leu Asn Ala Glu Glu Trp Gly Ile Ser Ala Ala Thr Leu Arg Thr Tyr
        195                 200                 205

Arg Gly Tyr Leu Lys Asp Tyr Thr Lys Glu Tyr Ser Asn Tyr Cys Ile
    210                 215                 220

Asn Thr Tyr Gln Thr Ala Phe Lys Lys Leu Asn Thr Pro Leu His Glu
225                 230                 235                 240

Met Leu Glu Phe Arg Thr Tyr Met Phe Leu Asn Val Phe Glu Tyr Val
                245                 250                 255

Ser Ile Trp Ser Leu Phe Lys Tyr Gln Ser Leu Leu Val Ser Ser Gly
            260                 265                 270

Ala Asn Leu Tyr Ala Ser Gly Ser Gly Pro Gln Gln Lys Gln Ser Phe
        275                 280                 285

Ser Ala Gln Asn Trp Pro Phe Leu Tyr Ser Leu Phe Gln Val Asn Ser
    290                 295                 300

Asn Tyr Val Leu Thr Gly Phe Ser Gly Phe Arg Asn Ser Phe Thr Met
305                 310                 315                 320

Pro Asn Ile Gly Gly Phe Pro Gly Ser Thr Thr His Ala Leu Phe
                325                 330                 335

Ser Ala Arg Ala Asn Tyr Ser Gly Gly Ile Ser Ser Gly Ile Ile Gly
            340                 345                 350

Met Thr Asn Ser Asn His Asn Phe Asn Cys Ser Thr Ala Ser Leu Gln
        355                 360                 365

Thr Pro Tyr Thr Arg Ser Trp Leu Asp Ser Gly Arg Asp Gln His Ala
    370                 375                 380

Ile Asn Thr Phe Thr Asp Trp Gln Thr Glu Cys Phe Gln Thr Thr Ser
385                 390                 395                 400

Asp Ser Trp Cys Gly Ala Phe Val Pro Arg Gly Asn Thr Asn Tyr Phe
                405                 410                 415

Pro Asp Tyr Phe Ile Arg Asn Ile Ser Gly Val Ser Leu Val Val Gly
            420                 425                 430

Asn Glu Asp Leu Arg Arg Pro Leu His Tyr Asn Glu Ile Arg Asn Ile
        435                 440                 445
```

-continued

```
Ala Ser Pro Ser Gly Thr Pro Gly Gly Gly Arg Ala Tyr Met Ala Ser
            450                 455                 460

Val His Asn Arg Lys Asn Asn Ile Tyr Ala Ala His Glu Asn Gly Thr
465                 470                 475                 480

Met Ile His Leu Ala Pro Asp Asp Asn Thr Gly Phe Ile Ile Ser Pro
                485                 490                 495

Ile His Ala Thr Gln Val Asn Thr Gln Asn Arg Thr Phe Ile Ser Glu
            500                 505                 510

Lys Phe Gly Asn Gln Gly Asp Ser Leu Arg Phe Glu Gln Thr Asn Thr
            515                 520                 525

Thr Ala Arg Tyr Thr Phe Arg Gly Lys Gly Asn Ser Tyr Asn Leu Tyr
530                 535                 540

Leu Arg Val Ser Ser Leu Gly Asn Ser Thr Ile Arg Val Thr Ile Asn
545                 550                 555                 560

Gly Lys Val Tyr Thr Val Pro Asn Val Asn Thr Thr Asn Asn Asp
                565                 570                 575

Gly Val Ile Asp Asn Gly Ser Arg Phe Ser Asp Val Tyr Ile Gly Asn
            580                 585                 590

Val Val Ala Asn Asp Lys Thr Asn Val Pro Leu Asp Leu Asn Val Thr
            595                 600                 605

Phe Asn Ser Gly Thr Gln Phe Glu Leu Met Asn Leu Met Cys Ile Pro
610                 615                 620

Thr Asn Ile Thr Pro Leu Tyr
625                 630
```

<210> SEQ ID NO 15
<211> LENGTH: 633
<212> TYPE: PRT
<213> ORGANISM: Artificial Sequence
<220> FEATURE:
<223> OTHER INFORMATION: Mutant BT-0032 protein.

<400> SEQUENCE: 15

```
Met Asn Ser Val Leu Asn Ser Gly Arg Thr Thr Ile Cys Asp Ala Tyr
1               5                   10                  15

Asn Val Ala Ala His Asp Pro Phe Ser Phe Gln His Lys Ser Leu Asp
            20                  25                  30

Thr Val Gln Lys Glu Trp Thr Glu Trp Lys Lys Asn Asn His Ser Leu
        35                  40                  45

Tyr Leu Asp Pro Ile Val Gly Thr Val Ala Ser Phe Leu Leu Lys Lys
    50                  55                  60

Val Gly Ser Leu Val Gly Lys Arg Ile Leu Ser Glu Leu Arg Asn Leu
65                  70                  75                  80

Ile Phe Pro Ser Gly Ser Thr Asn Leu Met Gln Asp Ile Leu Arg Glu
                85                  90                  95

Thr Glu Gln Phe Leu Asn Gln Arg Leu Asn Thr Asp Thr Leu Ala Arg
            100                 105                 110

Val Asn Ala Glu Leu Ile Gly Leu Gln Ala Asn Ile Arg Glu Phe Asn
        115                 120                 125

Gln Gln Val Asp Asn Phe Leu Asn Pro Thr Gln Asn Pro Val Pro Leu
    130                 135                 140

Ser Ile Thr Ser Ser Val Asn Thr Met Gln Gln Leu Phe Leu Asn Arg
145                 150                 155                 160

Leu Pro Gln Phe Gln Ile Gln Gly Tyr Gln Leu Leu Leu Leu Pro Leu
                165                 170                 175
```

```
Phe Ala Gln Ala Ala Asn Leu His Leu Ser Phe Ile Arg Asp Val Ile
            180                 185                 190
Leu Asn Ala Asp Glu Trp Gly Ile Ser Ala Ala Thr Leu Arg Thr Tyr
        195                 200                 205
Arg Asp Tyr Leu Arg Asn Tyr Thr Arg Asp Tyr Ser Asn Tyr Cys Ile
    210                 215                 220
Asn Thr Tyr Gln Thr Ala Phe Arg Gly Leu Asn Thr Arg Leu His Asp
225                 230                 235                 240
Met Leu Glu Phe Arg Thr Tyr Met Phe Leu Asn Val Phe Glu Tyr Val
            245                 250                 255
Ser Ile Trp Ser Leu Phe Lys Tyr Gln Ser Leu Met Val Ser Ser Gly
        260                 265                 270
Ala Asn Leu Tyr Ala Ser Gly Ser Gly Pro Gln Gln Thr Gln Ser Phe
    275                 280                 285
Thr Ser Gln Asp Trp Pro Phe Leu Tyr Ser Leu Phe Gln Val Asn Ser
    290                 295                 300
Asn Tyr Ile Leu Ser Gly Ile Ser Gly Thr Arg Leu Ser Ile Thr Phe
305                 310                 315                 320
Pro Asn Ile Gly Gly Leu Pro Gly Ser Thr Thr His Ser Leu Asn
            325                 330                 335
Ser Ala Arg Val Asn Tyr Ser Gly Gly Val Ser Ser Gly Leu Ile Gly
        340                 345                 350
Ala Thr Asn Leu Asn His Asn Phe Asn Cys Ser Thr Val Leu Pro Pro
    355                 360                 365
Leu Ser Thr Pro Phe Val Arg Ser Trp Leu Asp Ser Gly Thr Asp Arg
370                 375                 380
Glu Gly Val Ala Thr Ser Thr Asn Trp Gln Thr Glu Ser Phe Gln Thr
385                 390                 395                 400
Thr Leu Ser Leu Arg Cys Gly Ala Phe Ser Ala Arg Gly Asn Ser Asn
            405                 410                 415
Tyr Phe Pro Asp Tyr Phe Ile Arg Asn Ile Ser Gly Val Pro Leu Val
        420                 425                 430
Ile Arg Asn Glu Asp Leu Thr Arg Pro Leu His Tyr Asn Gln Ile Arg
    435                 440                 445
Asn Ile Glu Ser Pro Ser Gly Thr Pro Gly Gly Ala Arg Ala Tyr Leu
    450                 455                 460
Val Ser Val His Asn Arg Lys Asn Asn Ile Tyr Ala Ala Asn Glu Asn
465                 470                 475                 480
Gly Thr Met Ile His Leu Ala Pro Glu Asp Tyr Thr Gly Phe Thr Ile
            485                 490                 495
Ser Pro Ile His Ala Thr Gln Val Asn Asn Gln Thr Arg Thr Phe Ile
        500                 505                 510
Ser Glu Lys Phe Gly Asn Gln Gly Asp Ser Leu Arg Phe Glu Gln Asn
    515                 520                 525
Asn Thr Thr Ala Arg Tyr Thr Leu Arg Gly Asn Gly Asn Ser Tyr Asn
    530                 535                 540
Leu Tyr Leu Arg Val Ser Ser Ile Gly Asn Ser Thr Ile Arg Val Thr
545                 550                 555                 560
Ile Asn Gly Arg Val Tyr Thr Ala Thr Asn Val Asn Thr Thr Thr Asn
            565                 570                 575
Asn Asp Gly Val Asn Asp Asn Gly Ala Arg Phe Ser Asp Ile Asn Ile
        580                 585                 590
Gly Asn Leu Val Ala Ser Ser Asn Ser Asp Val Pro Leu Asp Ile Asn
```

```
                595                 600                 605
Val Thr Leu Asn Ser Gly Thr Gln Phe Asp Ile Met Asn Ile Met Leu
    610                 615                 620

Val Pro Thr Asn Ile Ser Pro Leu Tyr
625                 630

<210> SEQ ID NO 16
<211> LENGTH: 30
<212> TYPE: DNA
<213> ORGANISM: Artificial Sequence
<220> FEATURE:
<223> OTHER INFORMATION: Forward Cry2-like primer with added cloning
      restriction site

<400> SEQUENCE: 16
gtttaaacat gaataatgta ttgaatagcg                                    30

<210> SEQ ID NO 17
<211> LENGTH: 31
<212> TYPE: DNA
<213> ORGANISM: Artificial Sequence
<220> FEATURE:
<223> OTHER INFORMATION: Reverse Cry2-like primer with added cloning
      restriction site.

<400> SEQUENCE: 17
ggcgcgcctt aatacagtgg tagaagatta g                                  31
```